United States Patent
Ren et al.

(10) Patent No.: US 10,684,272 B2
(45) Date of Patent: Jun. 16, 2020

(54) MODULATION OF HEPATITIS B VIRUS REPLICATION

(71) Applicant: AGENCY FOR SCIENCE, TECHNOLOGY AND RESEARCH, Singapore (SG)

(72) Inventors: Ee Chee Ren, Singapore (SG); Hul Ling Ko, Singapore (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 0 days.

(21) Appl. No.: 15/745,431

(22) PCT Filed: Jul. 15, 2016

(86) PCT No.: PCT/SG2016/050338
§ 371 (c)(1),
(2) Date: Jan. 16, 2018

(87) PCT Pub. No.: WO2017/010950
PCT Pub. Date: Jan. 19, 2017

(65) Prior Publication Data
US 2018/0209958 A1    Jul. 26, 2018

(30) Foreign Application Priority Data
Jul. 15, 2015  (SG) .......................... 10201505551 U

(51) Int. Cl.
| | | |
|---|---|---|
| *A61K 48/00* | (2006.01) | |
| *C07H 21/02* | (2006.01) | |
| *C07H 21/04* | (2006.01) | |
| *G01N 33/50* | (2006.01) | |
| *A61K 38/17* | (2006.01) | |
| *C07K 14/00* | (2006.01) | |
| *C07K 14/02* | (2006.01) | |
| *A61P 1/16* | (2006.01) | |
| *A61P 31/20* | (2006.01) | |
| *A61K 31/713* | (2006.01) | |
| *G01N 33/576* | (2006.01) | |

(52) U.S. Cl.
CPC ........ *G01N 33/5008* (2013.01); *A61K 31/713* (2013.01); *A61K 38/17* (2013.01); *A61P 1/16* (2018.01); *A61P 31/20* (2018.01); *C07K 14/00* (2013.01); *C07K 14/02* (2013.01); *G01N 33/5761* (2013.01); *C12N 2500/00* (2013.01)

(58) Field of Classification Search
CPC . A61K 2300/00; A61K 31/135; C12N 15/113
See application file for complete search history.

(56) References Cited

U.S. PATENT DOCUMENTS

| | | | | |
|---|---|---|---|---|
| 7,939,115 B2 * | 5/2011 | Huang | ..................... | A23L 33/16 424/725 |
| 2002/0045161 A1 | 4/2002 | Allaway et al. | | |
| 2002/0045191 A1 | 4/2002 | Schneider et al. | | |
| 2013/0131094 A1 * | 5/2013 | Nakache | ............. | C07D 409/14 514/275 |
| 2014/0256742 A1 * | 9/2014 | Baker | ................. | A61K 31/135 514/255.01 |

FOREIGN PATENT DOCUMENTS

| | | |
|---|---|---|
| WO | WO 02/094796 A2 | 11/2002 |
| WO | WO 2010/127246 A2 | 11/2010 |
| WO | WO 2011/106106 A2 | 9/2011 |
| WO | WO 2013/106548 A1 | 7/2013 |
| WO | WO 2013/139895 A1 | 9/2015 |

OTHER PUBLICATIONS

Zhang et al. (J Lab Clin Med, vol. 147, No. 2, 58-66, 2006).*
Torres-Padilla et al. (Mechanisms of Development, 109, 2001, pp. 183-193).*
Supplementary Partial European Search Report for EP Application No. 16 82 4803, 7 pgs. (dated Jun. 27, 2018).
Xin-Yu Zhao, et al., "Inhibition of Snail Family Transcriptional Repressor 2 (SNAI2) Enhances Multidrug Resistance of Hepatocellular Carcinoma Cells," PLOS ONE, vol. 11, No. 10, 19 pgs. (Oct. 19, 2016).
PCT International Search Report for PCT Counterpart Application No. PCT/SG2016/050338, 8 pgs. (dated Oct. 3, 2016).
PCT Written Opinion for PCT Counterpart Application No, PCT/SG2016/050338, 9 pgs. (dated Oct. 3, 2016).
Yanyan Zheng, et al., "Suppression of hepatitis B virus replication by SRPK1 and SRPK2 via a pathway independent of the phosphorylation of the viral core protein," Virology, vol. 342, No, 1, pp. 150-158 (Aug. 24, 2005).
Moo Son, et al., "The hepatitis B virus X protein induced fibrosis in Huh7 cells" Appl. Biol. Chem, vol. 50, No. 1, pp. 25-29 (Mar. 31, 2016).
Yong Kwang Park et al., "Cleaved c-FLIP mediates the antiviral effect of TNF-a against hepatitis B virus by dysregulating hepatocyte nuclear factors," Journal of Hepatology, Sep. 25, 2015, 268-277, vol. 64, 10 pages.

(Continued)

*Primary Examiner* — Amy H Bowman
(74) *Attorney, Agent, or Firm* — Womble Bond Dickinson (US) LLP

(57) ABSTRACT

Presently disclosed is a method of modulating Hepatitis B virus (HBV) replication, by contacting the cell with at least one agent that modulates at least one factor from a specified group consisting of SNAI2, SOX7 and other factors, the screening of said agent and use thereof in a medicament for treating HBV infection or disease or condition associated with a HBV infection in a subject. In one preferred embodiment, the agent is one peptide derived from SOX7 or SNAI2 or stapled peptides thereof. As a separate invention, a method of identifying at least one factor that modulates replication of a virus is also disclosed.

5 Claims, 67 Drawing Sheets

Specification includes a Sequence Listing.

(56) References Cited

OTHER PUBLICATIONS

Zhu et al., "Effects of inhibiting the lysine specific demethylase 1 enzyme activity in hepatitis B virus model mouse," Priority Disciplines Construction Project of Jiangsu Institutions of Higher Learning, vol. 33, No. 12, Dec. 2013, 5 pages.
Fang He et al., "Inhibition of hepatitis B Virus replication by hepatocyte nuclear factor 4-alpha specific short hairpin RNA," Liver International, Dec. 27, 2011, 10 pages.
Lang Bai et al., "Luteolin Inhibits Hepatitis B Virus Replication through Extracellular Signal-Regulated Kinase-Mediated Down-Regulation of Hepatocyte Nuclear Factor 4α Expression," Molecular Pharmaceutics, ACS Publications, Dec. 11, 2015, vol. 13, 568-577, 10 pages.
Chen Ji-yan, " Study on effect of carboxymethyl-pachymaran on anti-hepatitis virus in vivo and in vitro," Deprartment of Clinic, Ningxia Teachers College, 2015, 5 pages.
The International Preliminary Report on Patentability of PCT Appllication No. PCT/SG2016/050338 dated Jan. 16, 2018, 10 pages.
The Extended European Search Report of Patent Application No. 16824803.7 dated Oct. 19, 2018, 25 pages.
Communication Pursuant to Rules 70(2) and 70a(2) EPC of Patent Application No. 16824803.7 dated Nov. 7, 2018, 1 page.

\* cited by examiner

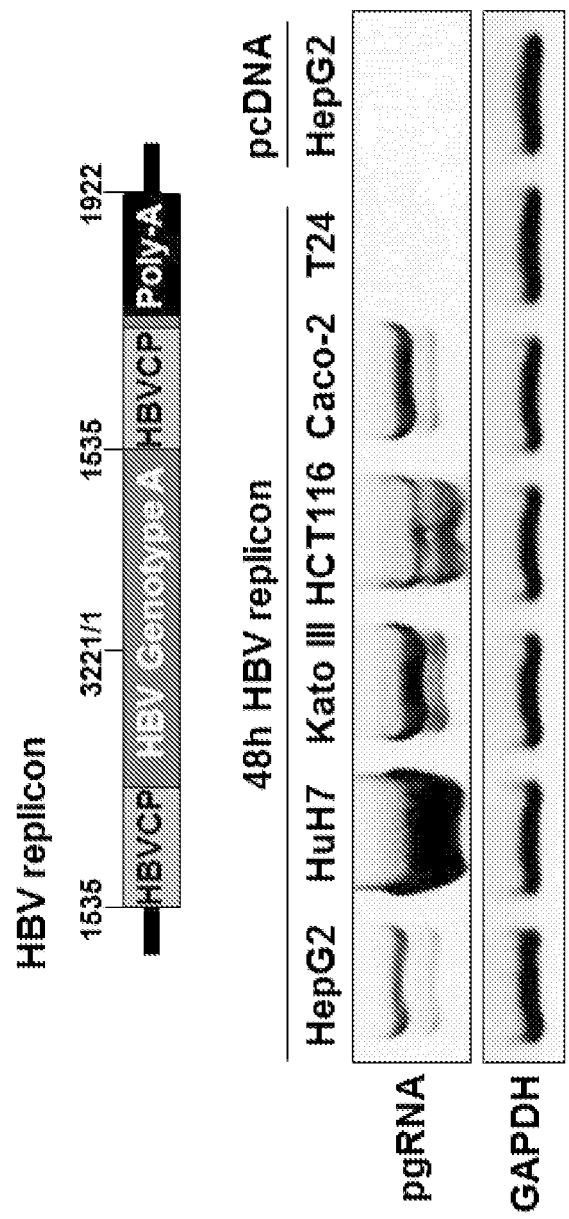

Fig. 6
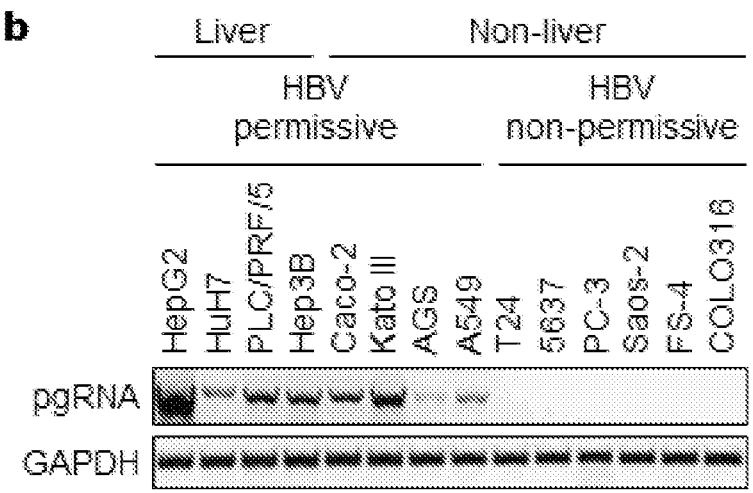
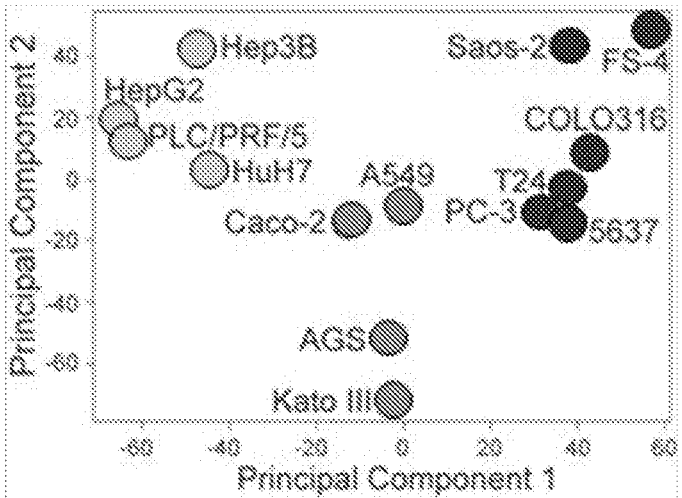

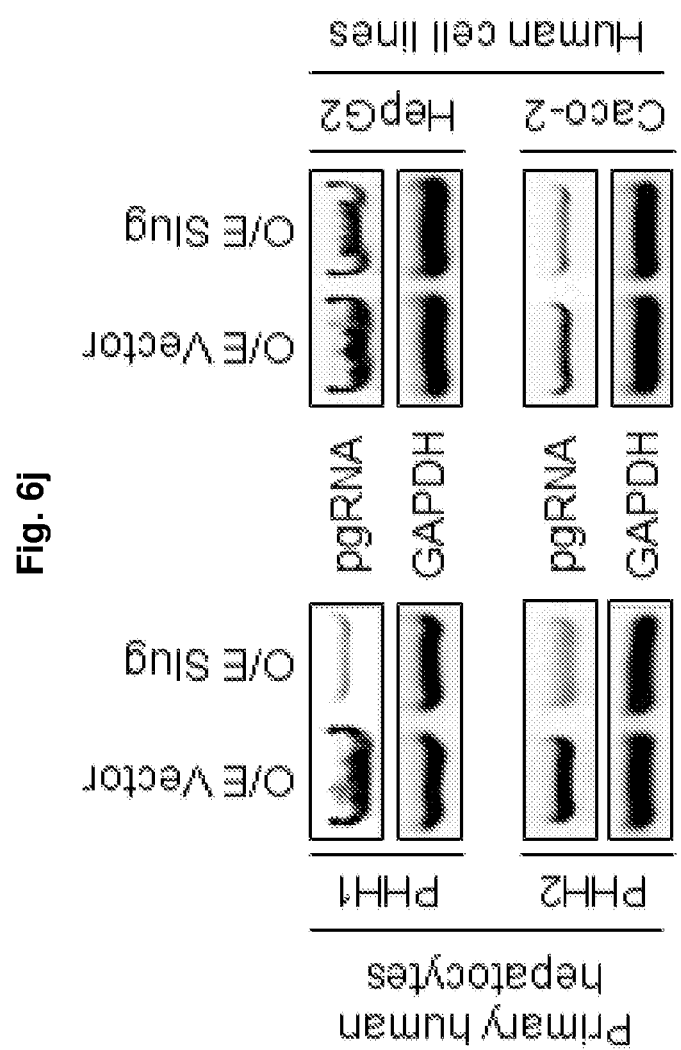

Fig. 18a

| | α-helix 1 | α-helix 2 | α-helix 3 | |
|---|---|---|---|---|
| | 51　　　　　　　64　　　　　　71　　　　　　85 88　　　　　　107 | | | |
| HMG-Box | | | | |
| Human Sox7 | IRRPMNAFMVWAKDERKRLAVQNPDLHNAELSKMLGKSWKALTLSQKRPYVDEAERLRLQHMQDYPNYK | | | (SEQ ID NO.: 236) |
| Rat Sox7    | ................................................................... | | | |
| Mouse Sox7  | ................................................................... | | | |
| Zebrafish Sox7 | .........................Q..................PP...E......V........ | | | |
| Human Sox17 | .........................Q...............AE..F.E......V....H...... | | | |
| Human Sox18 | ..........................V....A.E.NAAE..F.E......V..LR.H........ | | | |
| Human Sox4  | .K.........SQI.RRKIME.S..M...I..R..R..L.KD.D.IPFIR.....K..A...D... | | | |
| | .*..*******..;*;**...*  *  * *..**  * *;* ****;;;*.**.* | | | |

MODULATION OF HEPATITIS B VIRUS REPLICATION

CROSS-REFERENCE TO RELATED APPLICATIONS

This patent application is a U.S. National Phase Application under 35 U.S.C. § 371 of International Application No. PCT/SG2016/050338, filed on 15 Jul. 2016, entitled MODULATION OF HEPATITIS B VIRUS REPLICATION, which claims the benefit of priority of Singapore application No. 10201505551U, filed 15 Jul. 2015, the contents of which were incorporated by reference in the entirety for all purposes.

INCORPORATION BY REFERENCE

This patent application incorporates by reference the material (i.e., Sequence Listing) in the ASCII text file named sequence_listing_ST25_2153326_1.txt, created on Jan. 11, 2018, having a file size of 57,344 bytes, and the written sequence listing identified as sequence_listing_ST25 2153326 2, which is a PDF of an ASCII text file in computer readable form (CRF) named sequence_listing_ST25 2153326 2.txt, created Feb. 8, 2019, having a file size of 90,112 bytes.

FIELD OF THE INVENTION

The present invention relates to the field of virology, and more specifically the study of the underlying mechanism and factors involved in HBV replication. More specifically, the present invention relates to the identification of factors that modulate HBV replication for the subsequent development of agents that target these factors for use in in vitro methods or for treating HBV infection and associated diseases or conditions.

BACKGROUND OF THE INVENTION

Hepatitis B virus (HBV) affects 240 million chronic carriers globally and is linked to ~800,000 deaths annually from complications including liver cancer and cirrhosis.

Current HBV antiviral therapeutics target the late stage replicative phase by inhibiting viral polymerase/reverse transcriptase (Pol/RT) when viral load has risen significantly, limiting their effectiveness for viral clearance. Targeting early stage viral replication has not been feasible due to a lack of understanding of the precise host factors that drive viral replication.

Accordingly, there is a need to elucidate the fundamental molecular mechanism and associated factors underlying HBV replication. The identification of such factors will allow for the development of novel HBV intervention approaches as well as therapeutics for treating HBV infections and associated conditions or diseases.

SUMMARY

According to one aspect, there is provided a method of modulating HBV replication in a cell, comprising: contacting the cell with at least one agent that modulates the expression of at least one factor selected from the group consisting of SNAI2, SOX7, HNF4α1, HNF4α2, HNF4α3, HNF4α7, HNF4α8, HNF4α9, ARID3A, ATF2, ATF3, ATF4, CALCOCO1, CHD3, CPD, CSNK2A2, CNOT11, DCP1A, DDX39B, DYRK1B, E2F6, E2F7, EPAS1, FOXN2, HIVEP2, HERPUD1, KPNA3, KANK2, LIN54, LSD1, NCL, PAK1IP1, PNPT1, POLR3E, PRDX3, PTP4A1, RNASEH2A, RHOB, RNF4, RNF43, SERBP1, SKA1, SMAD3, SRPK1, STAM, STRADB, SSB, STT3B, TFAP2A, TFAP2C, TFB2M, TRIM24, TRIM68, TRIM27, WDR54 and ZNF518A.

In another aspect, there is provided a use of at least one agent in the manufacture of a medicament for treating a HBV infection in a subject, wherein the at least one agent modulates the activity of at least one factor selected from the group consisting of SNAI2, SOX7, HNF4α1, HNF4α2, HNF4α3, HNF4α7, HNF4α8, HNF4α9, ARID3A, ATF2, ATF3, ATF4, CALCOCO1, CHD3, CPD, CSNK2A2, CNOT11, DCP1A, DDX39B, DYRK1B, E2F6, E2F7, EPAS1, FOXN2, HIVEP2, HERPUD1, KPNA3, KANK2, LIN54, LSD1, NCL, PAK1IP1, PNPT1, POLR3E, PRDX3, PTP4A1, RNASEH2A, RHOB, RNF4, RNF43, SERBP1, SKA1, SMAD3, SRPK1, STAM, STRADB, SSB, STT3B, TFAP2A, TFAP2C, TFB2M, TRIM24, TRIM68, TRIM27, WDR54 and ZNF518A.

In another aspect, there is provided a use of at least one agent in the manufacture of a medicament for treating a disease or condition associated with a HBV infection in a subject, wherein the at least one agent modulates the activity of at least one factor selected from the group consisting of SNAI2, SOX7, HNF4α1, HNF4α2, HNF4α3, HNF4α7, HNF4α8, HNF4α9, ARID3A, ATF2, ATF3, ATF4, CALCOCO1, CHD3, CPD, CSNK2A2, CNOT11, DCP1A, DDX39B, DYRK1B, E2F6, E2F7, EPAS1, FOXN2, HIVEP2, HERPUD1, KPNA3, KANK2, LIN54, LSD1, NCL, PAK1IP1, PNPT1, POLR3E, PRDX3, PTP4A1, RNASEH2A, RHOB, RNF4, RNF43, SERBP1, SKA1, SMAD3, SRPK1, STAM, STRADB, SSB, STT3B, TFAP2A, TFAP2C, TFB2M, TRIM24, TRIM68, TRIM27, WDR54 and ZNF518A.

In another aspect, there is provided a method of treating a HBV infection in a subject, comprising administering to the subject of at least one agent that modulates the activity of at least one factor selected from the group consisting of SNAI2, SOX7, HNF4α1, HNF4α2, HNF4α3, HNF4α7, HNF4α8, HNF4α9, ARID3A, ATF2, ATF3, ATF4, CALCOCO1, CHD3, CPD, CSNK2A2, CNOT11, DCP1A, DDX39B, DYRK1B, E2F6, E2F7, EPAS1, FOXN2, HIVEP2, HERPUD1, KPNA3, KANK2, LIN54, LSD1, NCL, PAK1IP1, PNPT1, POLR3E, PRDX3, PTP4A1, RNASEH2A, RHOB, RNF4, RNF43, SERBP1, SKA1, SMAD3, SRPK1, STAM, STRADB, SSB, STT3B, TFAP2A, TFAP2C, TFB2M, TRIM24, TRIM68, TRIM27, WDR54 and ZNF518A.

In another aspect, there is provided a method for treating a disease or condition associated with a HBV infection in a subject, comprising administration to the subject of at least one agent that modulates the activity of at least one factor selected from the group consisting of SNAI2, SOX7, HNF4α1, HNF4α2, HNF4α3, HNF4α7, HNF4α8, HNF4α9, ARID3A, ATF2, ATF3, ATF4, CALCOCO1, CHD3, CPD, CSNK2A2, CNOT11, DCP1A, DDX39B, DYRK1B, E2F6, E2F7, EPAS1, FOXN2, HIVEP2, HERPUD1, KPNA3, KANK2, LIN54, LSD1, NCL, PAK1IP1, PNPT1, POLR3E, PRDX3, PTP4A1, RNASEH2A, RHOB, RNF4, RNF43, SERBP1, SKA1, SMAD3, SRPK1, STAM, STRADB, SSB, STT3B, TFAP2A, TFAP2C, TFB2M, TRIM24, TRIM68, TRIM27, WDR54 and ZNF518A.

In another aspect, there is provided a use of at least one peptide derived from SOX7 or SNAI2 in the manufacture of a medicament for inhibiting HBV replication or treating a HBV infection in a subject.

In another aspect, there is provided a method of screening at least one agent for modulating HBV replication, comprising; a) contacting a cell expressing the HBV virus with the at least one agent, wherein the at least one agent modulates the expression of at least one factor selected from the group consisting of SNAI2, SOX7, HNF4α1, HNF4α2, HNF4α3, HNF4α7, HNF4α8, HNF4α9, ARID3A, ATF2, ATF3, ATF4, CALCOCO1, CHD3, CPD, CSNK2A2, CNOT11, DCP1A, DDX39B, DYRK1B, E2F6, E2F7, EPAS1, FOXN2, HIVEP2, HERPUD1, KPNA3, KANK2, LIN54, LSD1, NCL, PAK1IP1, PNPT1, POLR3E, PRDX3, PTP4A1, RNASEH2A, RHOB, RNF4, RNF43, SERBP1, SKA1, SMAD3, SRPK1, STAM, STRADB, SSB, STT3B, TFAP2A, TFAP2C, TFB2M, TRIM24, TRIM68, TRIM27, WDR54 and ZNF518A; b) obtaining a HBV expression profile of the cell contacted with the at least one agent; and c) comparing the HBV expression profile of the cell in b) with an HBV expression profile of a control cell that has not been contacted with said at least one agent, wherein a decrease or increase in the expression of the HBV virus in the cell, relative to the control cell, indicates a modulation of HBV replication by said at least one agent.

In another aspect, there is provided a method of identifying at least one factor that modulates replication of a virus, comprising: a) transfecting at least two cell lines of different origins with an expression construct comprising a selection marker operably linked to a viral promoter of the virus; b) detecting the expression of the selection marker to classify the at least two cell lines into permissive and non-permissive cell lines; c) transfecting the permissive and non-permissive cell lines with an expression construct comprising a viral replicon of the virus; d) screening for expression of at least one factor in said permissive and non-permissive cell lines of c) and comparing the expression of the at least one factor in the permissive cell line to the non-permissive cell line, to identify at least one candidate factor, wherein the differential expression of the at least one factor between the permissive and non-permissive cell line is indicative of identifying at least one candidate factor; e) contacting said permissive cell line expressing the viral replicon with an agent to knock out expression of said at least one candidate factor; and f) comparing the pre-genomic RNA level of said viral replicon in said permissive cell line of e) relative to a control cell line that has not been contacted with said agent, wherein a decrease or increase in the expression level of the pre-genomic RNA level in the permissive cell line, relative to the control cell line, indicates the identification of at least one factor that modulates replication of the virus.

BRIEF DESCRIPTION OF THE DRAWINGS

The invention will be better understood with reference to the detailed description when considered in conjunction with the non-limiting examples and the accompanying drawings, in which:

FIG. 4. shows the efficacy of replicon transfection in various cell lines.

d) Luciferase assay for effect of Sox7 motif deletion on transcription at the HBVCP when Sox7 is overexpressed.

FIG. 16 shows combined effects of Slug and Sox7 on HBVCP inhibition. a) Overexpression of HNF4α isoforms alone does not increase HBVCP-dependent luciferase expression in non-permissive PC-3 cells; b) Transcription activation can be greatly enhanced in a HNF4α-dependent manner by Slug motif mutation together with increasing the spacer between HNF4α and Sox7 motifs in HBV non-permissive cell 5637. *Double mutant: HBVCP-Luc construct doubly mutated at the Slug motif and carrying the HNF4αN3Sox7 mutation.

FIG. 17 shows Slug mimetics. a) Multiple sequence alignments of Slug orthologues and human Slug family members for the five C2H2 zinc fingers (ZF1-5). As C2H2 zinc fingers bind DNA through residues −1, +2, +3 and +6 of the α-helix, these residues of predicted α-helical regions are highlighted. The variable Slug residue encoded by a functional SNP is highlighted; b) Effect of Slug motif deletion on HBVCP transcription repression in the presence of Slug mimetics Slug-ZF4s and Slug-ZF5s by luciferase reporter assay; c) Hydrocarbon stapling to preserve helicity and function of α-helical peptides derived from Slug zinc fingers 4 and 5 (Slug-ZF4n and Slug-ZF5n) achieved enhanced Slug mimetic function, resulting in further transcription inhibition at the HBVCP.

Figure 18B:
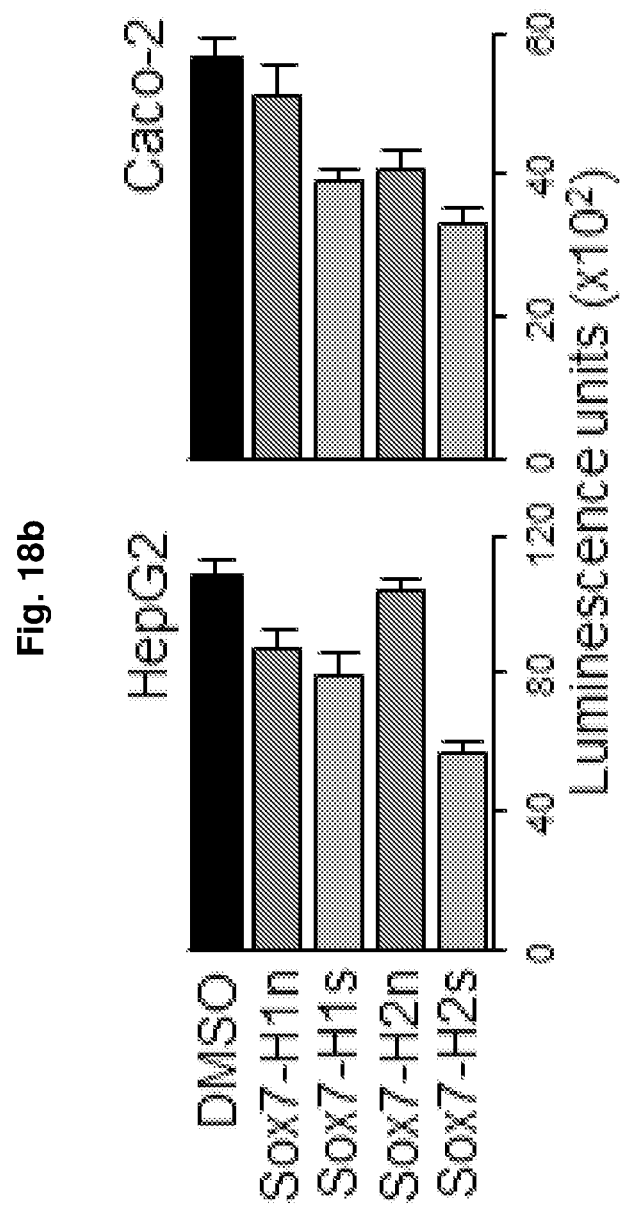

FIG. 18 shows Sox7 mimetics. a) Multiple sequence alignments of Sox7 orthologues and human Sox group F family members for the N-terminal DNA-binding HMG-Box. Residues of α-helical regions corresponding to DNA-binding residues in Sox17-DNA crystal structure are highlighted. As α-helix 3 only has 1 residue that interacts with DNA, its role in DNA-binding is negligible compared to α-helices 1 and 2; b) Hydrocarbon-stapled peptides (Sox7-H1s and Sox7-H2s) derived from Sox7 HMG-box helices 1 and 2 (Sox7-H1n and Sox7-H2n) show enhanced Sox7 mimetic function to further reduce transcription at the HBVCP; c) No difference in cell proliferation by WST-1 assay in HBV permissive cells treated with transcription factor mimetics compared with DMSO control.

DETAILED DESCRIPTION

Hepatitis B virus (HBV) is known mainly as a liver specific pathogen that causes chronic hepatitis infection and liver cancer. However, the present disclosure is based upon the discovery that HBV may replicate efficiently in a number of non-liver cells. Accordingly, this suggests that host cellular factors that are required for HBV propagation in liver cells may also be present in non-liver cells.

In particular, HBV is dependent on host transcription factors for pre-genomic RNA (pgRNA) synthesis at the HBV core promoter (HBVCP) (nt1600-1860) during its early replicative phase. These host factors may include but are not limited to Sp 1, PARP1 and HNF4α which are widely expressed in a variety of tissues, and hence cannot account for liver-specific replication of HBV.

Furthermore, since viral transmission may occur through exosomes, and clathrin-dependent endocytosis, it may be possible that HBV replication initiation is prohibited by mechanisms intrinsic to the infected non-liver cell. In particular, mechanisms blocking pgRNA synthesis may silence HBV replication as its loss would prevent the generation of the HBV DNA genome, viral polymerase/reverse transcriptase (Pol/RT) and capsid protein hepatitis B core antigen (HBcAg).

Accordingly, the present disclosure is based upon the further elucidation of the mechanism of HBV replication and transcription in identifying associated host factors required for HBV transcription and replication in various cells and/or tissues. The identification of such host factors will allow for the generation of new intervention approaches as well as the development of cell based screening methods which are critical for HBV therapeutic discovery.

In this regard, an advantage of the present disclosure is related to the identification of a number of factors that may influence or modulate the efficiency of HBV replication. In one embodiment, these factors may include but are not limited to transcriptional factors, signal pathway factors, protein binding factors and protein maturation factors.

In particular, the genes encoding these factors may be targeted to influence or modulate the efficiency of HBV replication. Exemplary, non-limiting embodiments of factors and associated gene targets that may influence the efficiency of HBV replication are listed in Table 1. All gene IDs listed in Table 1 are publicly disclosed in well-known gene or protein databases that may be referred to in obtaining further information on each gene ID, such as their sequence, location, family and function. These gene or protein databases may include but are not limited to the HUGO Gene Nomenclature Committee (HGNC), NCBI GeneBank or Uniprot.

TABLE 1

| GENE ID | Factor |
|---|---|
| SNAI2 | transcriptional factor |
| SOX7 | transcriptional factor |
| HNF4α1 | transcriptional factor |
| HNF4α2 | transcriptional factor |
| HNF4α3 | transcriptional factor |
| HNF4α7 | transcriptional factor |
| HNF4α8 | transcriptional factor |
| HNF4α9 | transcriptional factor |
| ARID3A | transcriptional factor |
| ATF2 | transcriptional factor |
| ATF3 | transcriptional factor |
| ATF4 | transcriptional factor |
| CALCOCO1 | transcriptional factor |
| CHD3 | transcriptional factor |
| CPD | signal pathway factor |
| CSNK2A2 | signal pathway factor |
| CNOT11 | transcriptional factor |
| DCP1A | transcriptional factor |
| DDX39B | transcriptional factor |
| DYRK1B | transcriptional factor |
| E2F6 | transcriptional factor |
| E2F7 | transcriptional factor |
| EPAS1 | transcriptional factor |
| FOXN2 | transcriptional factor |
| HIVEP2 | transcriptional factor |
| HERPUD1 | signal pathway factor |
| KPNA3 | signal pathway factor |
| KANK2 | transcriptional factor |
| LIN54 | transcriptional factor |
| LSD1 | transcriptional factor |
| NCL | transcriptional factor |
| PAK1IP1 | signal pathway factor |
| PNPT1 | transcriptional factor |
| POLR3E | transcriptional factor |
| PRDX3 | signal pathway factor |
| PTP4A1 | signal pathway factor |
| RNASEH2A | transcriptional factor |
| RHOB | signal pathway factor |
| RNF4 | transcriptional factor |
| RNF43 | signal pathway factor |
| SERBP1 | transcriptional factor |
| SKA1 | transcriptional factor |
| SMAD3 | transcriptional factor |
| SRPK1 | signal pathway factor |
| STAM | transcriptional factor |
| STRADB | signal pathway factor |
| SSB | transcriptional factor |
| STT3B | signal pathway factor |
| TFAP2A | transcriptional factor |
| TFAP2C | transcriptional factor |
| TP73 | transcriptional factor |
| TFB2M | transcriptional factor |
| TRIM24 | transcriptional factor |
| TRIM68 | transcriptional factor |
| TRIM27 | transcriptional factor |
| WDR54 | transcriptional factor |
| ZNF518A | transcriptional factor |
| C1orf131 | transcriptional factor |
| ETS1 | transcriptional factor |
| FSTL1 | transcriptional factor |
| INHBA | transcriptional factor |
| KCTD12 | transcriptional factor |
| MAK16 | transcriptional factor |
| NOSTRIN | transcriptional factor |
| PTCD3 | transcriptional factor |
| SEMA4G | transcriptional factor |
| SNRPD1 | transcriptional factor |

TABLE 1-continued

| GENE ID | Factor |
| --- | --- |
| SUSD1 | transcriptional factor |
| WDR43 | transcriptional factor |
| ZFHX4 | transcriptional factor |
| ALDH2 | signal pathway factor |
| ALDH5A1 | signal pathway factor |
| B3GNT2 | signal pathway factor |
| CHUK | signal pathway factor |
| DDX18 | signal pathway factor |
| EPT1 | signal pathway factor |
| ERMP1 | signal pathway factor |
| GCNT3 | signal pathway factor |
| GSR | signal pathway factor |
| HMGCS1 | signal pathway factor |
| NAE1 | signal pathway factor |
| PDSS1 | signal pathway factor |
| PPID | signal pathway factor |
| SMURF2 | signal pathway factor |
| TANC2 | signal pathway factor |
| BCAR3 | signal pathway factor |
| C16orf70 | signal pathway factor |
| C9orf100 | signal pathway factor |
| EPB41L5 | signal pathway factor |
| HSPA14 | signal pathway factor |
| HSPA9 | signal pathway factor |
| LRP12 | signal pathway factor |
| NSMCE4A | signal pathway factor |
| NUP35 | signal pathway factor |
| PSMD11 | signal pathway factor |
| EXOC6 | signal pathway factor |
| FUZ | signal pathway factor |
| STOML2 | signal pathway factor |
| WASF2 | signal pathway factor |
| ARHGAP12 | signal pathway factor |
| MYO9B | signal pathway factor |
| TBC1D14 | signal pathway factor |
| FLVCR1 | signal pathway factor |
| SLC39A14 | signal pathway factor |
| GPX2 | signal pathway factor |
| IDH1 | signal pathway factor |
| FAM35A | Unknown |

In one embodiment there is provided a method of modulating HBV replication in a cell. In particular, the method comprises contacting the cell with at least one agent that modulates the expression of at least one factor selected from the group consisting of SNAI2, SOX7, HNF4α1, HNF4α2, HNF4α3, HNF4α7, HNF4α8, HNF4α9, ARID3A, ATF2, ATF3, ATF4, CALCOCO1, CHD3, CPD, CSNK2A2, CNOT11, DCP1A, DDX39B, DYRK1B, E2F6, E2F7, EPAS1, FOXN2, HIVEP2, HERPUD1, KPNA3, KANK2, LIN54, LSD1, NCL, PAK1IP1, PNPT1, POLR3E, PRDX3, PTP4A1, RNASEH2A, RHOB, RNF4, RNF43, SERBP1, SKA1, SMAD3, SRPK1, STAM, STRADB, SSB, STT3B, TFAP2A, TFAP2C, TFB2M, TRIM24, TRIM68, TRIM27, WDR54 and ZNF518A.

In an alternative embodiment the cell may be contacted with at least one agent that modulates the expression of at least one factor selected from the group consisting of C1orf131, ETS1, FSTL1, HNF4A, INHBA, KCTD12, MAK16, NOSTRIN, PNPT1, PTCD3, SEMA4G, SNAI2, SNRPD1, SUSD1, WDR43, ZFHX4, ALDH2, ALDH5A1, B3GNT2, CHUK, DDX18, EPT1, ERMP1, GCNT3, GSR, HMGCS1, NAE1, PDSS1, PPID, SMURF2, TANC2, BCAR3, C16orf70, C9orf100, EPB41L5, HSPA14, HSPA9, LRP12, NSMCE4A, NUP35, PSMD11, RNF43, EXOC6, FUZ, STOML2, WASF2, ARHGAP12, MYO9B, TBC1D14, FLVCR1, SLC39A14, GPX2, IDH1 and FAM35A.

In one embodiment, the HBV replication in the cell may be inhibited. In some embodiments, the at least one agent may be selected from the group consisting of a chemical compound, a small molecule, an oligonucleotide, a protein, a peptide, a stapled peptide, a peptidomimetic, an antibody and an antigen binding molecule. The oligonucleotide may be a siRNA or a shRNA.

The at least one factor may be selected from the group consisting of SNAI2, SOX7, HNF4α1, HNF4α2, HNF4α3, HNF4α7, HNF4α8 and HNF4α9. In one embodiment, the at least one factor may be SNAI2 or SOX7.

In one embodiment, the at least one agent may be a siRNA. In one embodiment, the siRNA decreases the expression of SNAI2 or SOX7 in the cell such that HBV replication in the cell is increased relative to the HBV replication in the cell in the absence of the siRNA. In another embodiment, the siRNA decreases the expression of HNF4α1, HNF4α2, HNF4α3, HNF4α7, HNF4α8 or HNF4α9 such that HBV replication in the cell is decreased relative to the HBV replication in the cell in the absence of the siRNA.

In some embodiments, the cell may be selected from the group consisting of a liver cell, colon cell, stomach cell, blood cell and lung cell.

In one embodiment, the method may be performed in vitro.

In some embodiments, the cell may be derived from a cell line selected from the group consisting of HepG2, HuH6, HuH7, HuH4, PLC/PRF/5, Kato III, AGS, HCT116, Caco-2, HL-60, HEK293 and A549.

In the method as described herein the contacting step may comprise culturing the cell in the presence of the at least one agent.

The present disclosure also provides the use of at least one agent in the manufacture of a medicament for treating a HBV infection in a subject, wherein the at least one agent modulates the activity of at least one factor selected from the group consisting of SNAI2, SOX7, HNF4α1, HNF4α2, HNF4α3, HNF4α7, HNF4α8, HNF4α9, ARID3A, ATF2, ATF3, ATF4, CALCOCO1, CHD3, CPD, CSNK2A2, CNOT11, DCP1A, DDX39B, DYRK1B, E2F6, E2F7, EPAS1, FOXN2, HIVEP2, HERPUD1, KPNA3, KANK2, LIN54, LSD1, NCL, PAK1IP1, PNPT1, POLR3E, PRDX3, PTP4A1, RNASEH2A, RHOB, RNF4, RNF43, SERBP1, SKA1, SMAD3, SRPK1, STAM, STRADB, SSB, STT3B, TFAP2A, TFAP2C, TFB2M, TRIM24, TRIM68, TRIM27, WDR54 and ZNF518A.

The present disclosure also provides the use of at least one agent in the manufacture of a medicament for treating a disease or condition associated with a HBV infection in a subject, wherein the at least one agent modulates the activity of at least one factor selected from the group consisting of SNAI2, SOX7, HNF4α1, HNF4α2, HNF4α3, HNF4α7, HNF4α8, HNF4α9, ARID3A, ATF2, ATF3, ATF4, CALCOCO1, CHD3, CPD, CSNK2A2, CNOT11, DCP1A, DDX39B, DYRK1B, E2F6, E2F7, EPAS1, FOXN2, HIVEP2, HERPUD1, KPNA3, KANK2, LIN54, LSD1, NCL, PAK1IP1, PNPT1, POLR3E, PRDX3, PTP4A1, RNASEH2A, RHOB, RNF4, RNF43, SERBP1, SKA1, SMAD3, SRPK1, STAM, STRADB, SSB, STT3B, TFAP2A, TFAP2C, TFB2M, TRIM24, TRIM68, TRIM27, WDR54 and ZNF518A.

In some embodiments, the disease or condition may be liver disease. In another embodiment, the disease, disorder or condition is jaundice, liver inflammation, liver fibrosis, inflammation, liver cirrhosis, liver failure, diffuse hepatocellular inflammatory disease, hemophagocytic syndrome, serum hepatitis, HBV viremia, liver steatosis, hepatocellular carcinoma, liver disease-related transplantation, glomerulonephritis, dyslipidemia, hematopoietic malignancies or pancreatitis.

In one embodiment, the at least one agent inhibits HBV replication. In some embodiments, the at least one agent may be selected from the group consisting of a chemical compound, a small molecule, an oligonucleotide, a protein, a peptide, a stapled peptide, a peptidomimetic, an antibody and an antigen binding molecule. The oligonucleotide may be a siRNA or shRNA.

In some embodiments, the at least one factor may be selected from the group consisting of SNAI2, SOX7, HNF4α1, HNF4α2, HNF4α3, HNF4α7, HNF4α8 and HNF4α9. In one embodiment, the at least one factor may be SNAI2 or SOX7.

The present disclosure also provides the use of at least one peptide derived from SOX7 or SNAI2 in the manufacture of a medicament for inhibiting HBV replication or treating a HBV infection in a subject. In another embodiment, the at least one peptide may be derived from any one of the factors disclosed herein.

In one embodiment, the at least one peptide described herein may include a peptide analogue, modified peptide or peptide derivative of the native protein encoded by SOX7 or SNAI2. Analogues or functional equivalents of the native protein may be a peptidic molecule that retains the activity and function of the native protein, and may, for instance be a peptidomimetic. A peptide derivative or variant may be a peptide identical to the reference protein or peptide sequence, that is be 100% identical, or it may include up to a certain integer number of amino acid alterations as compared to the reference sequence such that the % identity is less than 100%, such as at least 50, 60, 70, 75, 80, 85, 90, 95, 98, or 99% identical. Such alterations are selected from the group consisting of at least one amino acid deletion, substitution, including conservative and non-conservative substitution, or insertion. Modified peptides may be molecules derived from a peptide or protein by the introduction of substituents or functional groups which are, generally, not present in naturally occurring amino acids. A peptidomimetic or peptide mimic, may include synthetic compounds with a functional structure more or less similar to a reference peptide or protein, but which may also contain non-peptidic bonds in the backbone, or D-amino acids. In general, peptidomimetics may serve as substitutes for native proteins in being designed to mimic the function and activity of the protein. An example of a peptide mimic may include but is not limited to a stapled peptide that is a peptide comprising a synthetic brace ("staple") such as a hydrocarbon staple.

In one embodiment, the at least one peptide may be derived from DNA binding domains of the native protein encoded by SOX7 or SNAI2. Accordingly, in one embodiment, the at least one peptide may be derived from a peptide selected from the group consisting of Slug-ZF1s (SEQ ID NO: 215); Slug-ZF2s (SEQ ID NO: 216); Slug-ZF3s (SEQ ID NO: 217); Slug-ZF4s (SEQ ID NO: 218); Slug-ZF5s (SEQ ID NO: 219) Sox7-H1s (SEQ ID NO: 220); and Sox7-H2s (SEQ ID NO: 221).

In one embodiment, the at least one peptide may be derived from a peptide selected from the group consisting of Slug-ZF4s (SEQ ID NO: 218); Slug-ZF5s (SEQ ID NO: 219), Sox7-H1s (SEQ ID NO: 220); and Sox7-H2s (SEQ ID NO: 221).

In one embodiment, the at least one peptide may be a stapled peptide. In another embodiment, the stapled peptide may comprise a hydrocarbon staple.

In one embodiment, the at least one peptide may be formulated as a composition suitable for a convenient mode of administration to the subject. In one embodiment, the at least one peptide may be formulated as a pharmaceutical composition comprising a pharmaceutically acceptable carrier.

The present disclosure also provides a method for inhibiting HBV replication or treating a HBV infection in a subject, comprising administering to the subject at least one peptide derived from SOX7 or SNAI2.

In one embodiment, the at least one peptide may be derived from a peptide selected from the group consisting of Slug-ZF1s (SEQ ID NO: 215); Slug-ZF2s (SEQ ID NO: 216); Slug-ZF3s (SEQ ID NO: 217); Slug-ZF4s (SEQ ID NO: 218); Slug-ZF5s (SEQ ID NO: 219) Sox7-H1s (SEQ ID NO: 220); and Sox7-H2s (SEQ ID NO: 221).

In one embodiment, the at least one peptide may be derived from a peptide selected from the group consisting of Slug-ZF4s (SEQ ID NO: 218); Slug-ZF5s (SEQ ID NO: 219), Sox7-H1s (SEQ ID NO: 220); and Sox7-H2s (SEQ ID NO: 221).

In one embodiment, the at least one peptide may be a stapled peptide. In another embodiment, the stapled peptide may comprise a hydrocarbon staple.

The sequence, structure and location of the hydrocarbon staple may be varied for functionality and synthesized using well-known techniques in the art or obtained from commercial companies such as GenScript. As may be appreciated by those skilled in the art, the sequence, structure and location of the hydrocarbon staple may vary as long as it does not disrupt the interaction of the peptide comprising the hydrocarbon staple with a nucleic acid, for example DNA.

In particular, the hydrocarbon staple may attach 2 amino acid residues within each peptide at specific residue positions. The residue positions as described herein may correspond to the residue positions within the amino acid sequence of the full-length native protein. For example, the residue position for the first hydrocarbon attachment may be denoted as "i", and the subsequent second hydrocarbon attachment may be positioned at least 2 or more amino acid residues from "i". In one embodiment, the hydrocarbon staple may be attached at residue positions "i" and "i+4" or "i" and "i+7", wherein the +4 or +7 denotes the number of amino acid positions from "i" that the second hydrocarbon attachment is positioned.

As readily known in the technical field, once a peptide is stapled with a hydrocarbon staple, the original amino acid at the attachment positions may be replaced by a non-natural amino acid. The non-natural amino acid may include but is not limited to S-pentenylalanine, S-octenylalanine, R-octenylalanine or R-pentenylalanine. In one embodiment, the hydrocarbon staple may be attached at residue positions "i" and "i+4", wherein the amino acids at both "i" and "i+4" positions may be S-pentenylalanine. In another embodiment, the hydrocarbon staple may be attached at residue positions "i" and "i+7", wherein the amino acids at both "i" and "i+7" positions may be selected from R-octenylalanine, S-pentenylalanine, S-octenylalanine or R-pentenylalanine. In particular, the amino acid at position "i" may be R-octenylalanine or S-octenylalanine and the amino acid at position "i+7" may be S-pentenylalanine or R-pentenylalanine.

Figure 9A:
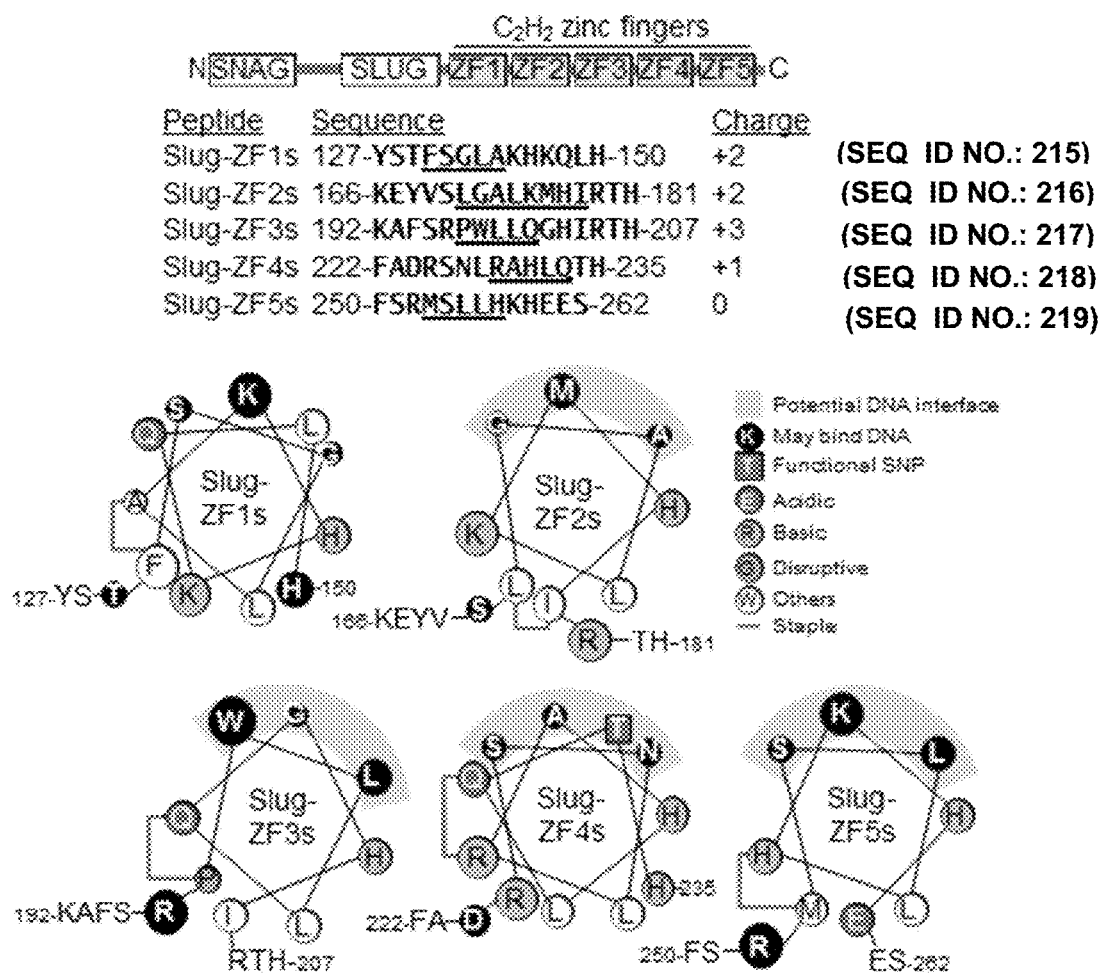
FIG. 9 shows that Slug and Sox7 transcription factor mimetics arrest HBV replication. a) Schematic of Slug functional domains. Slug has five C2H2 zinc fingers (ZF1-5), each may bind DNA. Potential DNA binding residues are indicated, site of hydrocarbon staples are underlined. Helical wheel diagrams show the predicted DNA binding interface of each peptide; b) Identification of functional Slug mimetics by comparing $IC_{50}$ using HBVCP-Luc reporter assay; c) Sustenance of transcription inhibition by Slug mimetics at HBVCP when compared to DMSO control and Slug overexpression; d) Schematic of Sox7 functional domains showing the DNA-binding HMG-box containing 3 α-helices (H1-H3). Only H1 and H2 are predicted to bind DNA strongly. DNA binding residues are indicated, site of hydrocarbon staples are underlined. Helical wheel diagrams show the predicted DNA binding interface of each mimetic; e) Dose-curves for Sox7 mimetics to determine $IC_{50}$ using HBVCP-Luc reporter assay; f) Sox7-H1s and Sox7-H2s mimicked Sox7 function by inhibiting HBVCP transcription activity when compared to negligible effect with DMSO control; g) Effect of mimetic combinations on HBVCP transcription inhibition using HBVCP-Luc reporter assay; h) Effect of Slug and Sox7 mimetics on pgRNA in cells transfected with HBV replicon 24 hours prior to peptide addition.

In one embodiment, the stapled peptide may comprise a hydrocarbon staple that is attached in Slug zinc fingers (ZF) at the following locations of ZF1s (Zinc Finger 1 stapled) at F130 and A134, ZF2s (Zinc Finger 2 stapled) at L171 and I178, ZF3s (Zinc Finger 3 stapled) at P197 and Q201, ZF4s (Zinc Finger 4 stapled) at R229 and Q233 or ZF5s (Zinc Finger 5 stapled) at M253 and H257 (FIG. 9a).

Figure 9B:
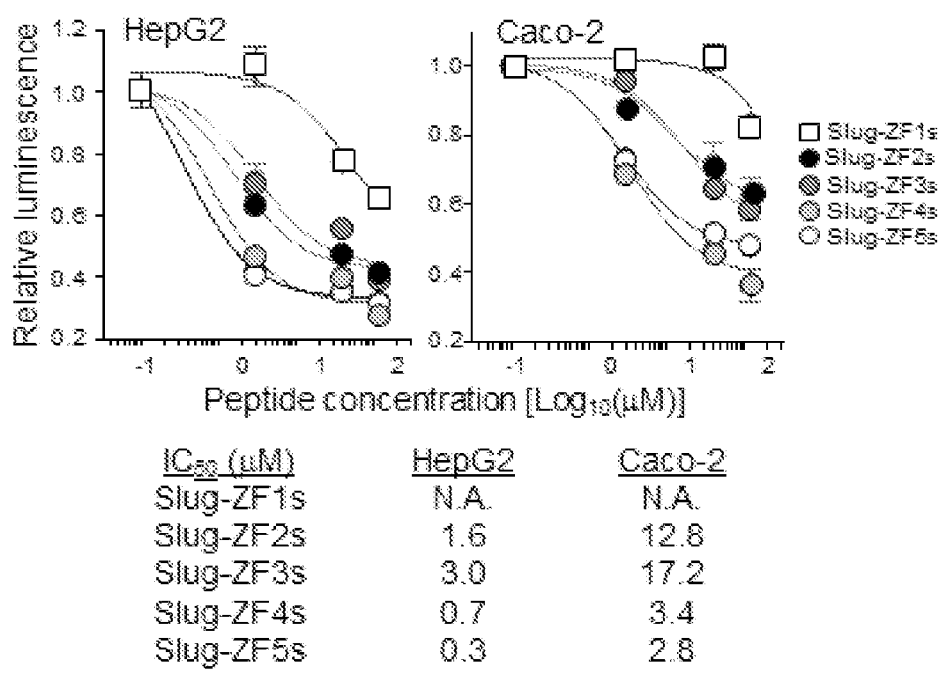
Figure 9C:
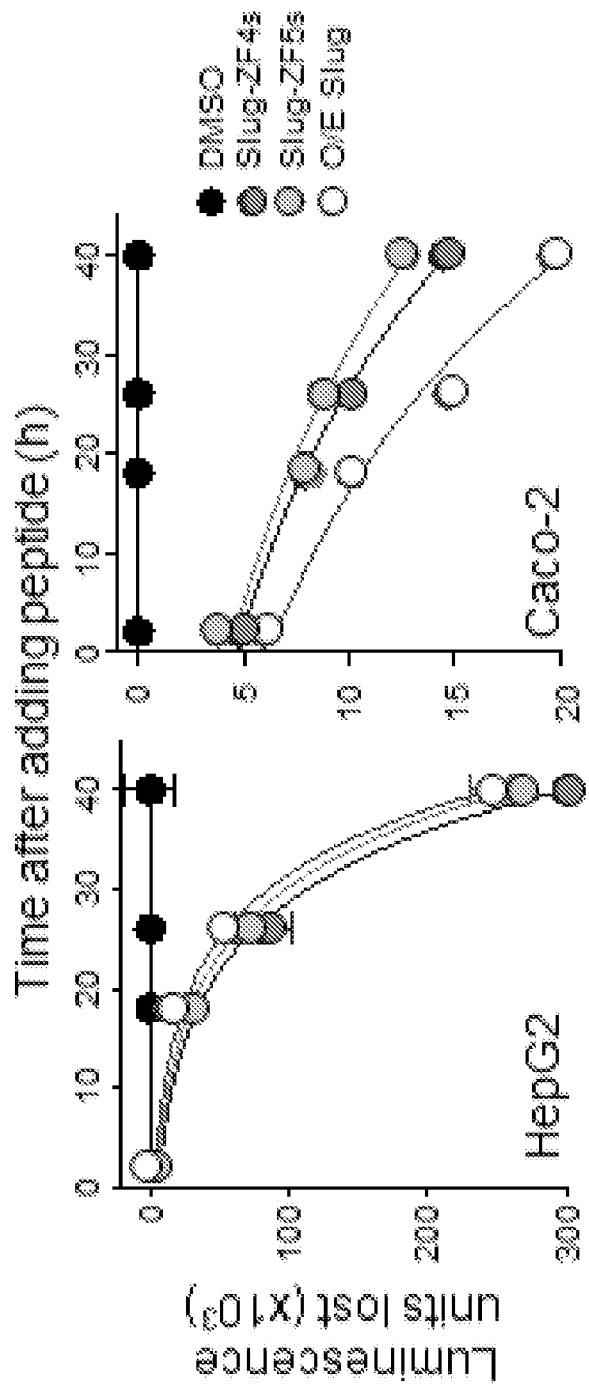
Figure 9D:
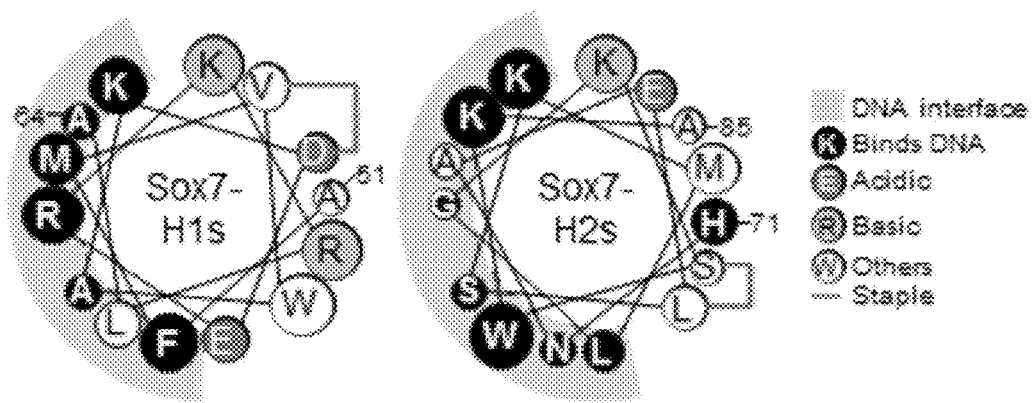

In one embodiment, the stapled peptide may comprise a hydrocarbon staple that is attached in Sox7 helices (H) at the following locations of H1 s (Helix 1 stapled) at V54 and D58 or H2s (Helix 2 stapled) at L75 and S82 (FIG. 9d).

In one embodiment, the at least one peptide may be formulated as a composition suitable for a convenient mode of administration to the subject. In one embodiment, the at least one peptide may be formulated as a pharmaceutical composition comprising a pharmaceutically acceptable carrier. In one embodiment, the at least one peptide may be formulated as a composition suitable for administration by injection. In another embodiment, the at least one peptide may be incorporated into a nanoparticle complex for a suitable mode of administration.

The present disclosure also provides a method of treating a HBV infection in a subject, comprising administering to the subject at least one agent that modulates the activity of at least one factor selected from the group consisting of SNAI2, SOX7, HNF4α1, HNF4α2, HNF4α3, HNF4α7, HNF4α8, HNF4α9, ARID3A, ATF2, ATF3, ATF4, CALCOCO1, CHD3, CPD, CSNK2A2, CNOT11, DCP1A, DDX39B, DYRK1B, E2F6, E2F7, EPAS1, FOXN2, HIVEP2, HERPUD1, KPNA3, KANK2, LIN54, LSD1, NCL, PAK1IP1, PNPT1, POLR3E, PRDX3, PTP4A1, RNASEH2A, RHOB, RNF4, RNF43, SERBP1, SKA1, SMAD3, SRPK1, STAM, STRADB, SSB, STT3B, TFAP2A, TFAP2C, TFB2M, TRIM24, TRIM68, TRIM27, WDR54 and ZNF518A.

The present disclosure also provides a method for treating a disease or condition associated with a HBV infection in a subject, comprising administration to the subject of at least one agent that modulates the activity of at least one factor selected from the group consisting of SNAI2, SOX7, HNF4α1, HNF4α2, HNF4α3, HNF4α7, HNF4α8, HNF4α9, ARID3A, ATF2, ATF3, ATF4, CALCOCO1, CHD3, CPD, CSNK2A2, CNOT11, DCP1A, DDX39B, DYRK1B, E2F6, E2F7, EPAS1, FOXN2, HIVEP2, HERPUD1, KPNA3, KANK2, LIN54, LSD1, NCL, PAK1IP1, PNPT1, POLR3E, PRDX3, PTP4A1, RNASEH2A, RHOB, RNF4, RNF43, SERBP1, SKA1, SMAD3, SRPK1, STAM, STRADB, SSB, STT3B, TFAP2A, TFAP2C, TFB2M, TRIM24, TRIM68, TRIM27, WDR54 and ZNF518A.

In some embodiments, the disease or condition may be liver disease. In another embodiment, the disease, disorder or condition is jaundice, liver inflammation, liver fibrosis, inflammation, liver cirrhosis, liver failure, diffuse hepatocellular inflammatory disease, hemophagocytic syndrome, serum hepatitis, HBV viremia, liver steatosis, hepatocellular carcinoma, liver disease-related transplantation, glomerulonephritis, dyslipidemia, hematopoietic malignancies or pancreatitis.

In one embodiment, the at least one agent inhibits HBV replication. In some embodiments, the at least one agent may be selected from the group consisting of a chemical compound, a small molecule, an oligonucleotide, a protein, a peptide, a stapled peptide, a peptidomimetic, an antibody and an antigen binding molecule.

The oligonucleotide may be a siRNA or shRNA. In some embodiments, the at least one factor may be selected from the group consisting of SNAI2, SOX7, HNF4α1, HNF4α2, HNF4α3, HNF4α7, HNF4α8 and HNF4α9. In one embodiment, the at least one factor may be SNAI2 or SOX7.

In the context of this disclosure, the term "administering" and variations of that term including "administer" and "administration", includes contacting, applying, delivering or providing a an agent, peptide, compound or composition as described herein to an organism, or a surface by any appropriate means. Convenient modes of administration may include injection (subcutaneous, intravenous, and the like), oral administration, inhalation, transdermal application, topical creams or gels or powders, or rectal administration. Depending on the route of administration, the agent may be coated with a material to protect the compound from the action of enzymes, acids and other natural conditions which may inactivate the therapeutic activity of the compound. The agent may also be administered parenterally or intraperitoneally.

Dispersions of the agent, peptide, compound or composition as described herein may also be prepared in glycerol, liquid polyethylene glycols, and mixtures thereof and in oils. Under ordinary conditions of storage and use, pharmaceutical preparations may contain a preservative to prevent the growth of microorganisms.

Pharmaceutical compositions suitable for injection include sterile aqueous solutions (where water soluble) or dispersions and sterile powders for the extemporaneous preparation of sterile injectable solutions or dispersions. Ideally, the composition is stable under the conditions of manufacture and storage and may include a preservative to stabilise the composition against the contaminating action of microorganisms such as bacteria and fungi.

In one embodiment, an agent, peptide, compound or composition as described herein may be administered orally, for example, with an inert diluent or an assimilable edible carrier. The agent, peptide, compound or composition may be incorporated into a nanoparticle complex. Alternatively, the agent, peptide, compound or composition as described herein and other ingredients may also be enclosed in a hard or soft shell gelatin capsule, compressed into tablets, or incorporated directly into an individual's diet. For oral therapeutic administration, the agent, peptide, compound or composition as described herein may be incorporated with excipients and used in the form of ingestible tablets, buccal tablets, troches, capsules, elixirs, suspensions, syrups, wafers, and the like. Suitably, such compositions and preparations may contain at least 1% by weight of the agent. The percentage of the compound(s) of formula (I) and/or (II) in pharmaceutical compositions and preparations may, of course, be varied and, for example, may conveniently range from about 2% to about 90%, about 5% to about 80%, about 10% to about 75%, about 15% to about 65%; about 20% to about 60%, about 25% to about 50%, about 30% to about 45%, or about 35% to about 45%, of the weight of the dosage unit. The amount of compound in therapeutically useful compositions is such that a suitable dosage will be obtained.

The language "pharmaceutically acceptable carrier" is intended to include solvents, dispersion media, coatings, anti-bacterial and anti-fungal agents, isotonic and absorption delaying agents, and the like. The use of such media and agents for pharmaceutically active substances is well known in the art. Except insofar as any conventional media or agent is incompatible with the compound, use thereof in the therapeutic compositions and methods of treatment and prophylaxis is contemplated. Supplementary active compounds may also be incorporated into the compositions according to the present disclosure. It is especially advantageous to formulate parenteral compositions in dosage unit form for ease of administration and uniformity of dosage. "Dosage unit form" as used herein refers to physically discrete units suited as unitary dosages for the individual to be treated; each unit containing a predetermined quantity of an agent, peptide, compound or composition as described herein is calculated to produce the desired therapeutic effect in association with the required pharmaceutical carrier. The agent, peptide, compound or composition as described herein may be formulated for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients. In one embodiment, the carrier may be an orally administrable carrier.

Another form of a pharmaceutical composition is a dosage form formulated as enterically coated granules, tablets or capsules suitable for oral administration. Also included in the scope of this invention are delayed release formulations.

An agent, peptide, compound or composition as described herein may also be administered in the form of a "prodrug". A prodrug is an inactive form of a compound which is transformed in vivo to the active form.

In one embodiment, the agent, peptide, compound or composition as described herein may be administered by injection. In the case of injectable solutions, the carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by including various anti-bacterial and/or anti-fungal agents. Suitable anti-bacterial and/or anti-fungal agents are well known to those skilled in the art and include, for example, parabens, chlorobutanol, phenol, benzyl alcohol, ascorbic acid, thimerosal, and the like. In many cases, it may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminium monostearate and gelatin.

Sterile injectable solutions can be prepared by incorporating the agent, peptide, compound or composition as described herein in the required amount in an appropriate solvent with one or a combination of ingredients enumerated above, as required, followed by filtered sterilisation. Generally, dispersions are prepared by incorporating the agent, peptide, compound or composition as described herein into a sterile vehicle which contains a basic dispersion medium and the required other ingredients from those enumerated above.

Tablets, troches, pills, capsules and the like can also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavouring agent such as peppermint, oil of wintergreen, or cherry flavouring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the analogue, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the analogue can be incorporated into sustained-release preparations and formulations.

Preferably, the pharmaceutical composition may further include a suitable buffer to minimise acid hydrolysis. Suitable buffer agent agents are well known to those skilled in the art and include, but are not limited to, phosphates, citrates, carbonates and mixtures thereof.

Single or multiple administrations of the agent, peptide, compound or composition as described herein may be carried out. One skilled in the art would be able, by routine experimentation, to determine effective, non-toxic dosage levels of the agent according to the disclosure and an administration pattern which would be suitable for treating the diseases and/or infections to which the agent, peptide, compound or composition as described herein is applicable.

Further, it will be apparent to one of ordinary skill in the art that the optimal course of treatment, such as the number of doses of the agent, peptide, compound or composition as described herein given per day for a defined number of days, can be ascertained using convention course of treatment determination tests.

Generally, an effective dosage per 24 hours may be in the range of about 0.0001 mg to about 1000 mg per kg body weight; suitably, about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. More suitably, an effective dosage per 24 hours may be in the range of about 1.0 mg to about 200 mg per kg body weight; about 1.0 mg to about 100 mg per kg body weight; about 1.0 mg to about 50 mg per kg body weight; about 1.0 mg to about 25 mg per kg body weight; about 5.0 mg to about 50 mg per kg body weight; about 5.0 mg to about 20 mg per kg body weight; or about 5.0 mg to about 15 mg per kg body weight.

Alternatively, an effective dosage may be up to about 500 mg/m$^2$. For example, generally, an effective dosage is expected to be in the range of about 25 to about 500 mg/m$^2$, about 25 to about 350 mg/m$^2$, about 25 to about 300 mg/m$^2$, about 25 to about 250 mg/m$^2$, about 50 to about 250 mg/m$^2$, and about 75 to about 150 mg/m$^2$.

There is also provided a method of screening at least one agent for modulating HBV replication. The method comprises a) contacting a cell expressing the HBV virus with the at least one agent, wherein the at least one agent modulates the expression of at least one factor selected from the group consisting of SNAI2, SOX7, HNF4α1, HNF4α2, HNF4α3, HNF4α7, HNF4α8, HNF4α9, ARID3A, ATF2, ATF3, ATF4, CALCOCO1, CHD3, CPD, CSNK2A2, CNOT11, DCP1A, DDX39B, DYRK1B, E2F6, E2F7, EPAS1, FOXN2, HIVEP2, HERPUD1, KPNA3, KANK2, LIN54, LSD1, NCL, PAK1IP1, PNPT1, POLR3E, PRDX3, PTP4A1, RNASEH2A, RHOB, RNF4, RNF43, SERBP1, SKA1, SMAD3, SRPK1, STAM, STRADB, SSB, STT3B, TFAP2A, TFAP2C, TFB2M, TRIM24, TRIM68, TRIM27, WDR54 and ZNF518A; b) obtaining a HBV expression profile of the cell contacted with the at least one agent; and c) comparing the HBV expression profile of the cell in b) with an HBV expression profile of a control cell that has not been contacted with said at least one agent, wherein a decrease or increase in the expression of the HBV virus in the cell, relative to the control cell, indicates a modulation of HBV replication by said at least one agent.

In one embodiment, the at least one agent may be selected from the group consisting of a chemical compound, a small molecule, a oligonucleotide, a protein, a peptide, a stapled peptide, a peptidomimetic, an antibody and an antigen binding molecule. In one embodiment, the oligonucleotide may be a siRNA or shRNA.

In one embodiment, the contacting step comprises transfecting the cell with the siRNA or shRNA.

In some embodiments, the cell may be permissive or non-permissive of HBV replication.

A "permissive" cell as disclosed herein relates to a cell that allows the virus to circumvent its defences and replicate. Usually this occurs when the virus has modulated one or several of the cells intrinsic defences. There are conventional methods and techniques known to the skilled person in determining or validating if a cell or cell line is permissive to a certain virus. In contrast, a "non-permissive" cell as disclosed herein relates to a cell that does not allow the virus to circumvent its defences and replicate.

The cell may be selected from the group consisting of a liver cell, colon cell, stomach cell, blood cell, kidney cell and lung cell. In one embodiment, the cell may be a liver cell or a non-liver cell. In another embodiment, the cell may be derived from a HBV liver permissive cell line, such as HepG2, HuH7, PLC/PRF/5 or Hep3B. In another embodiment, the cell may be derived from a non-liver HBV permissive cell line such as Caco-2, Kato III, AGS or A549. In yet another embodiment, the cell may be derived from a non-liver HBV non-permissive cell line, such as T24, 5637, PC-3, Saos-2, FS-4 or COLO316.

In some embodiments, the cell may be comprised in a biological sample. A biological sample may be a sample of tissue or cells from a patient that has been obtained from, removed or isolated from the patient. Non-limiting examples of biological samples include whole blood or a component thereof (e.g. plasma, serum), urine, saliva lymph, bile fluid, sputum, tears, cerebrospinal fluid, bronchioalvcolar lavage fluid, synovial fluid, semen, ascitic tumour fluid, breast milk and pus. In one embodiment, the sample of nucleic acid is obtained from blood, amniotic fluid or a buccal smear. [SF: Please confirm if this is correct]

A biological sample, as contemplated herein, may also include cultured biological materials, including a sample derived from cultured cells, such as culture medium collected from cultured cells or a cell pellet. Accordingly, a biological sample may refer to a lysate, homogenate or extract prepared from a whole organism or a subset of its tissues, cells or component parts, or a fraction or portion thereof. A biological sample may also be modified prior to use, for example, by purification of one or more components, dilution, and/or centrifugation. In some embodiments the biological sample may be obtained from an HBV infected subject.

In some embodiments, the cell may be derived from a cell line selected from the group consisting of HepG2, HuH6, HuH7, HuH4, PLC/PRF/5, Kato III, AGS, HCT116, Caco-2, HL-60, HEK293 and A549.

In one embodiment, the contacting step may comprise culturing the cell in a suitable culture medium that promotes HBV replication. In another embodiment the contacting step may comprise transfecting the cell with a HBV replicon.

In one embodiment, the step of obtaining the HBV expression profile may comprise measuring one or more markers of HBV replication. The one or more markers of HBV replication may be selected from the group consisting of pre-genomic RNA levels of the HBV replicon, hepatitis B surface antigen levels, and hepatitis B core antigen levels.

In some embodiments, the step of obtaining the HBV expression profile may comprise western blot analysis of the at least one factor in the cell and measuring a band intensity of the at least one factor. The band intensity of the at least one factor may be normalized to a control. In some embodiments, a relative difference of 1 to 35% or greater between the band intensity of the at least one factor and the control may indicate a modulation of HBV replication by said at least one agent.

Figure 1:
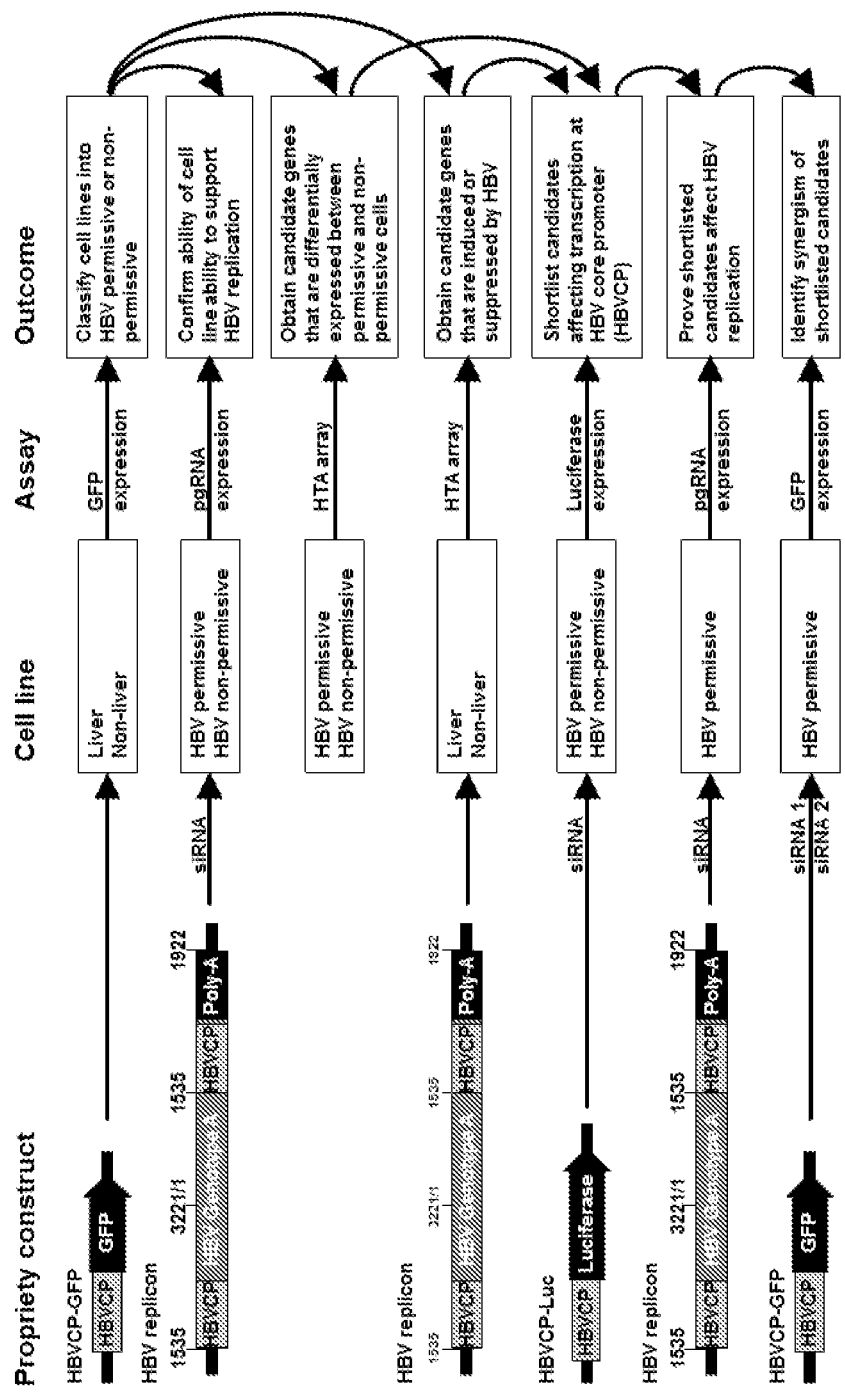
FIG. 1. is a schematic diagram illustrating the experimental flow for discovery and validation of host factors that modulate the replication of HBV.

Also provided is a method of identifying at least one factor that modulates replication of a virus. The method comprises a) transfecting at least two cell lines of different origins with an expression construct comprising a selection marker operably linked to a viral promoter of the virus; b) detecting the expression of the selection marker to classify the at least two cell lines into permissive and non-permissive cell lines; c) transfecting the permissive and non-permissive cell lines with an expression construct comprising a viral replicon of the virus; d) screening for expression of at least one factor in said permissive and non-permissive cell lines of c), and comparing the expression of the at least one factor in the permissive cell line to the non-permissive cell line, to identify at least one candidate factor, wherein the differential expression of the at least one factor between the permissive and non-permissive cell line is indicative of identifying at least one candidate factor; e) contacting said permissive cell line expressing the viral replicon with an agent to knock out expression of said at least one candidate factor; and f) comparing the pre-genomic RNA level of said viral replicon in said permissive cell line of e) relative to a control cell line that has not been contacted with said agent, wherein a decrease or increase in the expression level of the pre-genomic RNA level in the permissive cell line, relative to the control cell line, indicates the identification of at least one factor that modulates replication of the virus. (FIG. 1)

In one embodiment, the at least one candidate factor may be selected from the group consisting of a transcription factor, regulation factor, RNA processing factor and signaling molecule.

In another embodiment, the selection marker may be green fluorescent protein (GFP) or luciferase.

In one embodiment the agent may be a siRNA or a shRNA.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Non-limiting examples of the invention, including the best mode will be further described in greater detail by reference to specific Examples, which should not be construed as in any way limiting the scope of the invention and are merely illustrative of the general concept of the present invention.

Materials and Methods

Cells and Reagents

Cell lines HepG2, HuH7, PLC/PRF/5, Hep3B, AGS, A549, PC-3, Saos-2 and FS-4 were maintained in Dulbecco's modified Eagle's medium (DMEM) supplemented with 10% fetal bovine serum (FBS). Caco-2 was grown in Eagle's minimum essential medium (EMEM) supplemented with 20% FBS, while T24, 5637, and COL0316 were grown in RPMI-1640 supplemented with 10% FBS. Kato III was maintained in DMEM supplemented with 20% FBS.

All cells were grown at 37° C. in a humidified incubator containing 5% CO2, and cultured according to the manufacturing instructions. Primary human hepatocytes were purchased from Triangle Research Labs and cultured as recommended. Total RNA from primary human tissues were purchased from Zyagen.

Primary antibodies used are as follows: HBcAg rabbit polyclonal antibody (Dako), HNF4α7/8/9 mouse monoclonal antibody clone H6939 (R & D Systems), HNF4α1/2/3 mouse monoclonal antibody clone K9218 (R & D Systems), Slug mouse monoclonal antibody clone A-7 (Santa Cruz Biotechnology), Sox7 goat polyclonal antibody (R & D Systems), lamin A/C goat polyclonal antibody (Santa Cruz Biotechnology), β-actin mouse monoclonal antibody (Santa Cruz Biotechnology), albumin mouse monoclonal antibody clone AL-01 (Santa Cruz Biotechnology), transferrin mouse monoclonal antibody clone D-9 (Santa Cruz Biotechnology). HRP-conjugated secondary antibodies were purchased from Dako. Fluorophore conjugated antibodies (Alexa Fluor® 488 and Alexa Fluor® 546) for immunofluorescence staining was obtained from Life Technologies.

Primers for full-length Slug detection were Slug-F (5' CGATGCTGTAGGGACCGC 3' (SEQ ID NO: 222)) and Slug-R (5'TGGTCAGCACAGGAGAAAATGC 3'(SEQ ID NO: 223). The primer pair to detect for full-length Sox7 were Sox7-F (5' TATGCTAGCATGGCTTCGCTGCTGG 3'(SEQ ID NO: 224) and Sox7-R (5' TAATCTAGACTATGACACACTGTAGCTGTTGTAG 3'(SEQ ID NO: 225). RNA was extracted using the Nucleospin RNA kit (Machery Nagel), and 100 ng RNA was used for first strand cDNA synthesis using the AccuScript High Fidelity 1st Strand cDNA Synthesis Kit (Stratagene) according to manufacturers' instructions.

Plasmids

Figure 10A:
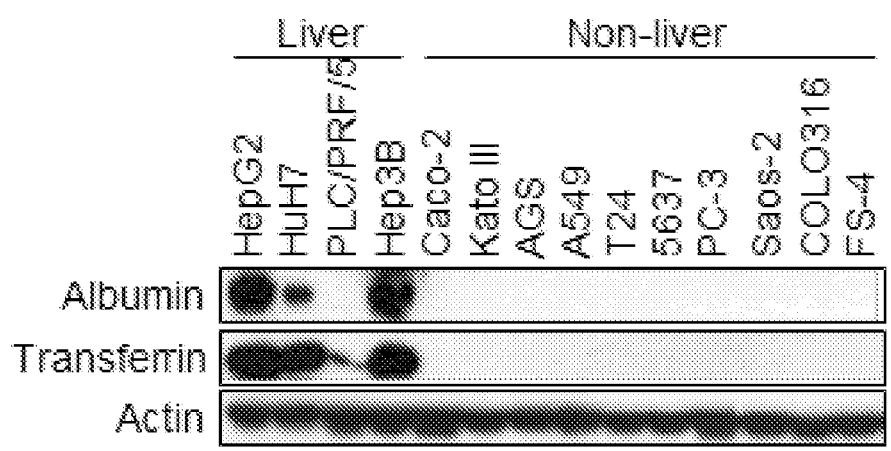
FIG. 10 shows the HBV replication in non-liver cells. a) Expression of liver-specific markers in cell lines by western blot. Only cell lines originating from liver express albumin and/or transferrin. Actin was used as loading control; b) Cell lines were tested for transfection efficiency using CMV-GFP reporter construct; c) The HBV replicon. 1.1× full-length HBV from genotype A (nt 1535-1937) was cloned into pcDNA3.1+ vector upstream of the CMV promoter. pgRNA synthesis is controlled at the HBVCP, terminating at the HBV poly-adenylation (poly-A) signal after initial read-through transcription; d) Expression of HBV capsid protein HBcAg in cells transfected with HBV replicon for 72 hours.
Figure 10B:
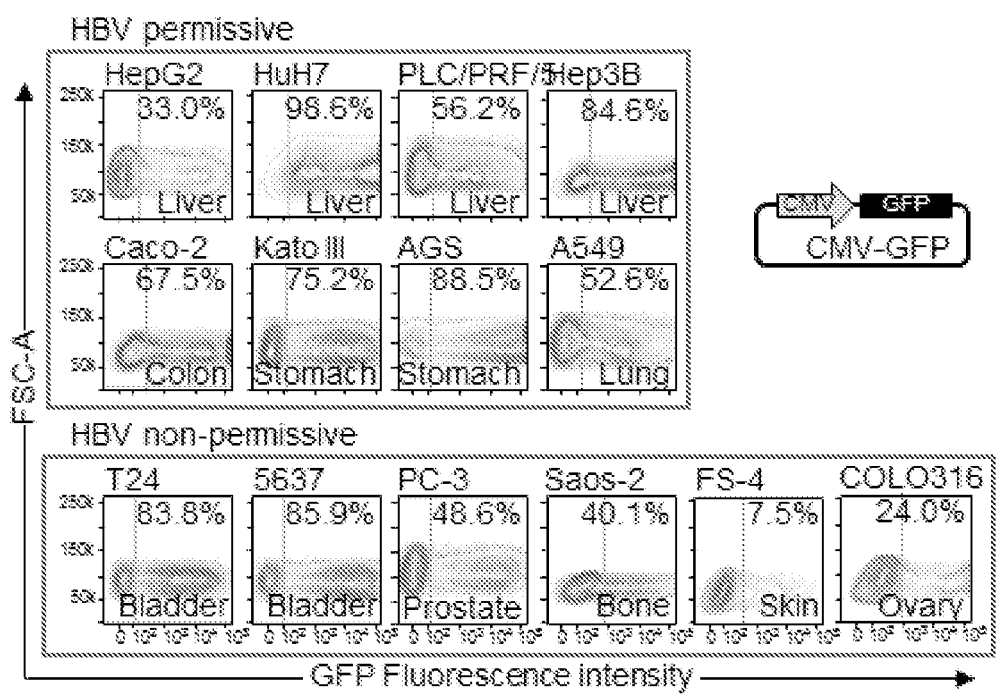

The HBV replicon was cloned from 1.1× of HBV genotype A (nt 1535-1937) and inserted into pcDNA3.1+ vector upstream of the CMV promoter (FIG. 10b).

Thus, pgRNA synthesis is dependent only on active transcription at the HBVCP (nt 1600-1860), and full-length pgRNA generated terminates at the HBV poly-adenylation signal after initial read-through transcription. HBVCP-Luc was generated by insertion of HBVCP into the PGL3 Basic (Promega) plasmid through KpnI and HindIII restriction sites. HBVCP-GFP was generated by swapping the coding sequence of luciferase in HBVCP-Luc with the coding sequence of green fluorescent protein (GFP) from pTurboGFP-C plasmid (Evrogen).

HNF4α overexpression constructs for each isoform were generated by insertion of amplification products from 2-step PCR (polymerase chain reaction) outlined in Tables 2, 3 and 4 into pIVEX2.5d vector through NotI and XmaI sites and sub-cloned into pcDNA3.1+ using NotI and XbaI restriction sites. cDNA from HepG2 was used as template to generate the HNF4α amplicons.

TABLE 2

| Cloning and Amplification Primers | |
|---|---|
| Primer | Sequence |
| NotI-HNF4α123-F | 5' TGAGCGGCCGCGATATGCGATCTC 3' (SEQ ID NO: 1) |
| NotI-HNF4α789-F | 5' TGAGCGGCCGCGATATGGTCAGCG 3' (SEQ ID NO: 2) |
| HNF4a1278-XmaI-R | 5' ATTCCCGGGATAACTTCCTGCTTGGTG 3' (SEQ ID NO: 3) |
| HNF4α39-XmaI-R | 5' ATTCCCGGGAGCAACTTGCCCAAAGCG 3' (SEQ ID NO: 4) |
| HNF4α17F | 5' AACGGACAGATGTCCACCCCTGAGACC 3 (SEQ ID NO: 5) |
| HNF4α17R | 5' GGTCTCAGGGGTGGACATCTGTCCGTT 3' (SEQ ID NO: 6) |
| HNF4α28F | 5' AGCAACGGACAGATGTGTGAGTGGCC 3' (SEQ ID NO: 7) |
| HNF4α28R | 5' GGCCACTCACACATCTGTCCGTTGCT 3' (SEQ ID NO: 8) |

TABLE 3

Cloning Strategy

| HNF4α isoform | Step 1: Generate fragments with complementary ends | | Step 2: Anneal fragments and amplify | |
|---|---|---|---|---|
| | 5' fragment | 3' fragment | Forward primer | Reverse primer |
| HNF4α1 | A | B | NotI-HNF4α123-F | HNF4α1278-XmaI-R |
| HNF4α2 | C | D | NotI-HNF4α123-F | HNF4α1278-XmaI-R |
| HNF4α7 | F | B | NotI-HNF4α789-F | HNF4α1278-XmaI-R |
| HNF4α8 | G | D | NotI-HNF4α789-F | HNF4α1278-XmaI-R |
| HNF4α3 | E (Does not require annealing of separate fragments) | | | |
| HNF4α9 | H (Does not require annealing of separate fragments) | | | |

TABLE 4

| Fragment | Forward primer | Reverse primer |
|---|---|---|
| A | NotI-HNF4α123-F | HNF4α17-R |
| B | HNF4α17-F | HNF4α1278-XmaI-R |
| C | NotI-HNF4α123-F | HNF4α28-R |
| D | HNF4α28-F | HNF4α1278-XmaI-R |
| E | NotI-HNF4α123F | HNF4α39-XmaI-R |
| F | NotI-HNF4α789-F | HNF4α17-R |
| G | NotI-HNF4α789-F | HNF4α28-R |
| H | NotI-HNF4α789-F | HNF4α39-R |

Overexpression constructs for human Slug and Sox7 were obtained from Origene. Plasmids carrying mutations in HBVCP-Luc were generated by site-directed mutagenesis using the QuickChange II Site-Directed Mutagenesis kit (Agilent Technologies).

Human Transcriptome Array (HTA 2.0)

Total RNA was extracted from cells 30 hours after seeding in 10 cm dishes till 50% confluent. Only good quality RNA with RIN (RNA integrity number) value >9.80 was used. Processed cRNA from the cell lines was hybridized to the Affymetrix Human Transcriptome Array 2.0 according to the manufacturer's protocols. The Affymetrix® Expression Console™ Software (version 1.3.1.187) was used to normalize the data for both gene level and exon level analysis in $\log_2$ scale. Only protein coding genes were considered for evaluation.

The global gene expression profiles were assessed using principal component analysis (PCA). The resultant principle components were used as input to determine sample clustering topology by k-means. Differential expression analysis was performed using the Limma package and the p-values were adjusted for multiple testing with Benjamini and Hochberg. Only genes with adjusted p-value<0.05 and |$\log_2$(fold-change)|>0.5 were identified as differentially expressed. All the above statistical analysis was implemented using R version 3.1.1.

Differentially expressed genes were subjected to gene ontology annotation analysis using PANTHER classification system (version 10.0). The microarray data is available at Gene Expression Omnibus under the accession number GSE72779.

Validation Assay—(siRNA with HBV pgRNA Readout)

In order to determine if HBV replication is modulated by the listed genes in Tables 5 and 8, over-expression and siRNA knock-down studies were performed to determine if HBVCP activity and pgRNA synthesis would be affected by altered gene expression.

The validation assays were performed in HBV permissive cells. In HBVCP activity assays, 50 ng over-expression constructs or 10 nM siRNA were co-transfected with HBVCP-Luc (luciferase reporter). The relative luminescence was compared to a negative siRNA control or an empty vector control and determined 48 hours post-transfection. In pgRNA assays, 50 ng over-expression constructs or 10 nM siRNA were co-transfected with 800 ng full-length HBV replicon and the relative amount of pgRNA 72 hours post-transfected normalized against GAPDH loading control was compared with that of empty vector or negative siRNA controls.

HBV Replication Assays

For pgRNA assay and immunofluorescence staining for HBcAg, HepG2 and Caco-2 cells were seeded in 24-well plates at $1.0-1.5 \times 10^5$ cells per well and transfected with 800 ng HBV replicon, 1.1 µl Lipofectamine® 2000 (Thermo-Fisher Scientific) in 100 µl OPTI-MEM. Overexpression constructs were added when indicated at 50 ng per well per construct. Primary human hepatocytes were transfected with 5.6 µl Lipofectamine® 2000.

Silencer® Select Validated siRNA specific for Slug, Sox7 and negative control siRNA were purchased from Thermo-Fisher Scientific and co-transfected at 10 nM concentration unless stated otherwise. 10 µM peptides in 0.2% DMSO were added 24 hours post-transfection.

Transfected cells were analyzed 48-72 hours post-transfection. Full-length pgRNA was amplified using pgRNA-F (5' ACACCGCCTCAGCTCTGTATCGAG 3' (SEQ ID NO: 9)) and pgRNA-R (5' TTCTTTATAAGGGTCAATGTC-CATGCCCC 3' (SEQ ID NO: 10)) primers with reagents from Expand™ Long Template PCR System (Sigma Aldrich). HBcAg immunofluorescence staining was performed after 20 minute fixation using 4% paraformaldehyde, antigen retrieval with 0.1% TritonX-100 in PBS for 10 minutes, blocking at 4° C. overnight with blocking buffer (1% bovine serum albumin in PBS). Primary antibodies were added at 1:100 dilution in blocking buffer for 2 hours at room temperature, washed thrice with PBS and incubated with 1:1000 secondary antibodies for 1 hour. DAPI was used to stain nuclei.

HBVCP Activity Assays

Luciferase reporter assay for HBVCP transcription activity was performed as recommended (Promega). Cells at a density of $3 \times 10^4$ cell per well were transfected with 160 ng wild type or mutant HBVCP-Luc constructs into 96-well black clear bottom plates with 0.22 µl Lipofectamine® 2000. Additional overexpression constructs were co-transfected at 10 ng per well per construct, and siRNA at 10 nM unless indicated otherwise.

Cells were lysed and luminescence determined 30 hours post-transfection for experiments with HBVCP-Luc alone, and at 48 hours after transfection for experiments with overexpression or knockdown.

In experiments involving transcription factor mimetics, 10 µM peptides in 0.2% DMSO were added 24 hours post-transfection unless stated otherwise.

HBVCP transcription activity was also assessed using the HBVCP-GFP construct and analyzed by flow cytometry using 1.6 μg HBVCP-GFP alone or together with 100 ng overexpression construct, 2.2 μl Lipofectamine® 2000 in 12-well plates, and harvested 48 hours post-transfection. Cells were washed twice in PBS, re-suspended in staining buffer (2% FBS, 10 mM EDTA in PBS), passed through 40 μm cell strainer prior to flow cytometry. Data was acquired using BD FACSCanto II (BD Biosciences) and analyzed using Flowjo v10.

Electrophoretic Mobility Shift Assay (EMSA).

Nuclear lysates were obtained using NEPER (Nuclear and Cytoplasmic Extraction Reagents; ThermoFisher Scientific) as instructed from $4.5 \times 10^6$ cells transfected with empty vector or overexpression constructs using 30 μg plasmids, 33 μl Lipofectamine® 2000 in 10 cm dishes 48 hours after transfection.

EMSA was performed in 20 μl reactions as recommended using the LightShift™ Chemiluminescent EMSA kit (ThermoFisher Scientific), with 0.5 ng biotinylated probes, 2 μg nuclear lysates in the presence of 1-2 μg poly-dIdC. DNA-protein complexes were allowed to form at 37° C. for 45 minutes, and electrophoresis performed on 5% gels with TBE buffer system.

siRNA's

| No | Gene | siRNA 1 | siRNA 2 | siRNA 3 | siRNA 4 |
|---|---|---|---|---|---|
| | | Transcription regulation and RNA processing | | | |
| 1 | ARID3A | GAGAUCAACGGCAUCAUGU (SEQ ID NO: 11) | CUUACGAGGAGCAGUUUAA (SEQ ID NO: 12) | UCAAAUAACUCGUUGCCUU (SEQ ID NO: 13) | GAAACUACAGGCCGUGAUG (SEQ ID NO: 14) |
| 2 | ATF2 | GAGAAGAGCAGCUAACGAA (SEQ ID NO: 15) | CAUGGUAGCGGAUUGGUUA (SEQ ID NO: 16) | GGAAGUACCAUUGGCACAA (SEQ ID NO: 17) | UGAGGAGCCUUCUGUUGUA (SEQ ID NO: 18) |
| 3 | ATF3 | GAGCUAAGCAGUCGUGGUA (SEQ ID NO: 19) | GCAAAGUGCCGAAACAAGA (SEQ ID NO: 20) | AGAAGCAGCAUUUGAUAUA (SEQ ID NO: 21) | CGAGAAAGAAAUAAGAUUG (SEQ ID NO: 22) |
| 4 | ATF4 | CAGAUUGGAUGUUGGAGAA (SEQ ID NO: 23) | CGACUUGGAUGCCCUGUUG (SEQ ID NO: 24) | GAAGAACGAGGCUCUAAAA (SEQ ID NO: 25) | GAGAUAGGAAGCCAGACUA (SEQ ID NO: 26) |
| 5 | CALCOCO1 | GUGCAGAGAUACUUCGAUU (SEQ ID NO: 27) | GGACAUCCUGAGCCGGCAA (SEQ ID NO: 28) | UGACAGACUCAGAGGACGA (SEQ ID NO: 29) | UGUCAGAAAGUAAGCGGGA (SEQ ID NO: 30) |
| 6 | CHD3 | GAAUAUCCCUGAAUACGAA (SEQ ID NO: 31) | CCAGAAUGAUGCUCAAUUU (SEQ ID NO: 32) | CAUAAGAGGCGGAGUAAGA (SEQ ID NO: 33) | CGUAUGAGCUGAUCACCAU (SEQ ID NO: 34) |
| 7 | CNOT11 | GGAUGAACUUGCUUGGCUA (SEQ ID NO: 35) | GUGUGGAGAUCAAACGAAU (SEQ ID NO: 36) | GGAAGUUGUAAAUCGACUA (SEQ ID NO: 37) | AUUCAGUAGGAUACGAGAA (SEQ ID NO: 38) |
| 8 | DCP1A | GCAAGCUUGUCGAUAUAUA (SEQ ID NO: 39) | ACUCAUGGCUGAUGUGGUA (SEQ ID NO: 40) | ACAAGCAUCUGACGGUAGA (SEQ ID NO: 41) | CCAAUUCAUUCCUACCAUU (SEQ ID NO: 42) |
| 9 | DDX39B | GUAGAAGACUCGCCCAUUU (SEQ ID NO: 43) | GGGCUUGGCUAUCACAUUU (SEQ ID NO: 44) | GAAUGGAUGUCCUGUGCA (SEQ ID NO: 45) | GAACUGCCCGCAUAUCGUC (SEQ ID NO: 46) |
| 10 | DYRK1B | GAGAUGAAGUACUAUAUAG (SEQ ID NO: 47) | CGAAAGAACUCAGGAAGGA (SEQ ID NO: 48) | GGGUGAAAGCCUAUGAUCAU (SEQ ID NO: 49) | GGACCUACCGCUACAGCAA (SEQ ID NO: 50) |
| 11 | E2F6 | CAACGGACCUAUCGAUGUC (SEQ ID NO: 51) | UAGCAUAUGUGACCUAUCA (SEQ ID NO: 52) | GUAAGCAACUGAUGGCAUU (SEQ ID NO: 53) | GAACAGAUCGUCAUUGCAG (SEQ ID NO: 54) |
| 12 | E2F7 | GCACACAUCGUGAGACAUU (SEQ ID NO: 55) | UGACUAACCUGCCGCUUUG (SEQ ID NO: 56) | CAAGGACGAUGCAUUUACA (SEQ ID NO: 57) | GGACUAUUCCGACCCAUUG (SEQ ID NO: 58) |
| 13 | EPAS1 | GGCAGCACCUCACAUUUGA (SEQ ID NO: 59) | GAGCGCAAAUGUACCCAAU (SEQ ID NO: 60) | GACAAGGUCUGCAAAGGGU (SEQ ID NO: 61) | GCAAAGACAUGUCCACAGA (SEQ ID NO: 62) |
| 14 | FOXN2 | CCUUUAGUCUUCUCAUUUA (SEQ ID NO: 63) | GGAUGAGGUAUAUGAAUUU (SEQ ID NO: 64) | GGAUUAAGCCAGAUUUACA (SEQ ID NO: 65) | CAUGAAAGCACUAAUCUUC (SEQ ID NO: 66) |
| 15 | HIVEP2 | CAUCAUGGCUUCCGAUUAU (SEQ ID NO: 67) | CGAAGCAUAUGAAAUCUAA (SEQ ID NO: 68) | GCACUUAAGACCUUGCUA (SEQ ID NO: 69) | GGGAUAGGAUUCAACAUUG (SEQ ID NO: 70) |
| 16 | KANK2 | CGUGCGAUCUAUCAUGAAA (SEQ ID NO: 71) | CAGCUCACAGUACAACUUA (SEQ ID NO: 72) | GACGAGAGCCCUACAUCAU (SEQ ID NO: 73) | GAACGGGACUUGGGCAUGC (SEQ ID NO: 74) |
| 17 | LIN54 | AAAUAGUGGAGGCGAAAA (SEQ ID NO: 75) | GAACAGGGAAUGUGGGUUA (SEQ ID NO: 76) | GUCAGGAGAUGCUAAGUUA (SEQ ID NO: 77) | GUGAAUGCUAUGAGGCAAA (SEQ ID NO: 78) |
| 18 | NCL | GCAAAGAAGGUGGUCGUUU (SEQ ID NO: 79) | GAUAGUUACUGACCGGGAA (SEQ ID NO: 80) | CAAAUCUGCUCCUGAAUUA (SEQ ID NO: 81) | GAAAGAAGACGAAGUUUGA (SEQ ID NO: 82) |
| 19 | PNPT1 | GACAGAAGUAGUAUUGUAA (SEQ ID NO: 83) | ACAGAAAGAUUAUUGGCUA (SEQ ID NO: 84) | GAAUGUAAGUUGUGAGGUA (SEQ ID NO: 85) | AAUCAGAGAUACUGGUGUA (SEQ ID NO: 86) |
| 20 | POLR3E | UGGAUAAGGCUGACGCCAA (SEQ ID NO: 87) | GGGAGCAGAUUGCGCUGAA (SEQ ID NO: 88) | CGACGAGACCAGCACGUAU (SEQ ID NO: 89) | CCUCGAUGACCUACGAUGA (SEQ ID NO: 90) |
| 21 | RNASEH2A | CGGGAAAGGCUGUUUGCGA (SEQ ID NO 91:) | AAAUGGAGGACACGGACUU (SEQ ID NO: 92) | AUGCAUUGGACCAGGGCGU (SEQ ID NO: 93) | AGACCCUAUGGAGAGCGA (SEQ ID NO: 94) |
| 22 | RNF4 | GCUAUACUUGCCCAACUU (SEQ ID NO: 95) | GAAUGGACGUCUCAUCGUU (SEQ ID NO: 96) | GACAGAGACGUAUAUGUGA (SEQ ID NO: 97) | GCAAUAAAUUCUAGACAAG (SEQ ID NO: 98) |
| 23 | SERBP1 | CAAAAUAAGGACCGGGCAA (SEQ ID NO: 99) | AGGCUGAGGAAGUCGGUAA (SEQ ID NO: 100) | GGGUGAAGGAGGCGAAUUU (SEQ ID NO: 101) | GAAAGAAGGAAUAAGACGA (SEQ ID NO: 102) |
| 24 | SKA1 | GGGAGGACUUACUCGUAAU (SEQ ID NO: 103) | AUUAUUGGGCUUUCGUAUA (SEQ ID NO: 104) | UGAAGAACCUGAACCCGUA (SEQ ID NO: 105) | GUACAUGAAAUCCCGCUUA (SEQ ID NO: 106) |
| 25 | SMAD3 | CAACAGGAAUGCAGCAGUG (SEQ ID NO: 107) | GAGUUCGCCUUCAAUAUGA (SEQ ID NO: 108) | GGACGCAGGUUCUCCAAAC (SEQ ID NO: 109) | UUAGAGACAUCAAGUAUGG (SEQ ID NO: 110) |
| 26 | SNA12 | UCUCUCCUCUUUCCGGAUA (SEQ ID NO: 111) | GCGAUGCCCAGUCUAGAAA (SEQ ID NO: 112) | ACAGCGAACUGGACACACA (SEQ ID NO: 113) | GAAUGUCUCUCCUGCACAA (SEQ ID NO: 114) |
| 27 | SOX7 | AGAGCAACUUCCCGCAAAU (SEQ ID NO: 115) | GAAAAUGGGAUUGAGUUAA (SEQ ID NO: 116) | CAAAGGACUCAUACAAUU (SEQ ID NO: 117) | GCAUAACAGUGUGCUGAAU (SEQ ID NO: 118) |
| 28 | SSB | GGUCUAGAUUUAAAGGAA (SEQ ID NO: 119) | GGUUAGAAGAUAAAGGUCA (SEQ ID NO: 120) | GAGACCAGUAGUUUAGUAA (SEQ ID NO: 121) | GGGAAGUACUAGAAGGAGA (SEQ ID NO: 122) |
| 29 | STAM | GAACGAAGAUCCGAUGUAU (SEQ ID NO: 123) | CCACAAAGAUCCUCACGUU (SEQ ID NO: 124) | GGAGUUACGUUCCCAGCUA (SEQ ID NO: 125) | CAUCCAGUCUCUUAACUAA (SEQ ID NO: 126) |

-continued

| No | Gene | siRNA 1 | siRNA 2 | siRNA 3 | siRNA 4 |
|---|---|---|---|---|---|
| 30 | TFAP2A | GUAUUAACAUCCCAGAUCA (SEQ ID NO: 127) | CGUAAAGCUGCCAACGUUA (SEQ ID NO: 128) | CCACCUAGCCAGGGACUUU (SEQ ID NO: 129) | UAACAAGGACAACCUCUUC (SEQ ID NO: 130) |
| 31 | TFAP2C | CCGAUAAUGUCAAGUACGA (SEQ ID NO: 131) | ACACUGGAGUCGCCGAAUA (SEQ ID NO: 132) | GUAAACCAGUGGCAGAAUA (SEQ ID NO: 133) | GGACAAGAUUGGGUUGAAU (SEQ ID NO: 134) |
| 32 | TFB2M | CAAAUGAUUCCUCGUCAAA (SEQ ID NO: 135) | ACCAAGAACUUAACACCUA (SEQ ID NO: 136) | GAAACUCGCAUAUGACUUG (SEQ ID NO: 137) | GAUCGGAGAUUGGCUGAGA (SEQ ID NO: 138) |
| 33 | TP73 | GAGACGAGGACACGUACUA (SEQ ID NO: 139) | GCAAUAAUCUCUCGCAGUA (SEQ ID NO: 140) | GAACUUUGAGAUCCUGAUG (SEQ ID NO: 141) | CCACCAUCCUGUACAACUU (SEQ ID NO: 142) |
| 34 | TRIM24 | GAGCAUAGAUACCAAUUUA (SEQ ID NO: 143) | GAAGAACGCCAGUUGCUUA (SEQ ID NO: 144) | GAUCAUAGAUACACUAAUC (SEQ ID NO: 145) | UAACUGUGCCUGAUUAUUA (SEQ ID NO: 146) |
| 35 | TRIM27 | CGGAGAGUCUAAAGCAGUU (SEQ ID NO: 147) | GAACCAGCUCGACCAUUUG (SEQ ID NO: 148) | GAGAUGGGCGUGUGCAGA (SEQ ID NO: 149) | UAAGAGAGGCUCAGUUAUU (SEQ ID NO: 150) |
| 36 | TRIM68 | GAAGGGAAAUGAGUACCGA (SEQ ID NO: 151) | GAACUGGGGUUACACCUGU (SEQ ID NO: 152) | GAGAGAUCCUGAAGACUUA (SEQ ID NO: 153) | GAGGAUGUCUUGAUAAUGU (SEQ ID NO: 154) |
| 37 | WDR54 | GCUAUGACCUUGCGGAGAU (SEQ ID NO: 155) | CCAACAUUGUACUGAGCAA (SEQ ID NO: 156) | AGGCUAUGGGAACGGACAA (SEQ ID NO: 157) | GCUCGCAACCUCACGUAUU (SEQ ID NO: 158) |
| 38 | ZNF518A | CGAUAUAGCCCAAAUGAUU (SEQ ID NO: 159) | GCUAAUAUUCGCAGCACUA (SEQ ID NO: 160) | CUUGCUAAGUAUUCAGUAA (SEQ ID NO: 161) | GCAAAGGACGGUACUGCUA (SEQ ID NO: 162) |
| 39 | HNF4α | GACCGGAUCAGCACUCGAA (SEQ ID NO: 163) | CGGAAGAACCACAUGUACU (SEQ ID NO: 164) | GGGCUGGCAUGAAGAAGGA (SEQ ID NO: 165) | CCAAGUACAUCCCAGCUUU (SEQ ID NO: 166) |

Signaling molecules

| 40 | CPD | GAAAUUCGCAUGAUGUCUA (SEQ ID NO: 167) | GAACUAGGUUGUGUGAAAU (SEQ ID NO: 168) | GGAGAACAAUCGUGAGUCU (SEQ ID NO: 169) | GCACAGUUGCUAUACCUAA (SEQ ID NO: 170) |
| 41 | CSNK2A2 | GAGUUUGGGCUGUAUGUUA (SEQ ID NO: 171) | GGGACAACAUUCACGGAAA (SEQ ID NO: 172) | GAUAGAUCACCAACAGAAA (SEQ ID NO: 173) | UUAAGCAACUCUACCAGAU (SEQ ID NO: 174) |
| 42 | HERPUD1 | CGACAGUACUACAUGCAAU (SEQ ID NO: 175) | GGGCCACCGUUGUUAUGUA (SEQ ID NO: 176) | GGCUUCAGCUUUCCUGGUU (SEQ ID NO: 177) | GCGGAUGAAUGCACAAGGU (SEQ ID NO: 178) |
| 43 | KPNA3 | GUCAAUCUCUGCAGGAAUA (SEQ ID NO: 179) | GAUAAUGGCCGGUGAUGAA (SEQ ID NO: 180) | GAAAAGAUCAGGUUGAGUA (SEQ ID NO: 181) | ACAAGGAGGUACCUACAAU (SEQ ID NO: 182) |
| 44 | PAK1IP1 | CUAGUGUGCCUCUGCGAAU (SEQ ID NO: 183) | UUUAAUCAGUGGAGCGGAA (SEQ ID NO: 184) | CAUCACAGUGGUACAAUAA (SEQ ID NO: 185) | GUCGGUUGGUACAGAUAAA (SEQ ID NO: 186) |
| 45 | PRDX3 | GUAGAUCACCCAUGUGUAU (SEQ ID NO: 187) | GAACAUCGCACUCUUGUCA (SEQ ID NO: 188) | AGACUACGGUGUGCUGUUA (SEQ ID NO: 189) | GAGCUUGACAAAUUUAUUG (SEQ ID NO: 190) |
| 46 | PTP4A1 | GAUUGUUGAUGACUGGUUA (SEQ ID NO: 191) | CCAAUGCGACCUUAAACAA (SEQ ID NO: 192) | GCAAGCAACUUCUGUAUUU (SEQ ID NO: 193) | GAAAGAAGGUAUCCAUGUU (SEQ ID NO: 194) |
| 47 | RHOB | GCAUCCAAGCCUACGACUA (SEQ ID NO: 195) | CAGAACGGCUGCAUCAACU (SEQ ID NO: 196) | CGACGAGCAUGUCCGCACA (SEQ ID NO: 197) | AAGCACUUCUGUCCCAUG (SEQ ID NO: 198) |
| 48 | RNF43 | GCAGAACAGAAAGCUAUUA (SEQ ID NO: 199) | UAUGAUGUGUGGAUCCAA (SEQ ID NO: 200) | GGAGAAAGCUAUUGCACAG (SEQ ID NO: 201) | GGUGGAGUCUGAAAGAUCA (SEQ ID NO: 202) |
| 49 | SRPK1 | GAACAUAACGGACCACUGG (SEQ ID NO: 203) | GAUACCAUGUGAUCCGAAA (SEQ ID NO: 204) | GCAGCUGGCUUCACAGAUU (SEQ ID NO: 205) | ACACAUAUCUGCAUGGUAU (SEQ ID NO: 206) |
| 50 | STRADB | GCACCAAAAUGGCUGUAUU (SEQ ID NO: 207) | GGGAUUACAGCAUGUGAAU (SEQ ID NO: 208) | AGUAAAUAGUGACCGAUUA (SEQ ID NO: 209) | GGUAUAAUGUGAAGUCAGA (SEQ ID NO: 210) |
| 51 | STT3B | GAGCAUCAACCUACGACUU (SEQ ID NO: 211) | GAUCACAAACCUCGAGUCA (SEQ ID NO: 212) | AGAUGAACAUGCACGAGUA (SEQ ID NO: 213) | ACAUAGCACUGGUGGGAAA (SEQ ID NO: 214) |

Stapled Peptides

Multiple sequence alignments were performed using Clustal Omega to identify conserved DNA-binding domains and residues between Slug, its orthologues and human Snail and Smuc, as well as between Sox7, its orthologues and human Sox17 and Sox18.

Relative positions of α-helices within the $C_2H_2$ zinc finger domains of Slug were predicted using CFSSP (Chou & Fasman Secondary Structure Prediction Server) and JPred4 to identify DNA binding residues at positions −1, +2, +3 and +6 of each α-helix.

Helical wheel diagrams were drawn with HeliQuest to determine DNA-binding surfaces so that hydrocarbon staples may be positioned with low probability of disrupting peptide-DNA interaction. Peptides (GeneScript) were synthesized at >95% purity, dissolved in DMSO and incubated with cells at final concentration of 10 μM in 0.2% DMSO unless stated otherwise. WST-1 assay (Sigma-Aldrich) for cell proliferation was performed as recommended in the manufacturer's instructions.

In Vivo Animal Models

As readily understood and appreciated by those skilled in the art, there are no conventional small animal models for HBV replication as HBV does not naturally infect non-primates. In this regard, the most relevant mouse model for HBV involves injection of primary human hepatocytes into immuno-compromised mice. Since data is already provided herein using primary human hepatocytes, it was determined that injecting the hepatocytes into small animals would not provide significant added advantage to the conclusions drawn and described herein.

Statistical Analysis

Data is expressed as means±s.e.m. and unpaired Student's t-test was performed. $P<0.05$ was considered significant.

Example 1

Using a panel of liver and non-liver cell lines, a number of host factors were identified to influence the efficiency of HBV replication.

Through the use of siRNAs to knock down the genes associated with the factors, it was shown that transcriptional activity controlled by a HBV core promoter, as well as the replication of the entire HBV genome, may be modulated. The siRNAs applied for each gene target were in an equimolar mixture for down-regulating the gene (gene ID). This supporting the theory these genes may function as targets to develop interventions that can be used to modulate and control HBV replication.

Development of a HBV Transcription Screen

A HBV core promoter (HBVCP)-green fluorescence protein (GFP) construct was developed for use in transfecting different human cell lines. Subsequently, cell lines that possess host factors that bind to the HBVCP will lead to transcription as evidenced by the increased expression of GFP. Using this screening method, it was shown that cells from liver (n=5), colon (n=2), stomach (n=2), lymphoid (n=1), lung (n=1), were positive for GFP after transfection with the HBVCP-GFP construct.

Figure 2:
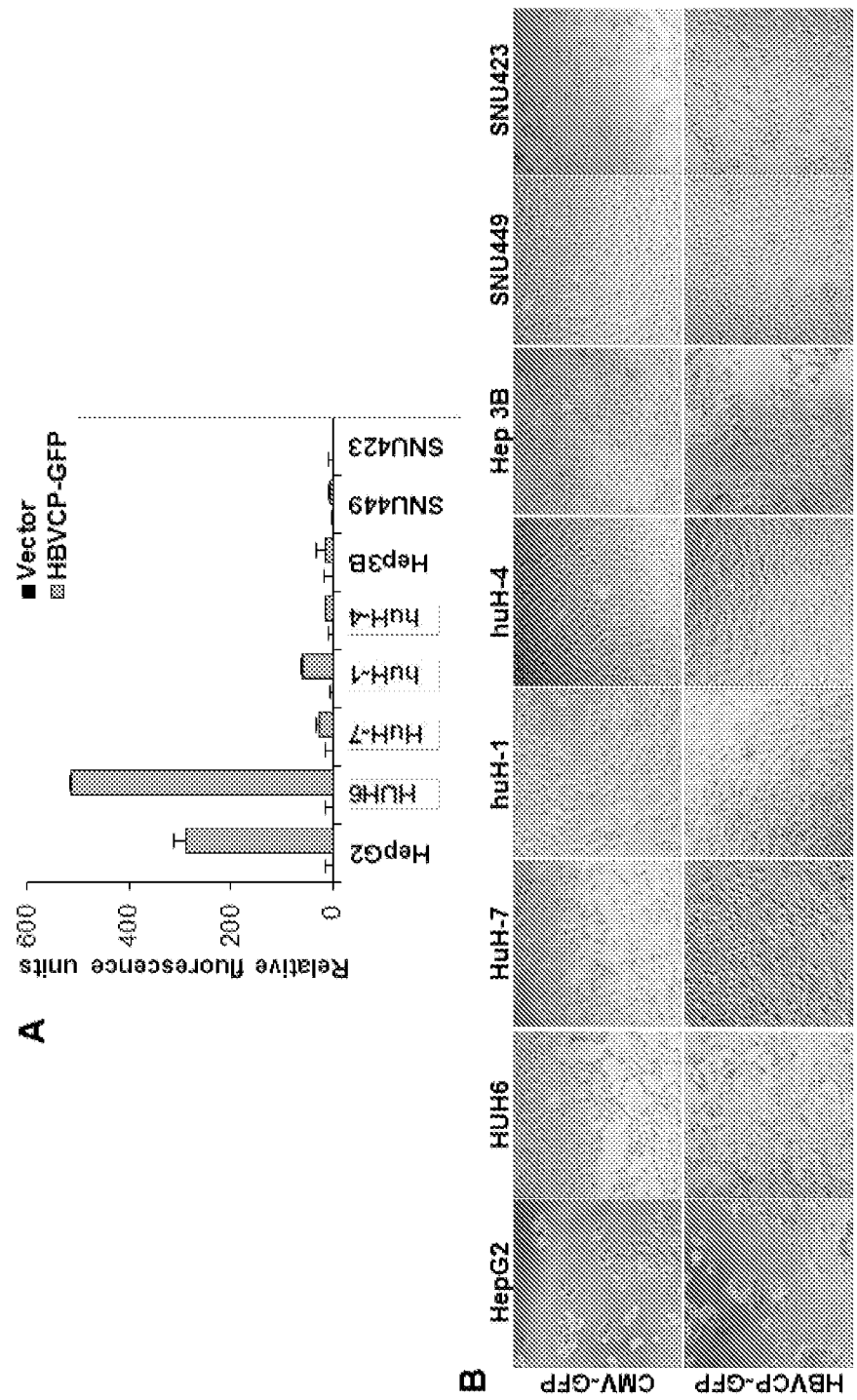
FIG. 2. shows that most liver cell lines are permissive for supporting HBVCP although with varying degrees of efficiency. HepG2, HuH6, HuH7, HuH-4, PLC/PRF/5 were selected for additional studies. HepG2, HuH6 and HuH7 are negative for integrated HBV.
Figure 3A:
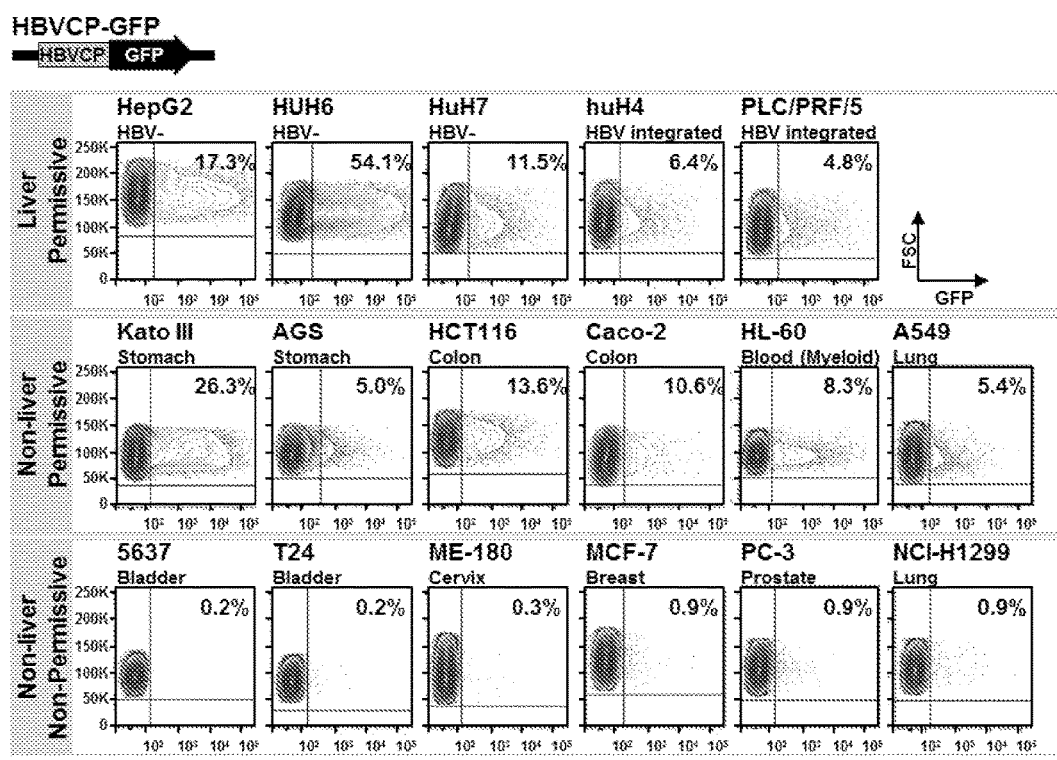
FIG. 3. shows the identification of cell lines that are permissive or not permissive for HBV replication. a) Cells permissive to HBV replication driven by the HBVCP construct are GFP positive by flow cytometry (top panels). b) The transfection control using CMV-GFP shows that all cells are functional by CMV promoter driven expression (lower panels). The data points in both a) and b) show the transfection with GFP vector without promoter inserts.
Figure 3B:
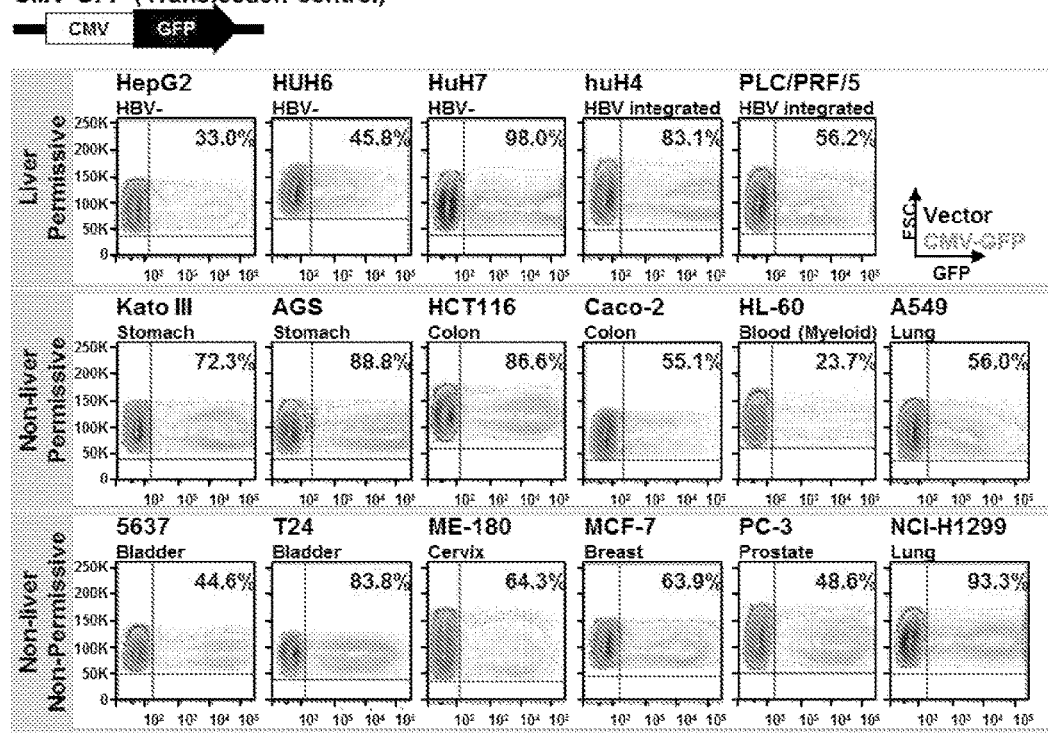

In comparison, a control CMV-GFP vector was able to produce GFP in all cell lines assayed. This demonstrates that the transcription of HBVCP in non-liver permissive cell lines i.e. KATOIII, AGS, HCT116, Caco-2, HL-60 and A549 is authentic (FIGS. 2 and 3).

Accordingly, the discovery of this unusual shared property among a panel of non-liver cell lines is a powerful tool that can be harnessed for the identification of host cellular factors that drive transcription and replication of HBV.

Screening for Host Factors

The transcriptomic profiles of the various cell lines were assayed using Affymetrix GeneChip Human Trancriptome Array 2.0, and differentially expressed genes between permissive (liver, colon, stomach, blood and lung) and non-permissive cell lines (bladder, breast, prostate, cervix, lung) were identified.

Table 5 lists the 50 genes that have the most significant expression level difference between HBV replication permissive (n=11) and non-permissive (n=6). Table 5 list of transcription factors, RNA processing and signalling molecules that were shown to have the most significant correlation values with the efficiency of HBV replication.

Thus, the gene list in Table 5 refers to the set of genes differentially expressed between HBV permissive and HBV non-permissive cells, which when downregulated using siRNAs resulted in an altered HBVCP activity. This suggests that the encoded transcriptional factors or signalling pathway modulators that regulate HBVCP activity of the identified genes or their products may be targeted for controlling HBV replication.

TABLE 5

| GENE ID |
| --- |
| SNAI2 |
| SOX7 |
| ARID3A |
| ATF2 |
| ATF3 |
| ATF4 |
| CALCOCO1 |
| CHD3 |
| CPD |
| CSNK2A2 |
| CNOT11 |
| DCP1A |
| DDX39B |
| DYRK1B |
| E2F6 |
| E2F7 |
| EPAS1 |
| FOXN2 |

TABLE 5-continued

| GENE ID |
| --- |
| HIVEP2 |
| HERPUD1 |
| KPNA3 |
| KANK2 |
| LIN54 |
| NCL |
| PAK1IP1 |
| PNPT1 |
| POLR3E |
| PRDX3 |
| PTP4A1 |
| RNASEH2A |
| RHOB |
| RNF4 |
| RNF43 |
| SERBP1 |
| SKA1 |
| SMAD3 |
| SRPK1 |
| STAM |
| STRADB |
| SSB |
| STT3B |
| TFAP2A |
| TFAP2C |
| TFB2M |
| TP73 |
| TRIM24 |
| TRIM68 |
| TRIM27 |
| WDR54 |
| ZNF518A |

Validation Assay (siRNA with Luciferase Readout)

HepG2 cells were treated with siRNA and transfected with the HBVCP-luciferase construct to assess the functional role of these factors in the activity of the HBVCP. Table 6 outlines the results and the effect of the siRNA treatment on HBVCP activity as reflected by the luciferase expression level detected (TBC=to be confirmed).

TABLE 6

| GENE ID | Luciferase Expression |
| --- | --- |
| SNAI2 | 1.65 |
| SOX7 | 2.08 |
| ARID3A | 0.22 |
| ATF2 | 0.16 |
| ATF3 | 0.48 |
| ATF4 | 0.43 |
| CALCOCO1 | 0.25 |
| CHD3 | 1.08 |
| CPD | 0.35 |
| CSNK2A2 | 0.33 |
| CNOT11 | 0.50 |
| DCP1A | 0.16 |
| DDX39B | 0.12 |
| DYRK1B | 0.26 |
| E2F6 | 2.96 |
| E2F7 | 0.58 |
| EPAS1 | 0.89 |
| FOXN2 | 0.54 |
| HIVEP2 | 0.64 |
| HERPUD1 | 0.29 |
| KPNA3 | 0.34 |
| KANK2 | 0.48 |
| LIN54 | 0.64 |
| NCL | 0.43 |
| PAK1IP1 | 0.38 |
| PNPT1 | 0.33 |
| POLR3E | 0.63 |
| PRDX3 | 0.45 |
| PTP4A1 | 0.16 |
| RNASEH2A | 0.51 |

TABLE 6-continued

| GENE ID | Luciferase Expression |
|---|---|
| RHOB | 0.22 |
| RNF4 | 0.34 |
| RNF43 | 0.33 |
| SERBP1 | 0.56 |
| SKA1 | 0.41 |
| SMAD3 | 0.44 |
| SRPK1 | 0.38 |
| STAM | 0.19 |
| STRADB | 0.24 |
| SSB | 0.43 |
| STT3B | 0.08 |
| TFAP2A | 0.71 |
| TFAP2C | 0.75 |
| TFB2M | 0.41 |
| TP73 | 0.40 |
| TRIM24 | 0.75 |
| TRIM68 | 0.88 |
| TRIM27 | 1.50 |
| WDR54 | 0.42 |
| ZNF518A | 0.26 |

Validation Assay—(siRNA with HBV pgRNA Readout)

Various cell lines were transfected with a HBV full length (1.1×) replicon and the efficacy of the transfection was evaluated.

The results showed that non-liver cell lines such as Kato III (stomach), HCT116, Caco-2 (colon) were able to support the generation of the full length HBV genome (FIG. 4).

Figure 5:
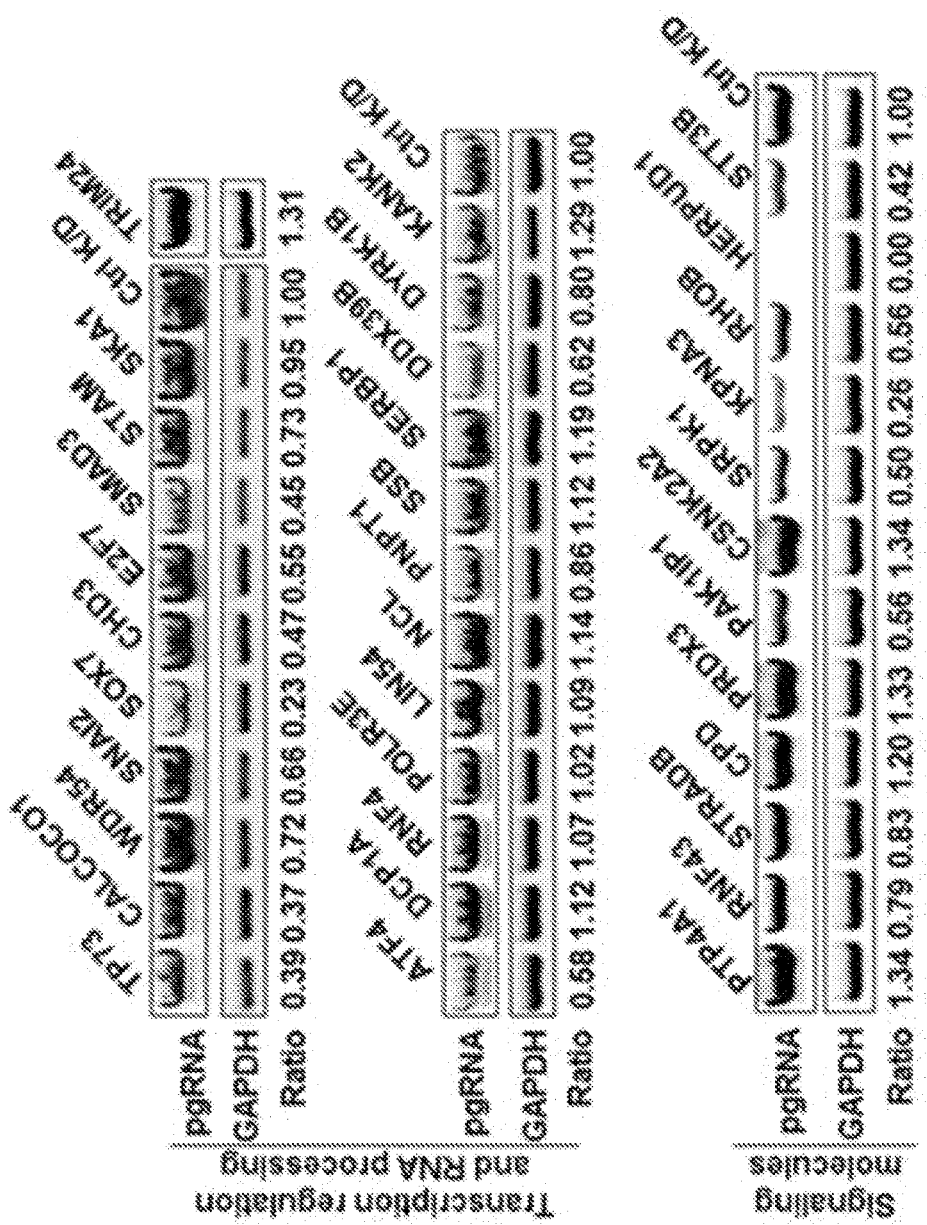
FIG. 5. shows that the treatment with siRNAs specific for candidate genes affects the efficacy of replicon transfection in HepG2 cells.

HepG2 cells were treated with siRNA and transfected with the HBV replicon. Consequently, genes that were shown to be down-regulated by the siRNA treatment and associated with reduced pgRNA levels were compared to controls. The results suggested that the replication of the complete HBV viral genome is affected by these genes (FIG. 5).

Table 7 shows that each target (shown as gene code) is tested by both overexpression and inhibition of expression. In order to satisfy these stringent criteria, the overexpressed target should enhance HBV replication, and the downregulation of the target will result in the reduction of HBV replication. Among our earlier, 50 gene list, some 80-90% of targets do not meet this stringent criteria.

Accordingly, genes that are promising targets for modulating HBV replication are recognised as either modulating HBVCP activity and/or modulating pgRNA expression when down-regulated or over-expressed. In this regard, the genes in Tables 6 and 7 were shown to meet such screening criteria and hence have the potential for developing agents/therapeutics for modulation of HBV replication.

TABLE 7

| | Over-expression | | siRNA knock-down | |
|---|---|---|---|---|
| Gene code | HBVCP-Luc | pgRNA | HBVCP-Luc | pgRNA |
| EPAS1 | 2.5 | 1.3 | 0.3 | 0.8 |
| PAK1IP1 | 3.2 | 6.2 | 0.3 | 0.9 |
| TRIM27 | 2.8 | 4.0 | 1.1 | 0.8 |
| TFAP2A | 2.2 | 1.7 | 0.3 | 0.3 |
| WDR54 | 2.0 | 1.4 | 0.3 | 0.7 |
| SRPK1 | 1.6 | 0.9 | 0.3 | 0.2 |
| PNPT1 | 1.5 | 0.8 | 0.3 | 1.6 |
| SMAD3 | 1.6 | 1.7 | 0.3 | 0.5 |
| STRADB | 1.3 | 3.0 | 0.3 | 0.4 |
| SNAI2 | 0.5 | 0.3 | 0.7 | 1.6 |
| ATF4 | 1.0 | 1.7 | 0.1 | 0.8 |
| SKA1 | 0.3 | 1.2 | 0.3 | 0.5 |

Example 2

Development of a HBV Transcription Screen

Figure 6:
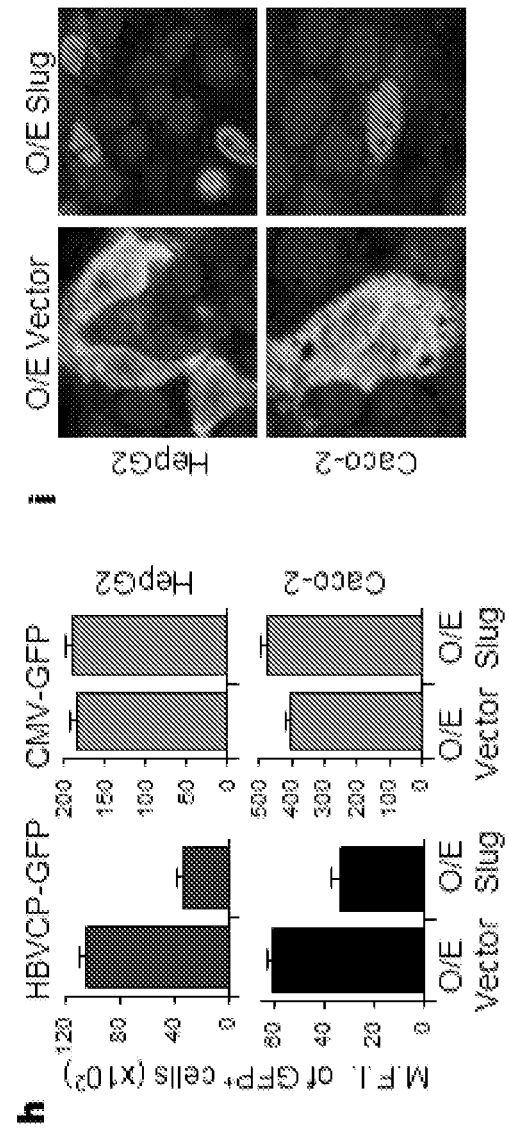
FIG. 6 shows that Slug specifically suppresses HBV replication. a) HBVCP activity in liver and non-liver cell lines using GFP reporter. The cells were divided into HBV permissive or non-permissive groups based on percentage GFP+ cells; b) pgRNA is expressed exclusively in HBV permissive cells transfected with HBV replicon. GAPDH was used as loading control; c) Principal component analysis (PCA) of cell lines from HTA. Liver HBV permissive, non-liver HBV permissive and non-liver HBV non-permissive cells form distinct clusters; d) Slug binding motif in the BCP completely overlaps the pgRNA initiator. Numbers denote nucleotide positions of HBV genotype A; e) Relative expression of full-length SNAI2 (Slug) by RTPCR; f) Slug binds specifically to HBVCP in sequence-dependent manner. HBVCP-Slug complex formed from wildtype probe bearing the Slug motif generated a weak band that intensified with Slug overexpression (O/E). The complex was abolished with mutant Slug motif; g) Overexpressed Slug significantly suppressed HBVCP-dependent transcription in HBVCP-Luc transfected permissive cells; h) Slug overexpression specifically suppressed HBVCP transcription activity to reduce mean fluorescence intensity (M.F.I.) of GFP+ cells in HBVCP-GFP but not CMV-GFP control cells; i) HBV permissive cells overexpressing Slug have negligible staining for HBcAg; j) Slug overexpression diminishes pgRNA when co-transfected with HBV replicon.
Figure 6A:
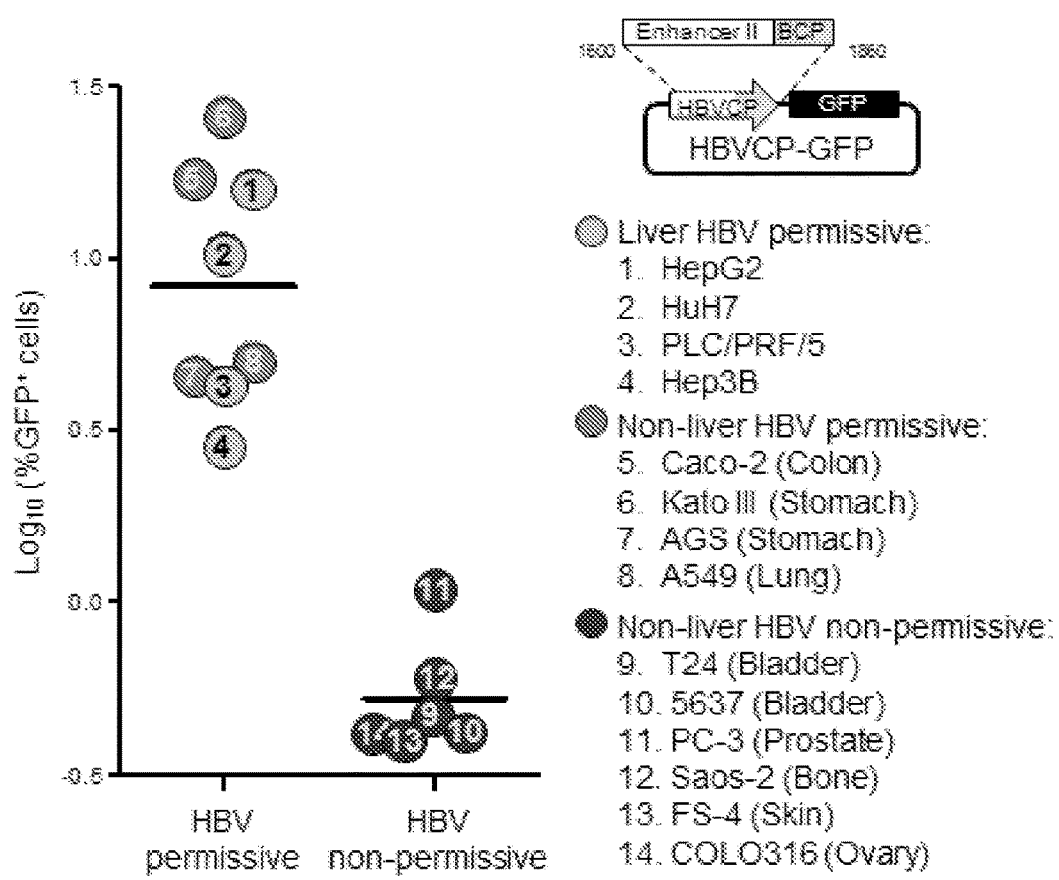
Figure 10C:
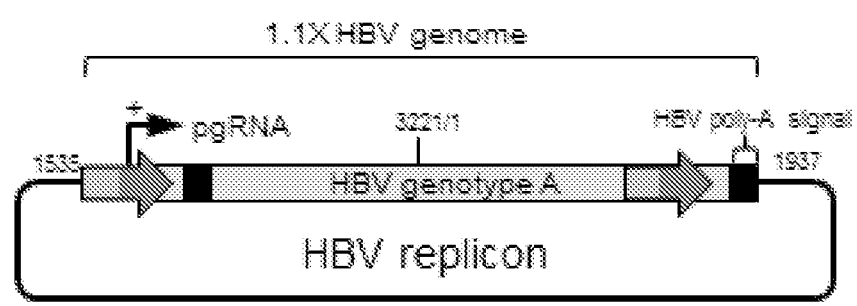
Figure 10D:
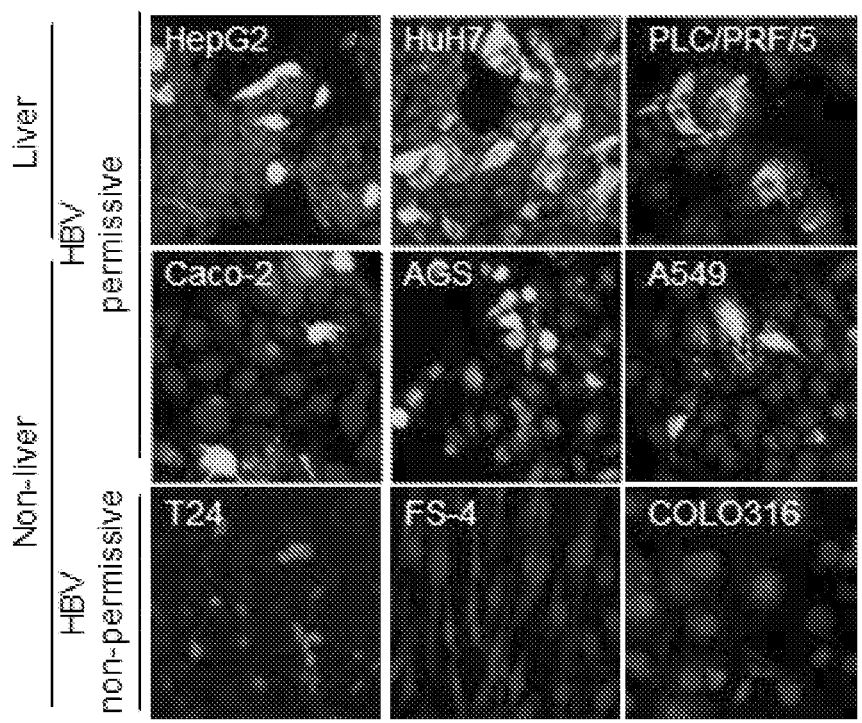

To identify tissue restrictive host transcription factors, as in Example 1 described herein, a GFP reporter construct driven by HBVCP was transfected into a panel of liver and non-liver cell lines (n=14, FIG. 6a). Surprisingly, besides liver cell lines, colon (Caco-2), stomach (Kato III, AGS) and lung (A549) cells were also GFP-positive. Other non-liver cells derived from bladder, prostate, bone, ovary and skin had negligible GFP expression. All non-liver cells lack albumin and transferrin (FIG. 10a), and were GFP-positive with the CMV-GFP control (FIG. 10b). A whole-virus replicon (FIG. 10c) transcribed pgRNA (FIG. 6b) and generated HBcAg (FIG. 10d) in permissive liver and non-liver cells, indicating that the host cellular milieu supporting HBV replication are similarly present in liver and selected non-liver cells.

Screening for Host Factors

Figure 6D:
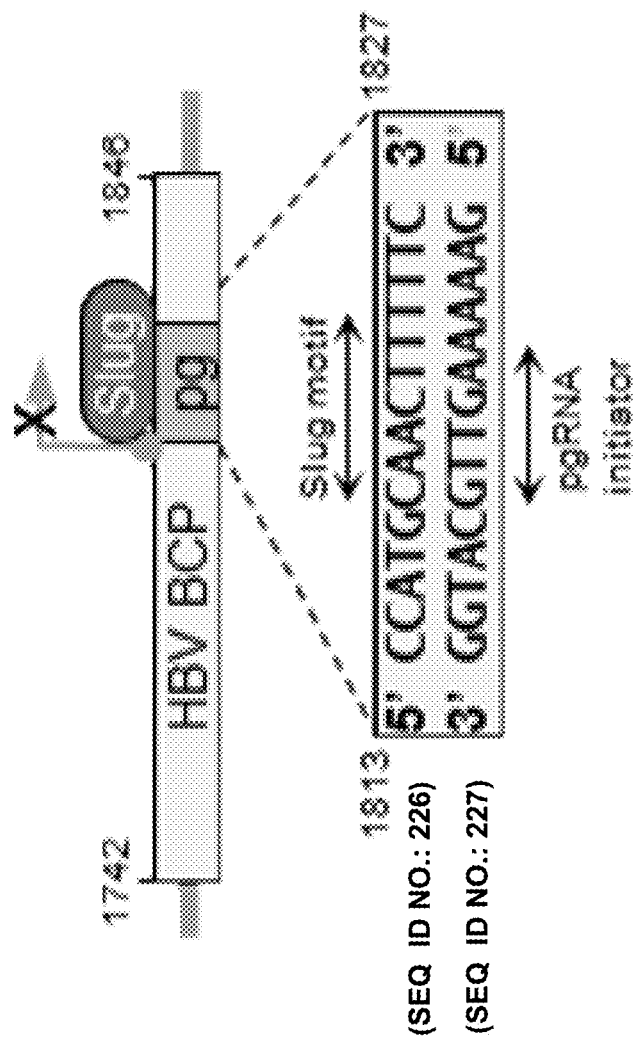
Figure 11A:
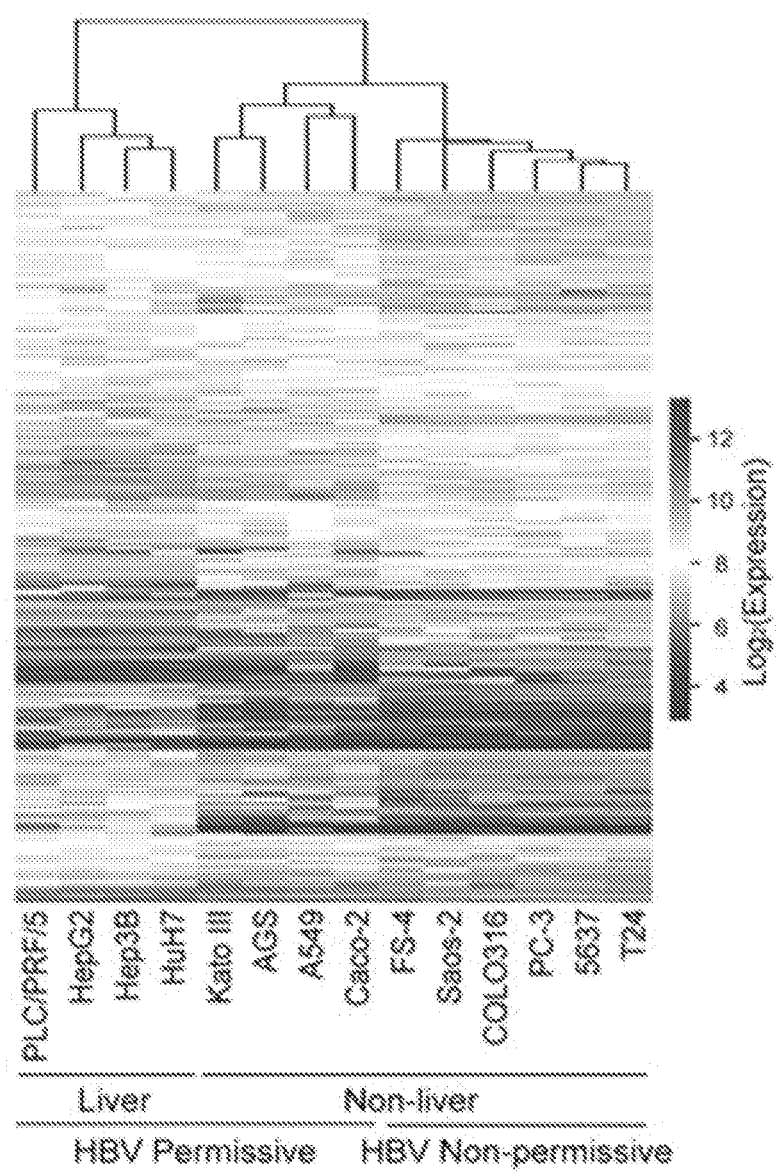
FIG. 11 shows a human transcriptome array. a) Unsupervised hierarchical clustering of HBV permissive and non-permissive cells by relative expression of differentially expressed protein coding transcripts; b) Number of genes differentially expressed between HBV permissive and non-permissive cell clusters.
Figure 11B:
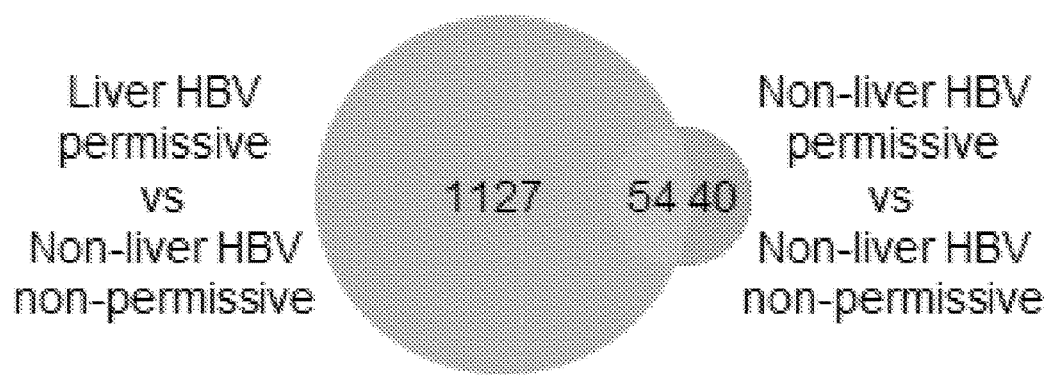
Figure 12A:
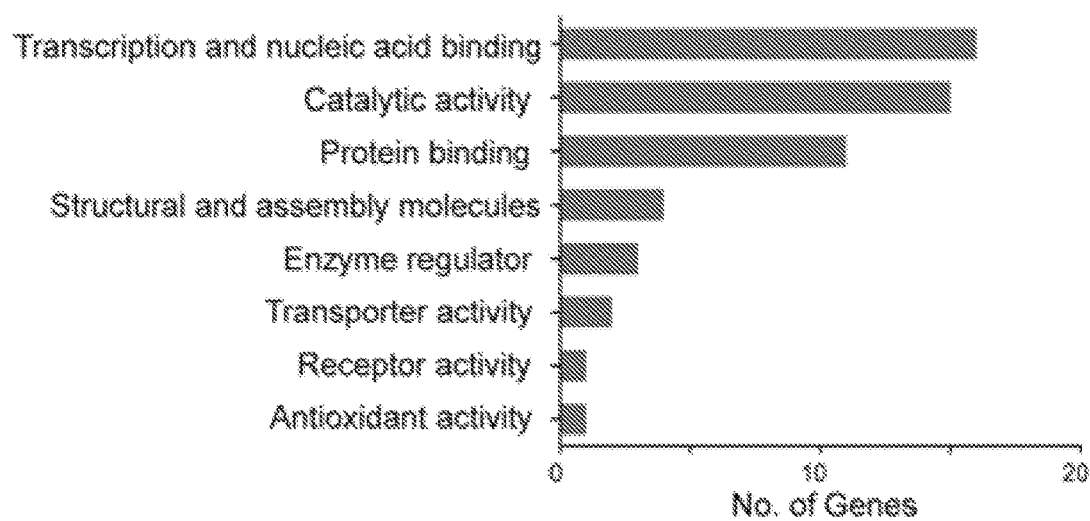
FIG. 12 shows genes differentially expressed between HBV permissive and HBV non-permissive cells. a) Genes differentially expressed between HBV permissive and HBV non-permissive cells categorized by biological functions defined using GO (Gene Ontology) terms; b) Relative mRNA transcript expression of transcription factors differentially expressed between HBV permissive and non-permissive cells.

Transcriptomic profiles for all 14 cell lines (Affymetrix HTA 2.0, (FIG. 11a) revealed 3 distinct cell clusters: liver HBV permissive, non-liver HBV permissive and non-liver HBV non-permissive (FIG. 6c). Comparison of differential gene expression signatures between the 2 permissive and non-permissive combinations showed 54 overlapping genes as shown in Table 8 (FIG. 11b, 12a), of which only SNAI2 (FIG. 6d) and HNF4α have corresponding DNA binding motifs within the HBVCP (FIG. 7c) and were thus chosen for further investigation as promising targets for modulating HBV replication.

Thus, the gene list in Table 8 refers to the genes that are differentially regulated between HBV permissive and HBV non-permissive cells, but their expression correlates significantly with the property of HBV permissiveness in the cells.

TABLE 8

| GENE ID |
|---|
| C1orf131 |
| ETS1 |
| HNF4A |
| FSTL1 |
| INHBA |
| KCTD12 |
| MAK16 |
| NOSTRIN |
| PNPT1 |
| PTCD3 |
| SEMA4G |
| SNAI2 |
| SNRPD1 |
| SUSD1 |
| WDR43 |
| ZFHX4 |
| ALDH2 |
| ALDH5A1 |
| B3GNT2 |
| CHUK |
| DDX18 |
| EPT1 |
| ERMP1 |
| GCNT3 |
| GSR |
| HMGCS1 |
| NAE1 |
| PDSS1 |
| PPID |
| SMURF2 |
| TANC2 |
| BCAR3 |
| C16orf70 |
| C9orf100 |

TABLE 8-continued

GENE ID

EPB41L5
HSPA14
HSPA9
LRP12
NSMCE4A
NUP35
PSMD11
RNF43
EXOC6
FUZ
STOML2
WASF2
ARHGAP12
MYO9B
TBC1D14
FLVCR1
SLC39A14
GPX2
IDH1
FAM35A

Example 3

SNAI2 (Snail)

Figure 6E:
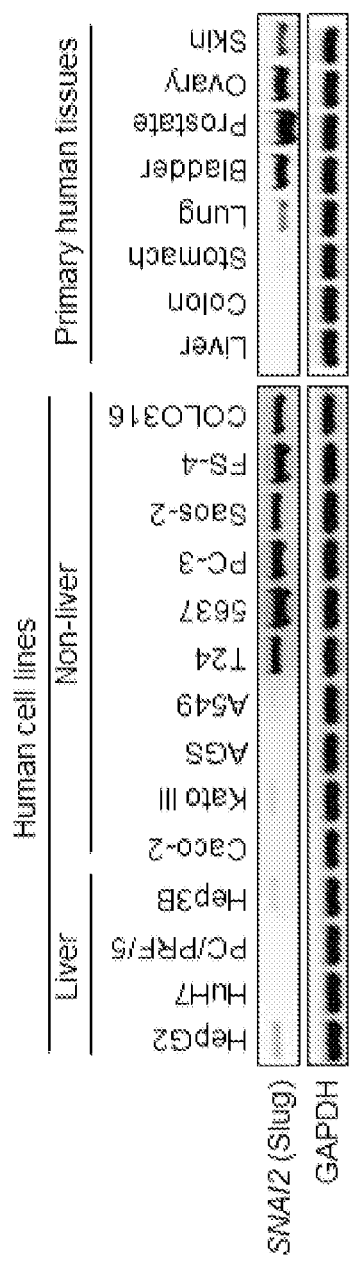
Figure 13:
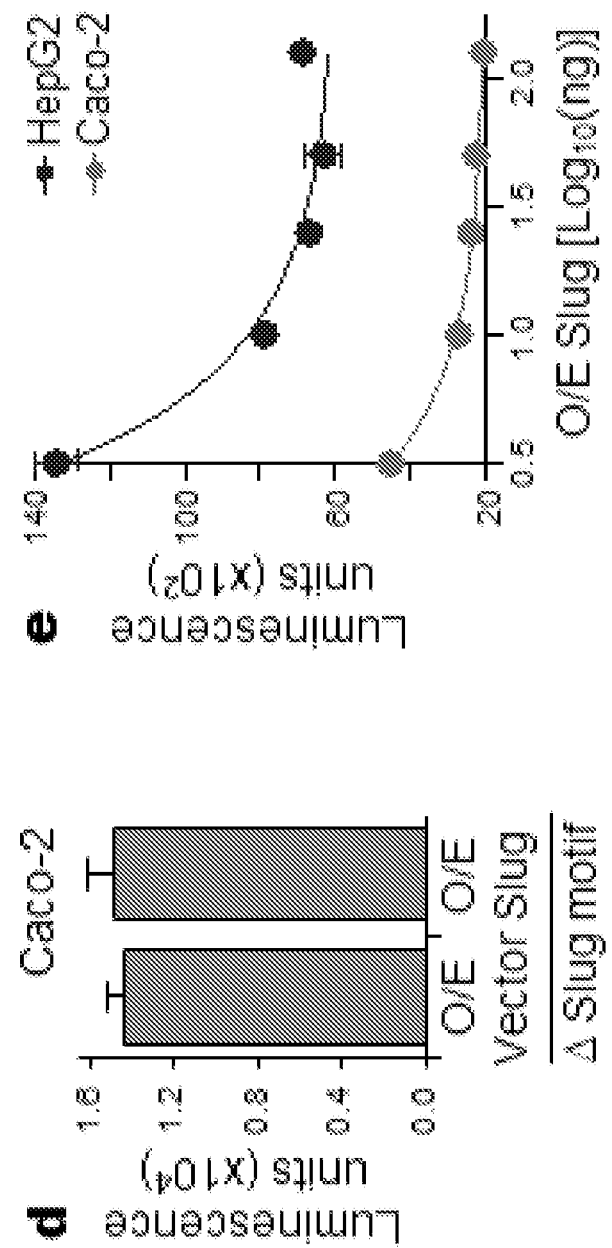
FIG. 13 shows that Slug is a specific transcription repressor at the HBVCP. a) SNAI2 gene expression by HTA 2compared with other Snail family genes SNAI1 and SNAI3; b) Slug exerts its repressive effect on HBVCP transcription activity in a motif dependent manner, as motif deletion increased transcription at the HBVCP; c) Slug motif mutations increase HBVCP activity in HepG2 and Caco-2 permissive cells, suggesting that the repressive activity of Slug is motif sequence-dependent; d) Effect of Slug motif deletion on HBVCP activity with overexpressed Slug in luciferase reporter assay; e) Dose-dependent effect of Slug overexpression on transcription by luciferase reporter assay.
Figure 13A:
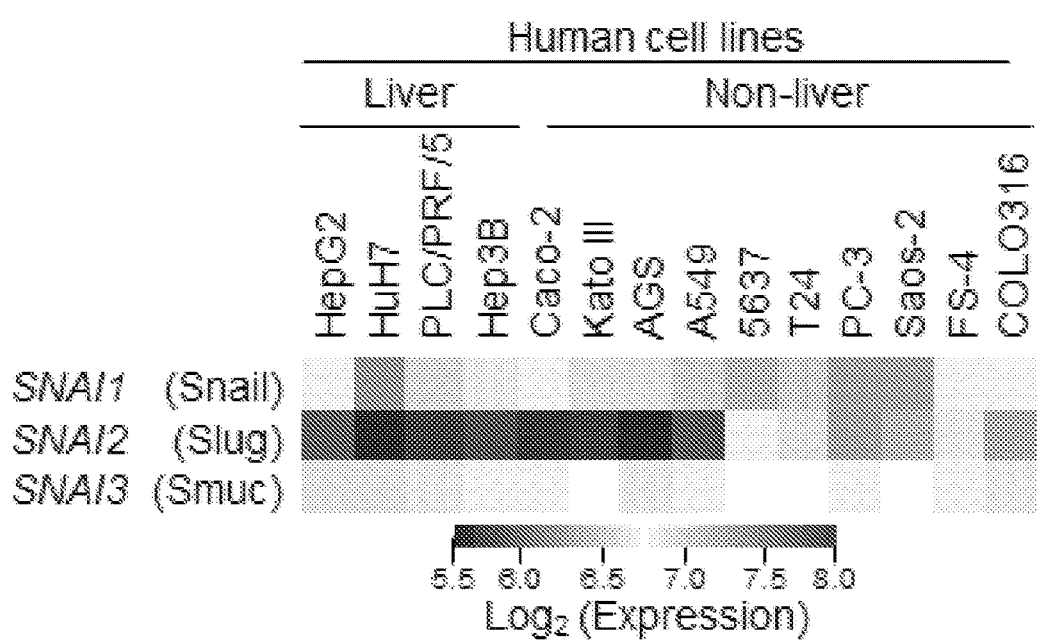

SNAI2 codes for Slug, a member of snail protein family of zinc finger transcription factors. Its homologs SNAI1 (Snail) and SNAI3 (Smuc/ZNF293) showed no correlation with HBV permissiveness (FIG. 13a). Slug expression was high in non-permissive cells while low/absent in permissive cells; and this pattern was similarly exhibited in corresponding primary human tissues (FIG. 6e).

Figure 6F:
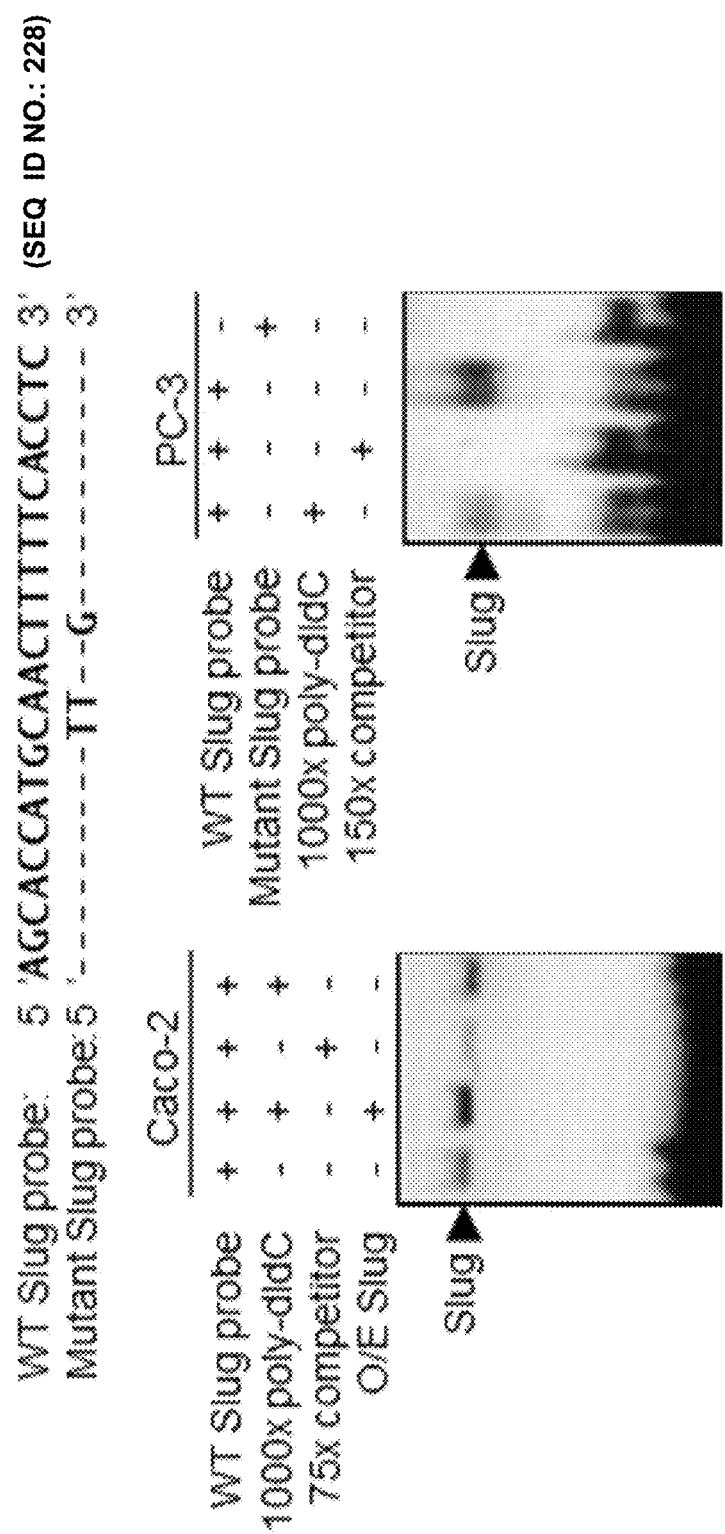
Figure 6G:
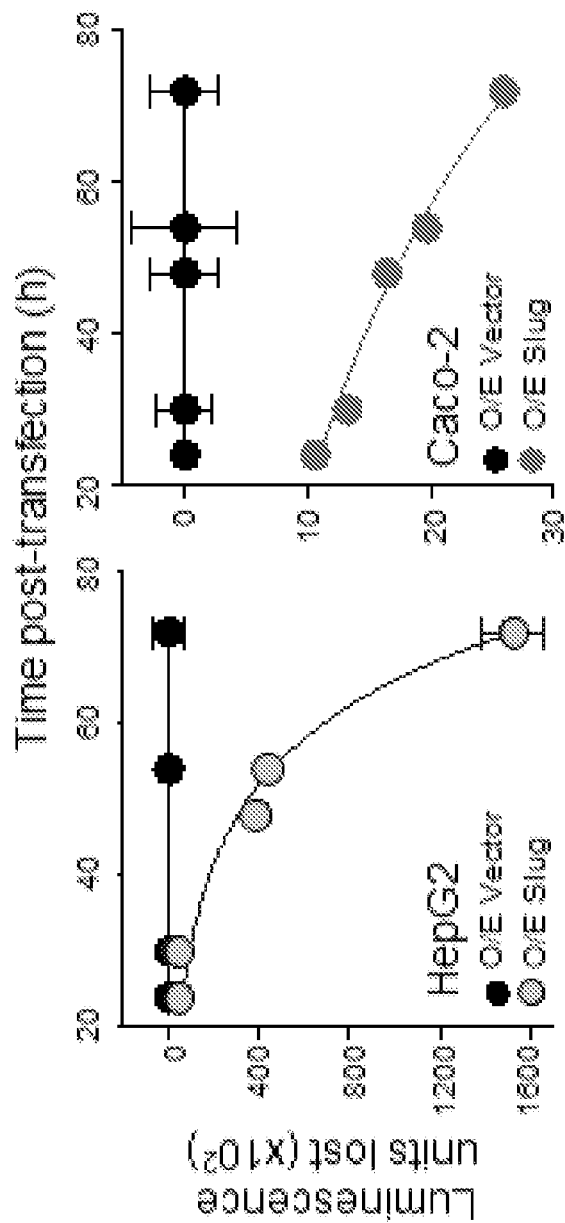
Figure 13B:
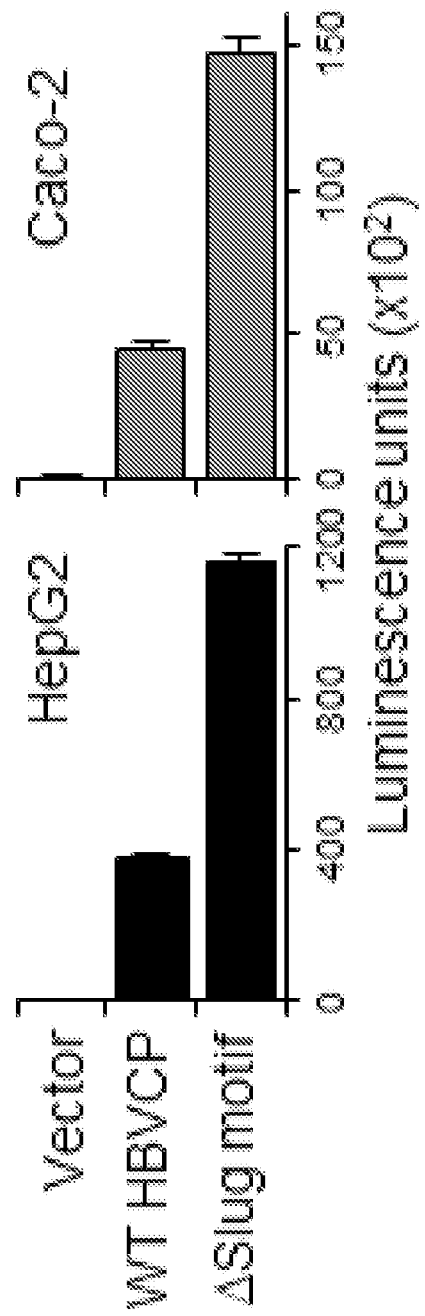
Figure 13C:
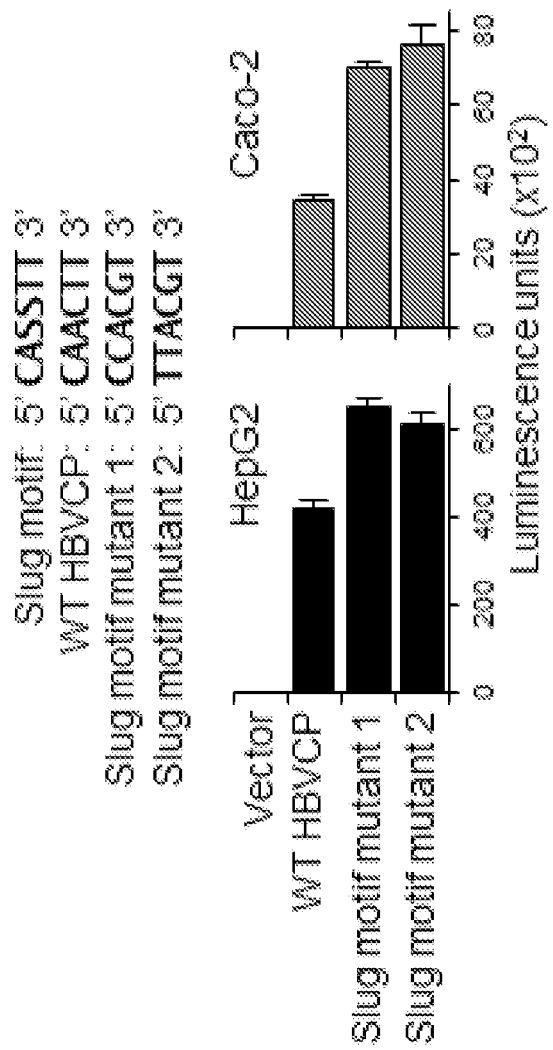

Slug binds to the E-box recognition motif which overlaps the pgRNA initiator within the basal core promoter (BCP) of HBVCP (FIG. 6d), indicating that Slug binding may interfere with pgRNA initiation. Its HBVCP repressive role was verified when HBVCP activity was shown to increase by deleting the 6 bp motif (FIG. 13b) or mutating its cognate binding motif from "CAACTT" to "TTACGT" which was also confirmed by loss of EMSA binding (FIG. 6f, FIG. 13c). Motif deletion rendered the HBVCP insensitive to the effects of Slug overexpression (FIG. 13d), which at the wild-type HBVCP resulted in a dose-dependent transcription repression (FIG. 6g, FIG. 13e) but not in the CMV-GFP control (FIG. 6h).

The whole virus replication was effectively inhibited as Slug overexpression in HBV permissive cells shut down HBcAg expression (FIG. 6i) and markedly reduced pgRNA in primary human hepatocytes (FIG. 6j). Taken together, these results provide strong evidence that Slug blocks pgRNA initiation at the HBVCP, arresting HBV replication.

HNF4α and Isoforms

Figure 12B:
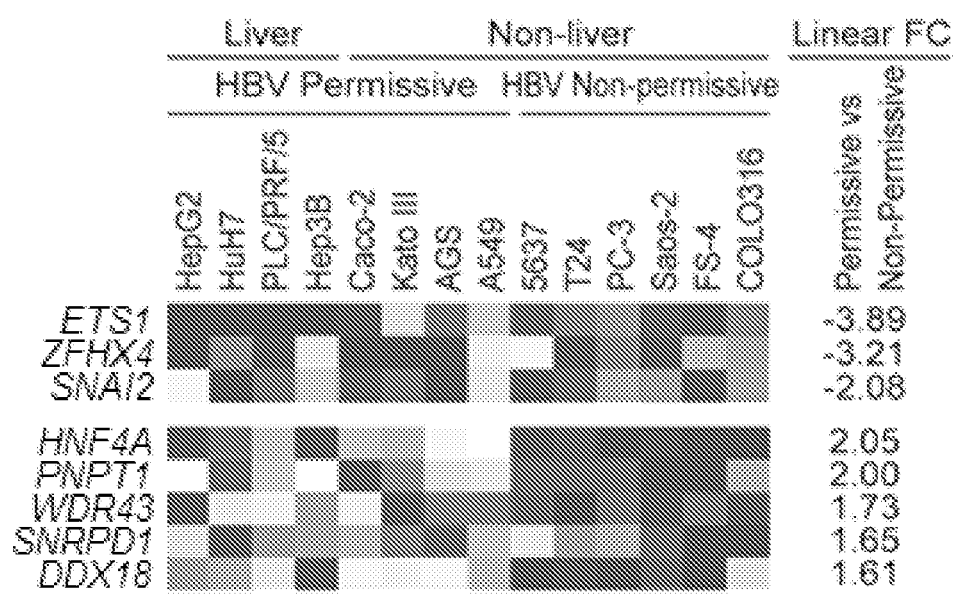
Figure 14A:
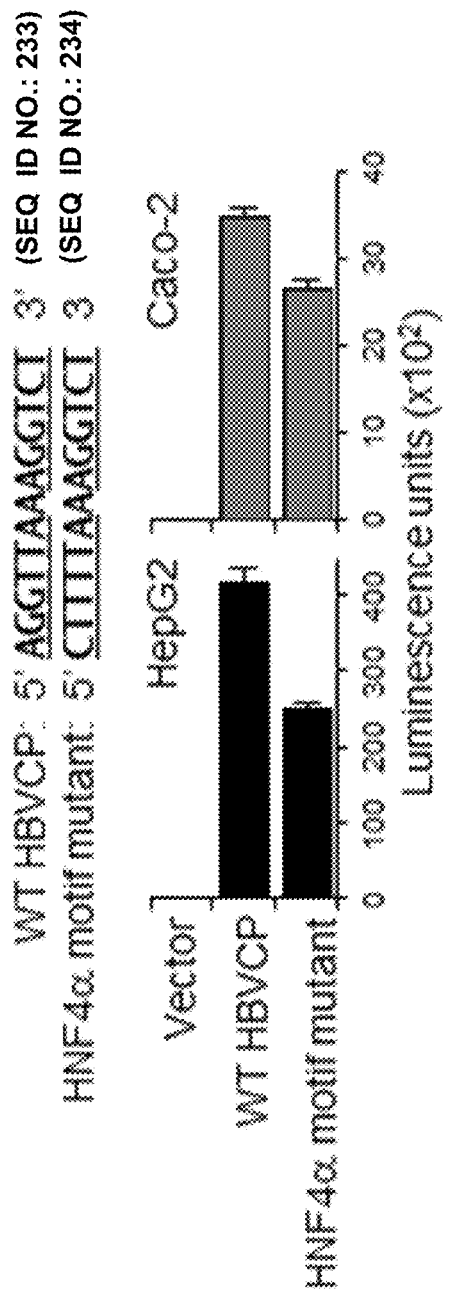
FIG. 14 shows differentially expressed HNF4α isoforms determine HBVCP activity within permissive cells. a) HNF4α homo-dimer binds to its motif in the HBVCP characterized by two half-sites (underlined) separated by a single nucleotide spacer. Mutation to the 5' half-site is sufficient to reduce transcription at the HBVCP; b) Differential expression of HNF4A gene exons in cells by HTA. Exons are indicated as bars, with protein coding sequences represented as thicker bars than the 5'UTRs and 3'UTRs. The signal for probe set 3 detecting for coding sequence of exon 2 utilized in HNF4α1, HNF4α2 and HNF4α3 is higher in liver cells than non-liver cells, which is consistent with western blot data. The signal for probe set 13 detecting for HNF4α1, HNF4α2, HNF4α7 and HNF4α8 is high in HBV permissive cells, but probeset 14 detecting for exon 10 in HNF4α2 and HNF4α8 is not differentially expressed between HBV permissive and non-permissive cells, together suggesting that HNF4α1 is preferentially expressed in HBV permissive cells. There is marginally higher signal for probeset 12 which detects for exon 9 utilized in HNF4α3 and HNF4α9 in HBV permissive cells; c) Summary of exon array data for HNF4A gene suggesting that in contrast to HNF4α2 and HNF4α8, HNF4α1/3/7/9 correlate with permissibility of cells for HBV replication; d) Schematic of functional domains of HNF4αisoforms. HNF4αprotein isoforms share conserved DNA-binding and ligand-binding domains but differ in their N- and C-termini bearing the F-domain. Predicted molecular weights are indicated. AF-1: Activating function 1, co-factor interacting domain; e) Detection of individually overexpressed HNF4α isoforms in nuclear lysates using antibody clones specific to distinct N-termini; f) Expression of HBcAg in cells overexpressing individual isoforms of HNF4α by immunofluorescence microscopy. Cell nuclei are stained by DAPI.

HNF4α displayed mutually exclusive pattern of mRNA expression with Slug (FIG. 12b) which is validated at protein level (FIG. 7a), suggesting that they function in opposing fashion. Consistent with its role as an activator at the HBVCP, mutating the 5' half-site "AGGTTA" of the hepatocyte nuclear factor 4 alpha (HNF4α) binding motif within enhancer II reduced transcription at the HBVCP (FIG. 14a).

Figure 7A:
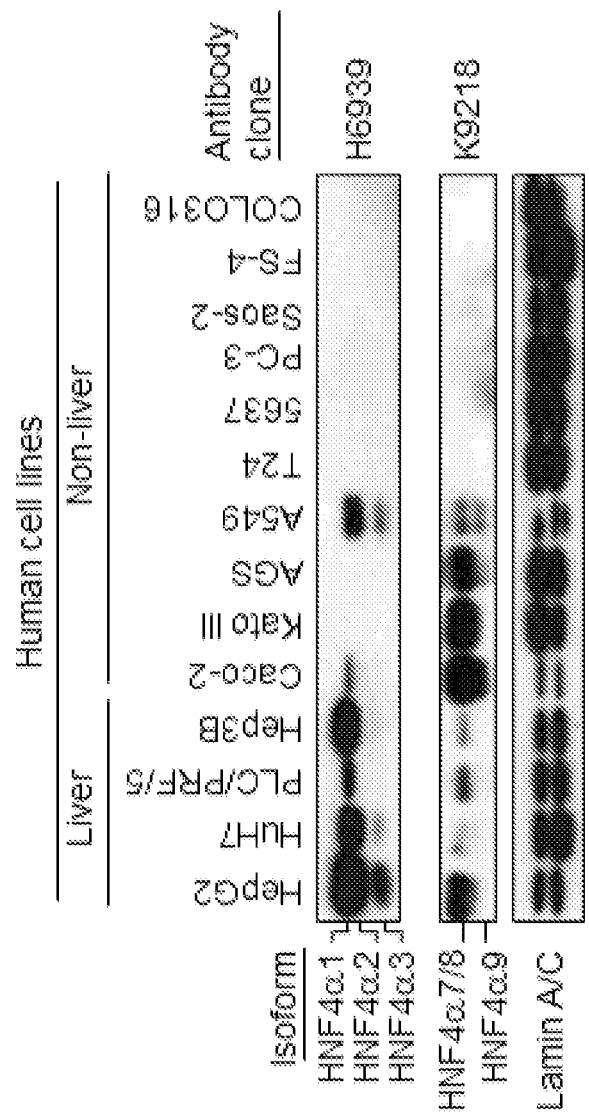
FIG. 7. shows that Sox7 specifically represses HBV replication by blocking HNF4α-HBVCP interaction. a) Western blot of endogenous HNF4α isoform expression in cells using antibodies specific to distinct N-termini; b) Dose-dependent effect of HNF4α isoform on transcription at the HBVCP using HBVCP-Luc reporter; c) HNF4α and Sox7 binding motifs overlap by 1 nt and are found in enhancer II; d) Sox7 forms a specific DNA-protein complex with wildtype HBVCP probe which diminishes when Sox7 motif is mutated. Intensity of band for HNF4α3-HBVCP complex increases when a 3 nt-spacer is inserted between the HNF4α and Sox7 binding motifs; e) Sox7 specifically diminishes M.F.I. of GFP+ cells co-transfected with HBVCP-GFP but not CMV-GFP controls; f) Sox7 overexpression significantly suppressed transcription at the HBVCP in HBVCP-Luc transfected cells; g) Effect of Sox7 overexpression on HBcAg expression by immunofluorescence staining; h) Effect of Sox7 overexpression on pgRNA in primary human hepatocytes and permissive cell lines transfected with HBV replicon.
Figure 7B:
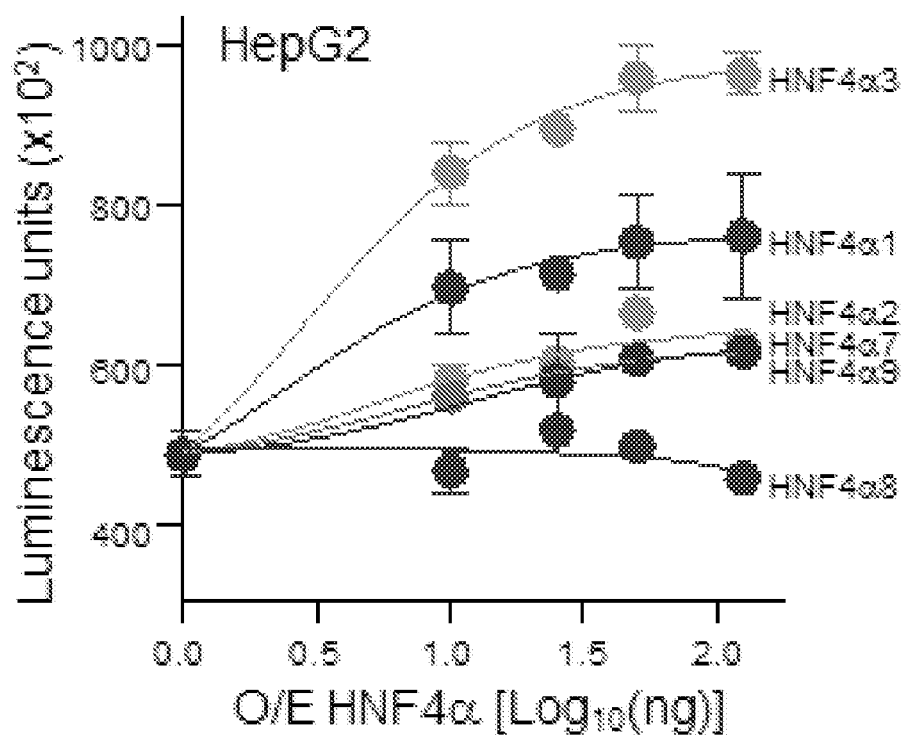
Figure 14B:
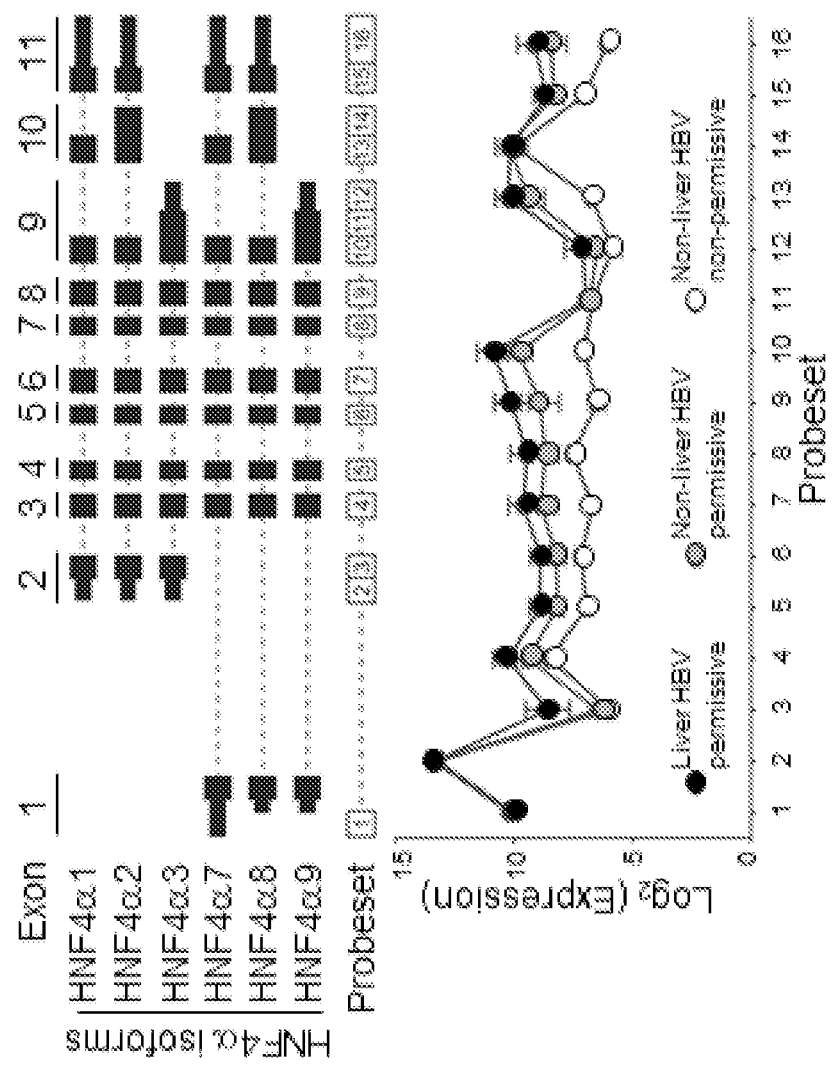
Figure 14C:
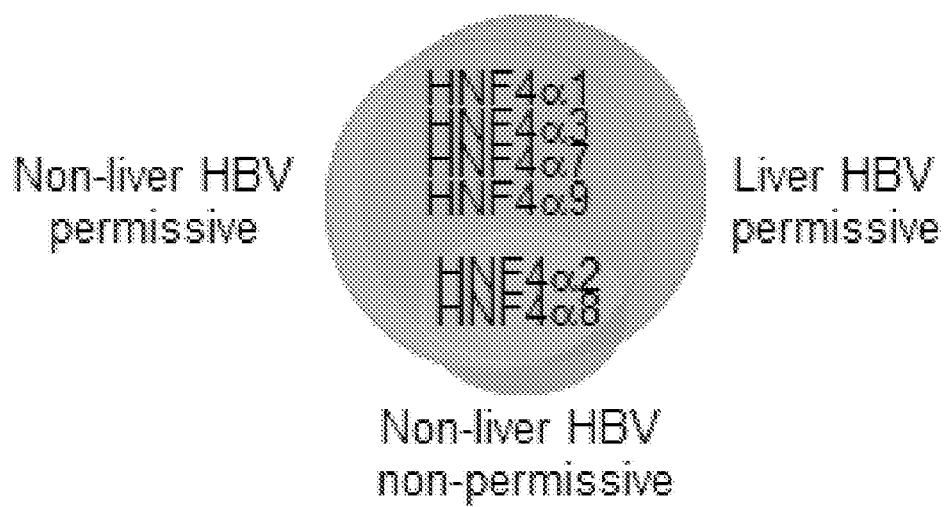
Figure 14D:
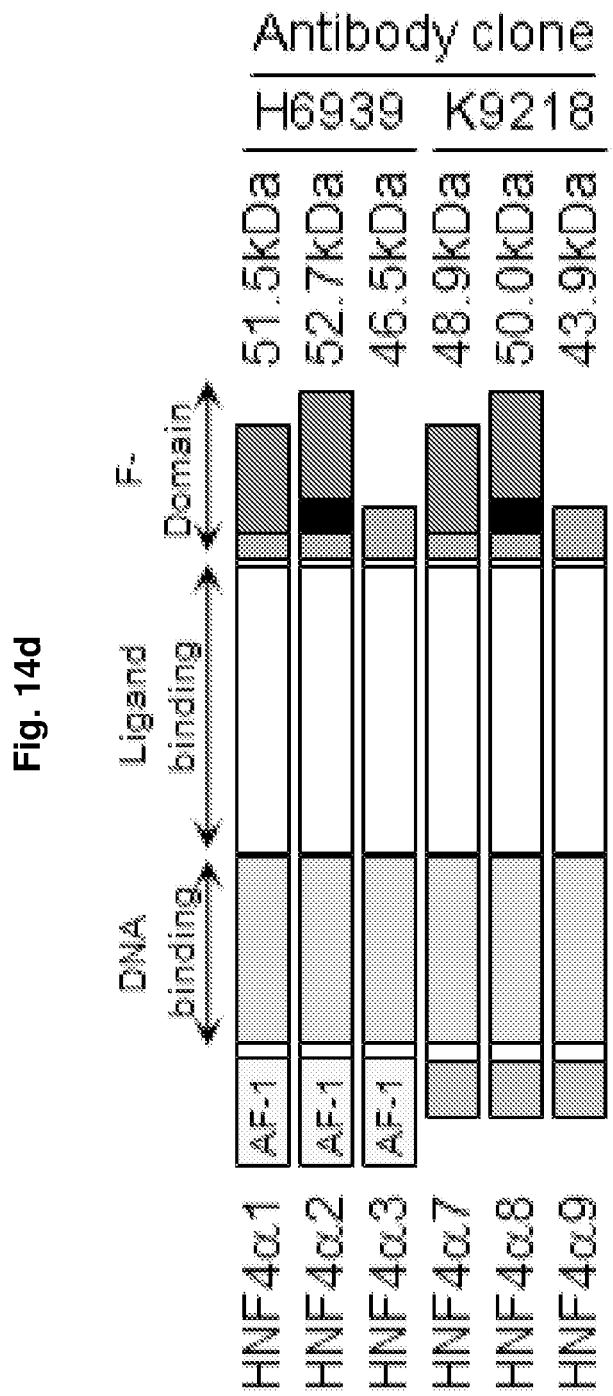
Figure 14E:
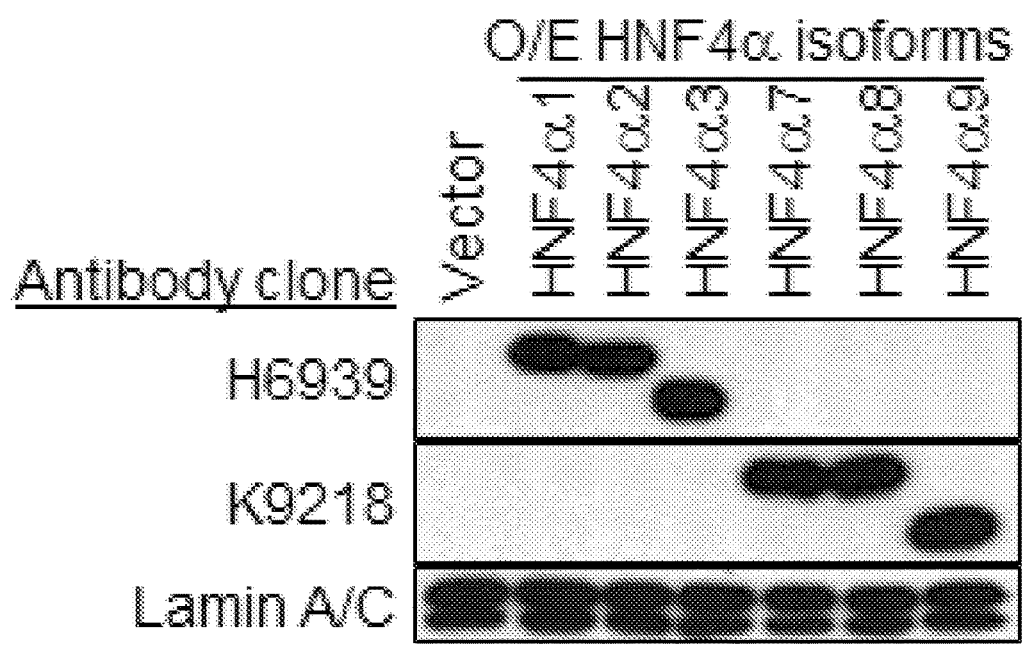
Figure 14F:
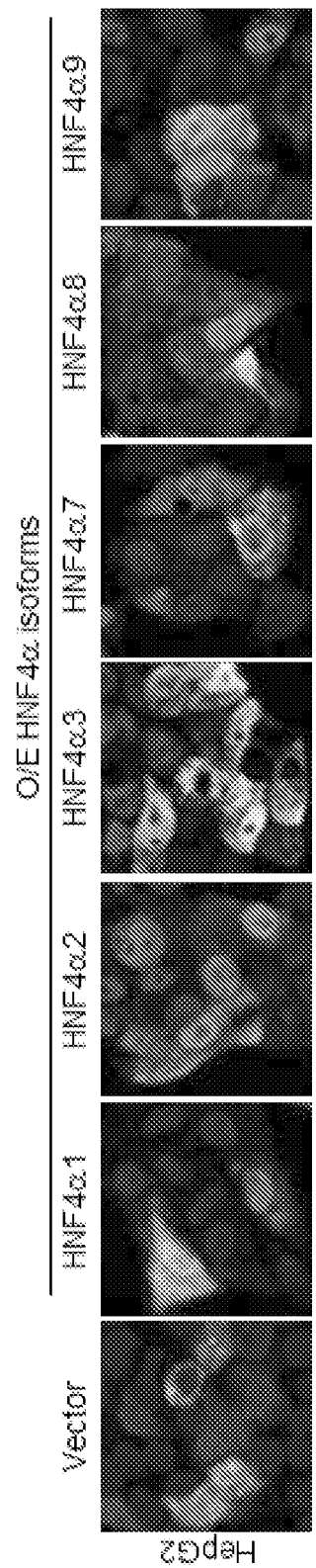

As HNF4α isoforms are differentially expressed between permissive and non-permissive cells (FIG. 14b,c,d). Functional comparison of six cloned isoforms (FIG. 14e) revealed that HNF4α3 and HNF4α1 were more potent in driving HBVCP activity (FIG. 7b), correlating well with HNF4α1 being the constitutive dominant isoform in liver cells (FIG. 7a). The less potent HNF4α7/8/9 isoforms prevailed in non-liver permissive Kato III, Caco-2 and AGS. This relationship was ascertained by finding that overexpressed nuclear HNF4αisoform correlated with its anticipated HBcAg expression (FIG. 14f).

Therefore expression of specific HNF4α isoforms in different tissues was shown to regulate the efficiency of HBV transcription.

Sox7 and interaction with HNF4α

Figure 7C:
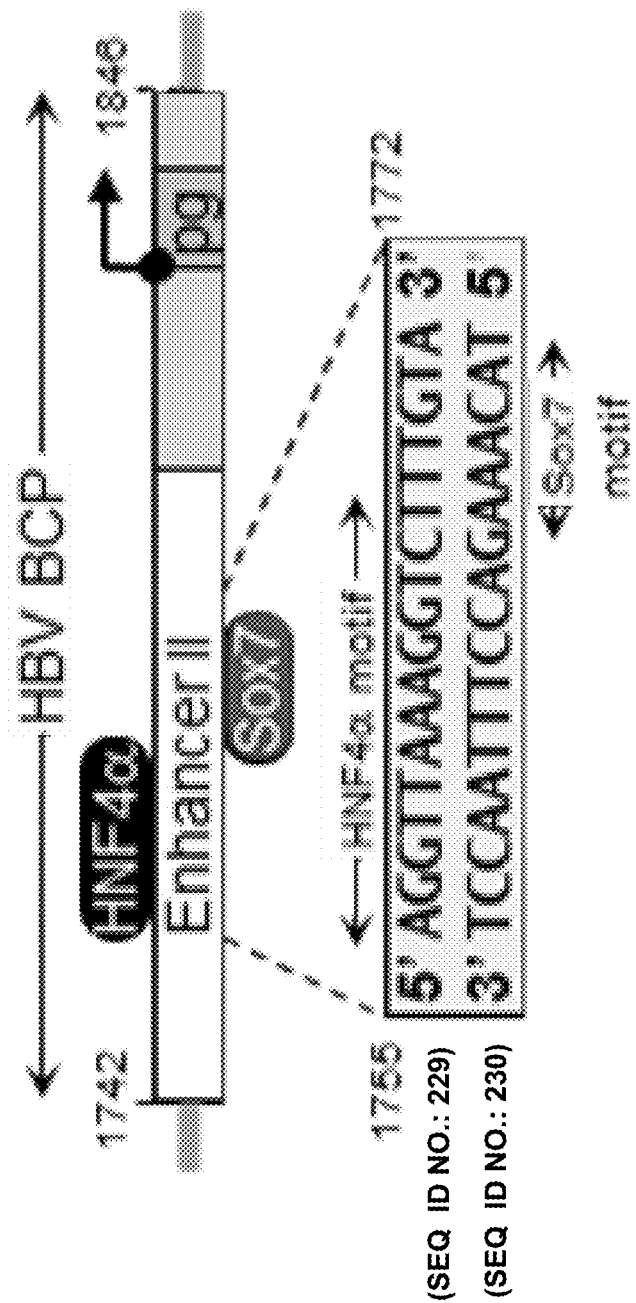
Figure 15A:
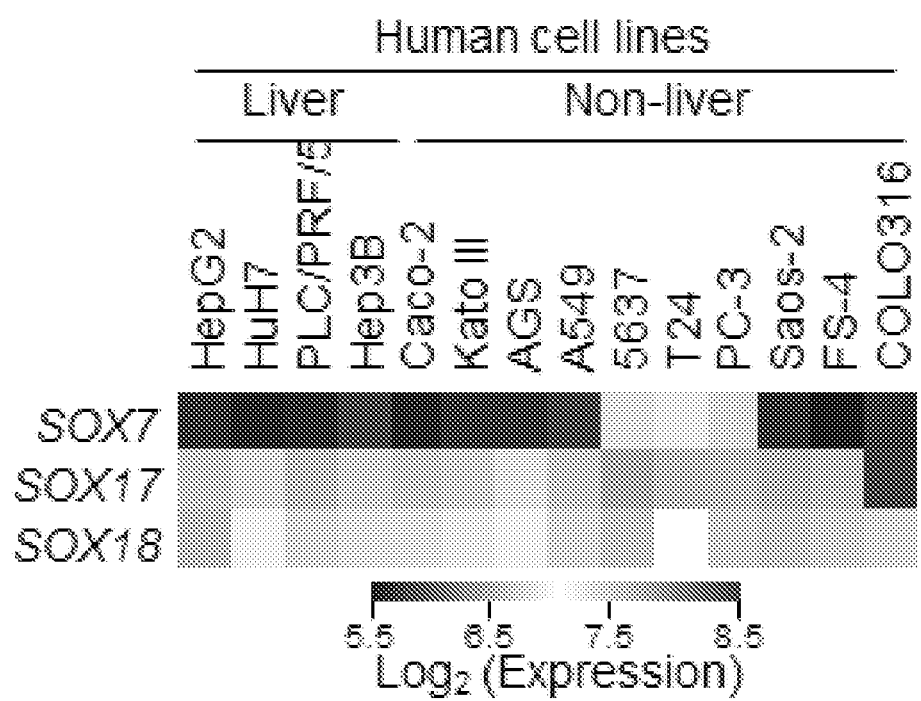
FIG. 15 shows that Sox7 is a specific inhibitor at HBVCP. a) SOX7 gene expression by HTA compared with other Sox group F family genes; b) Expression of Sox7 in primary human tissues by RT-PCR; c) Dose-dependent effect of Sox7 overexpression on transcription inhibition at HBVCP in HBV permissive cells co-transfected with HBVCP-Luc for 48 hours.
Figure 15B:
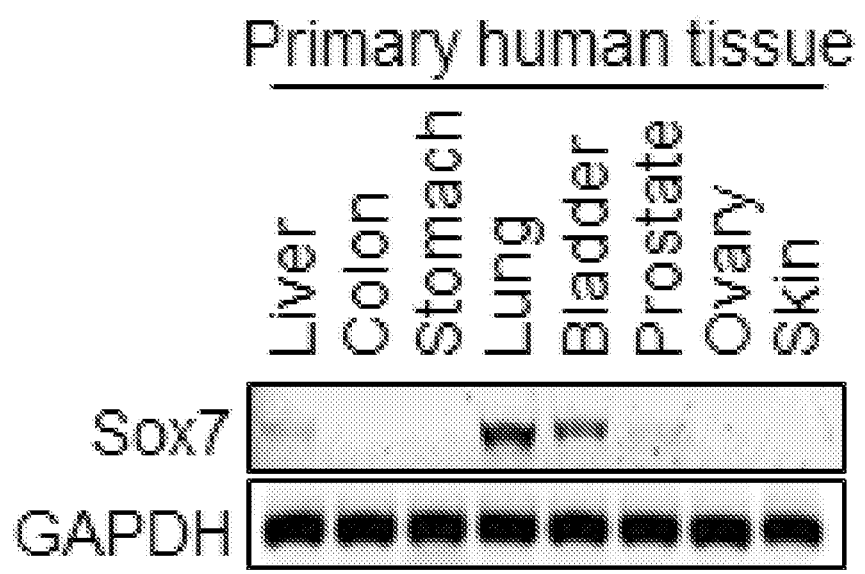

Situated at the 3' end of the HNF4α binding motif is another motif in the opposite orientation that appears to bind Sox7, a SOX (SRY-related HMG-box) family transcription factor (FIG. 7c). Sox7 is the only Subgroup F member differentially expressed between permissive and non-permissive cells (FIG. 15a). Low Sox7 expression in HBV permissive cells was confirmed in liver, colon and stomach primary human tissues (FIG. 15b).

Figure 7D:
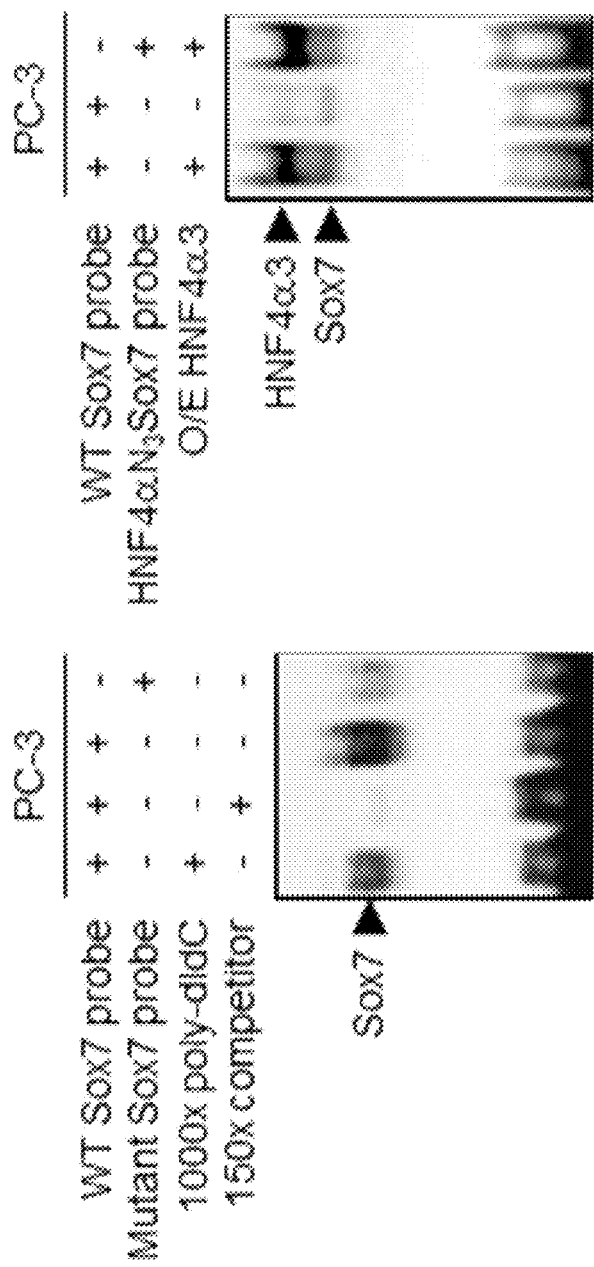

Since the Sox7 and HNF4α binding motifs overlap by one nucleotide, Sox7 may affect HNF4α binding. Using an EMSA probe bearing Sox7 motif "TTTGTA", a prominent Sox7 band was pulled down which greatly diminished when it was mutated to "TCCATA" (FIG. 7d). HNF4α was also pulled down when overexpressed in HNF4α deficient PC-3 cells. An "ACT" spacer inserted between HNF4α and Sox7 binding sites relieved steric binding interference, enabling more HNF4α to bind the "HNF4αN3Sox7" probe.

Discussion

Figure 7E:
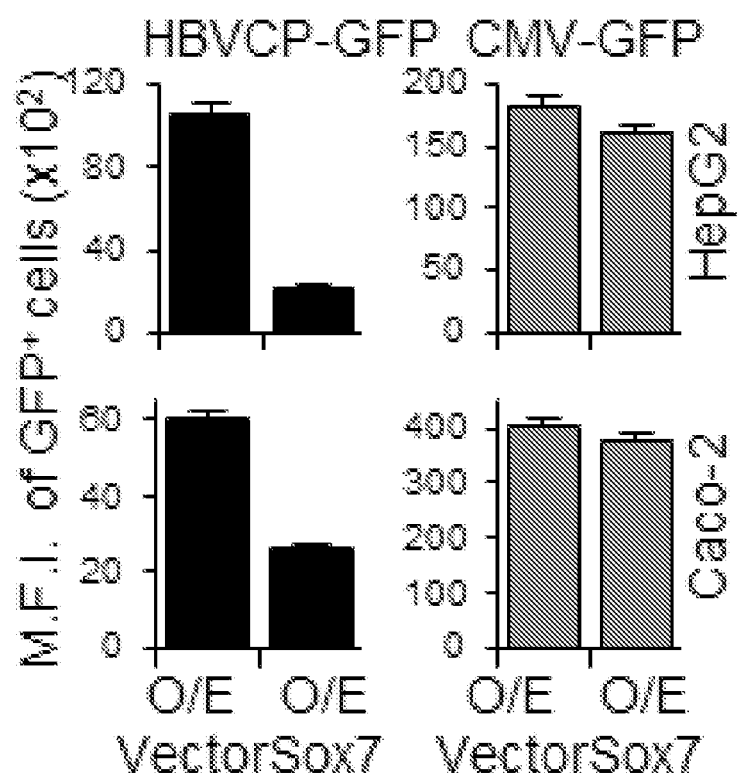
Figure 7F:
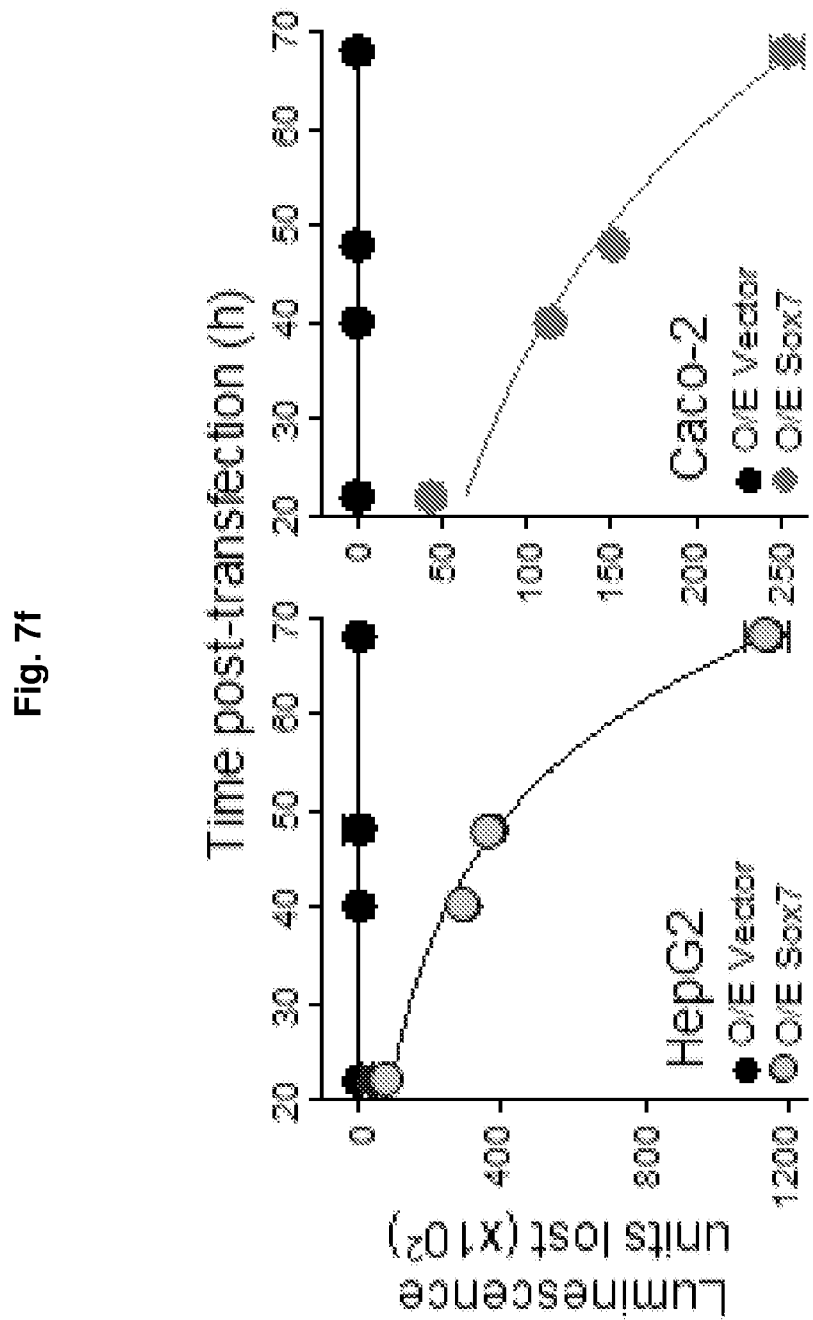
Figure 7G:
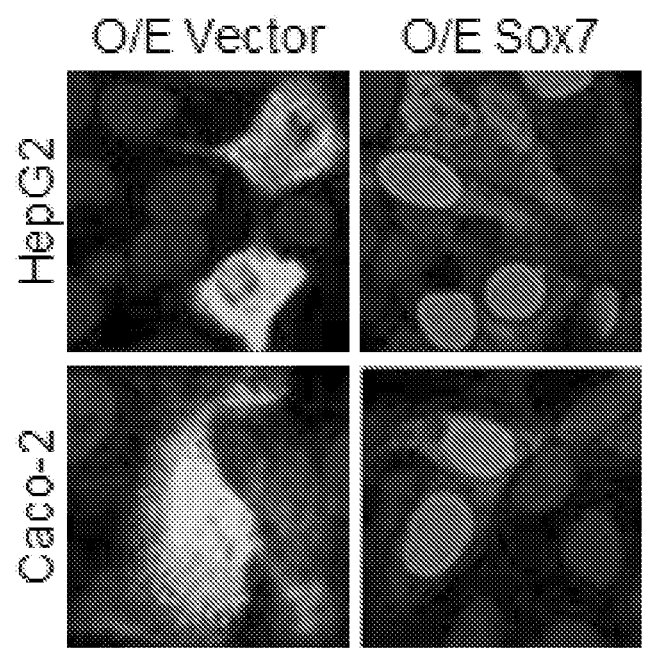
Figure 7H:
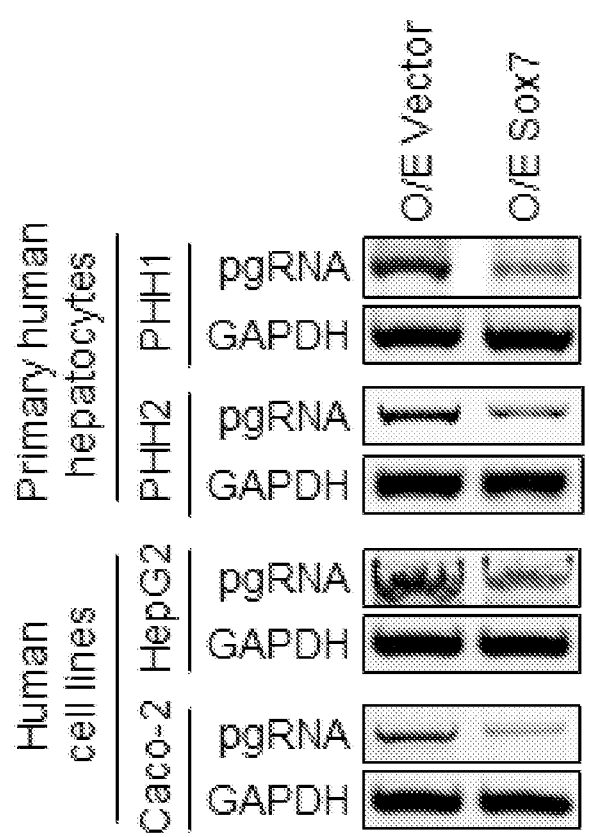
Figure 15C:
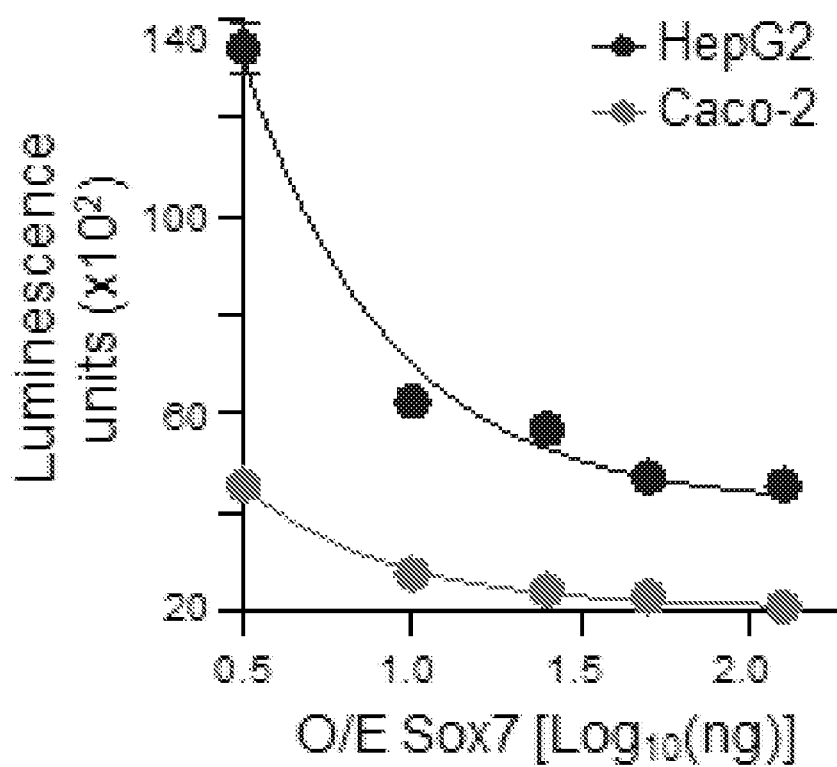
Figure 15D:
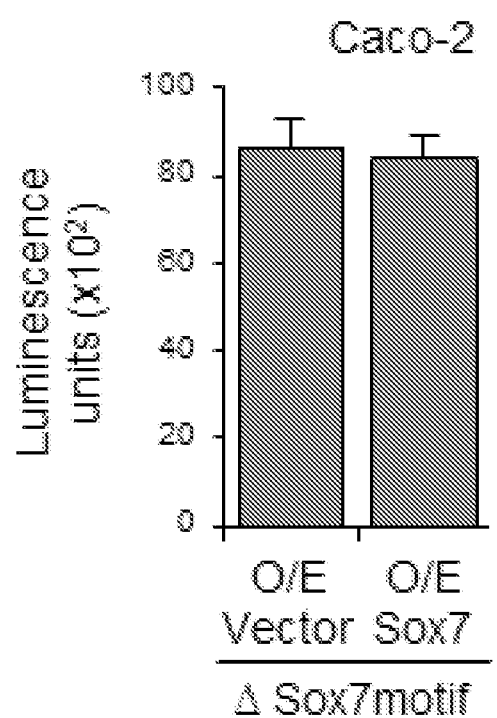

Thus, it was shown that Sox7 binding interfered with HNF4α function as Sox7 overexpression in permissive cells reduced transcription at the HBVCP in a dose-dependent manner (FIG. 7e,f and FIG. 15c) but not the CMV-GFP control (FIG. 7e). Similar results were seen with the binding motif deleted (FIG. 15d). Sox7 overexpression further suppressed whole virus replication as permissive cells transfected with HBV replicon displayed loss of HBcAg (FIG. 7g) and pgRNA (FIG. 7h). Sox7 therefore competes with HNF4α binding at the HBVCP to repress HBV transcription.

Example 4

Figure 8:
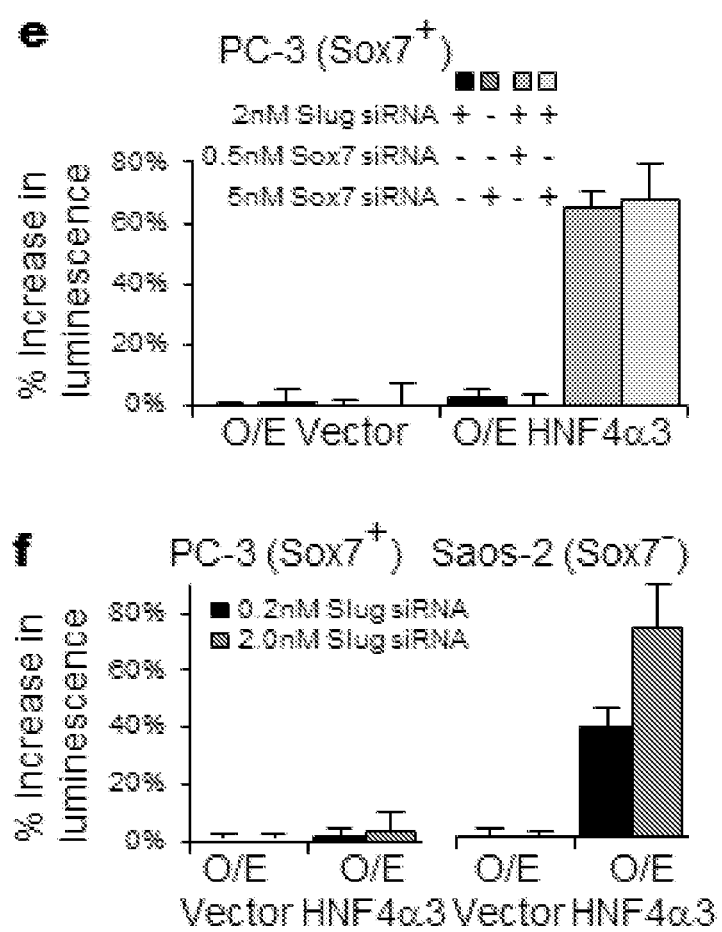
FIG. 8 shows the combined effect of Slug and Sox7. a) Enhanced transcription inhibition at the HBVCP by increasing Slug dose with coexpression of Sox7 (25 ng plasmid) on HBVCP transcription using HBVCP-Luc reporter; b) Overexpressing Slug and Sox7 together significantly suppressed HBVCP-dependent transcription; c) Combined effect of Slug and Sox7 overexpression on pgRNA synthesis in cells co-transfected for 72 hours with HBV replicon; d) Expression of full-length Sox7 transcripts by RT-PCR; e) Effect of Slug and Sox7 double knockdown with HNF4α3 overexpression on transcription at the HBVCP in PC-3 cells; f) Effect of Slug knockdown with HNF4α3 overexpression on transcription at the HBVCP in cells expressing Sox7 (Sox7+) and cells without Sox7 expression (Sox7-); g) Only cells with lacking Sox7 expression generate pgRNA when co-transfected with Slug-specific siRNA in HBV non-permissive cells co-transfected with HBV replicon; h) Slug and Sox7 determine HBV non-permissive status of cells. Sox7 motif overlaps HNF4αmotif in enhancer II while Slug motif completely overlaps the pgRNA initiator. HNF4αexpression is low in non-permissive cells and if present, antagonized by Sox7 binding to the HBVCP. Slug blocks the pgRNA initiator hence together with Sox7 prohibit transcription. In HBV permissive cells negligible expression of Sox7 and Slug allows HNF4α to activate transcription at the HBVCP.
Figure 8A:
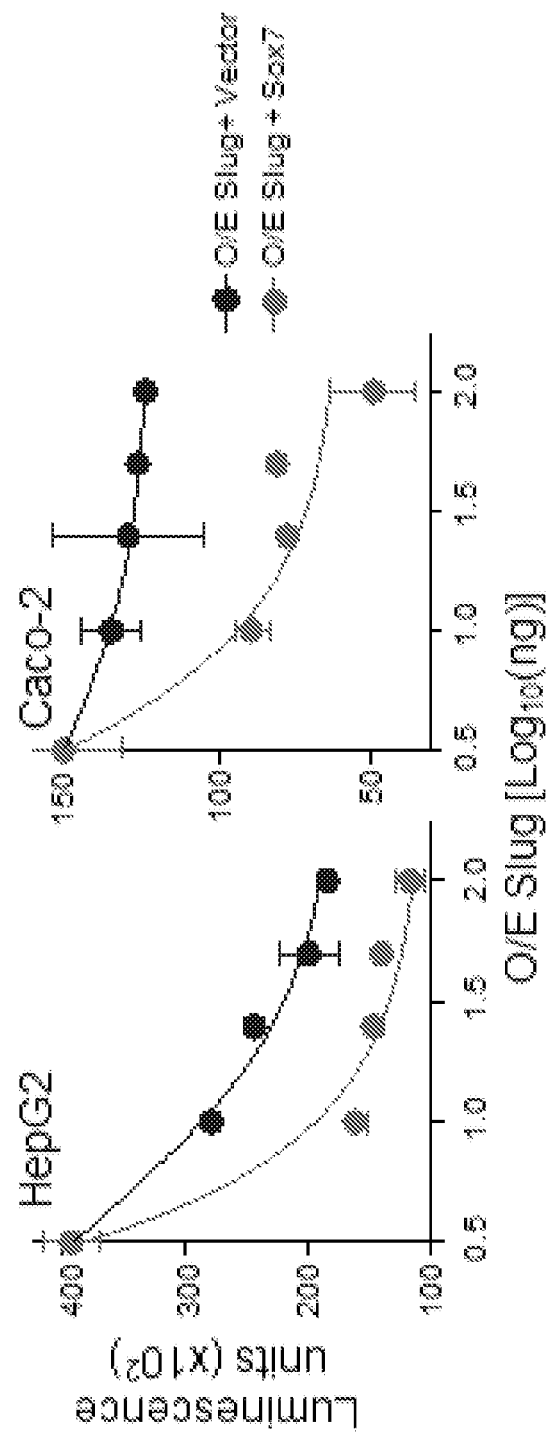
Figure 8B:
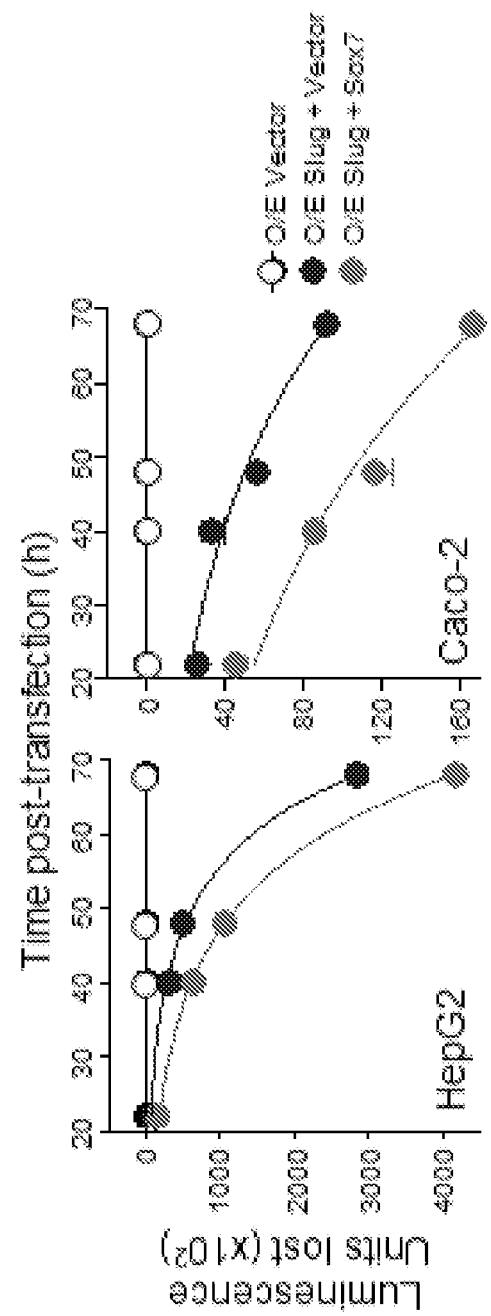

While Slug and Sox7 are independent repressors, co-expression of both factors result in more potent and enhanced repression of HBV replication together (FIG. 8a,b).

Figure 8C:
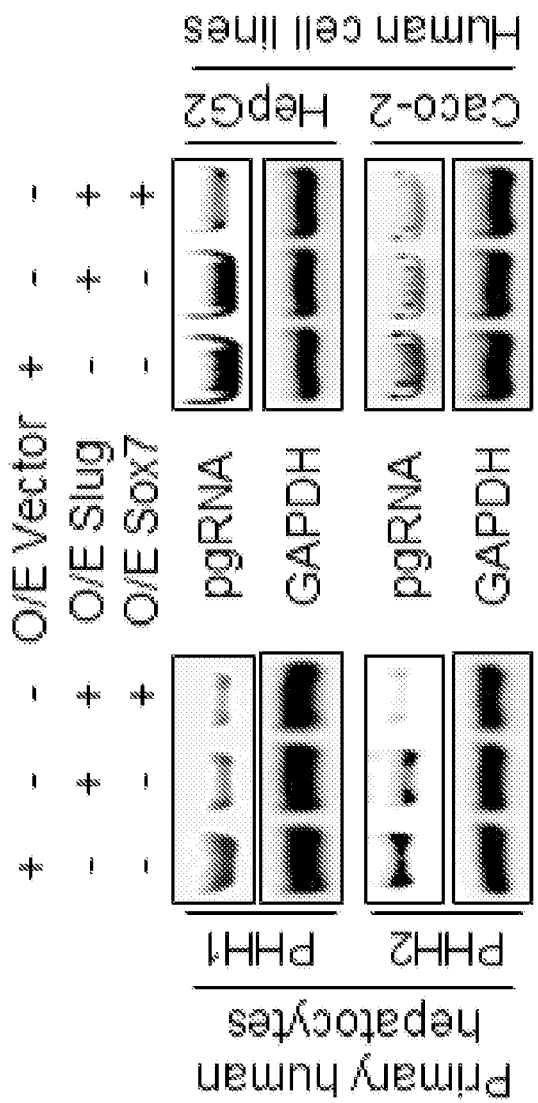
Figure 8D:
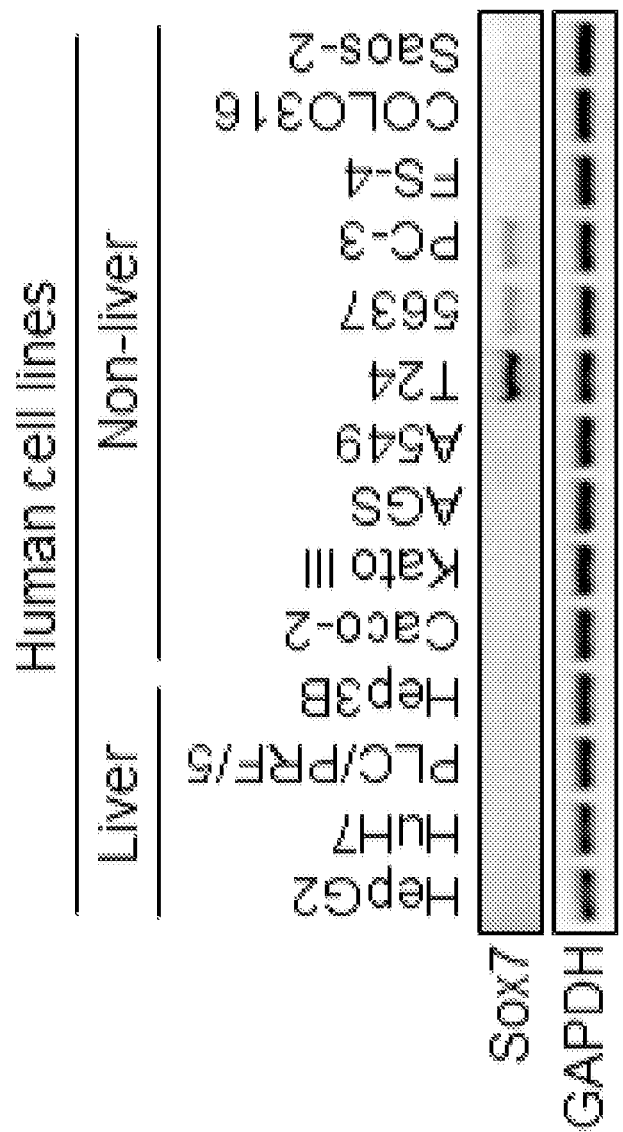
Figure 16A:
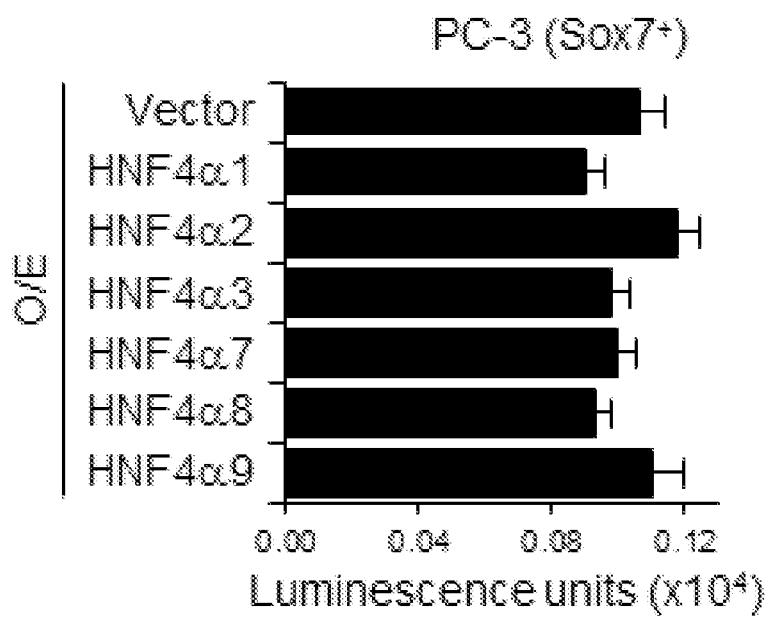

In primary human hepatocytes, co-expression of Slug and Sox7 significantly diminished whole virus replication as pgRNA was barely detected (FIG. 8c). Given that Sox7 is only appreciably expressed in T24, 5637 and PC-3 non-permissive cells (FIG. 8d), these double positive cells (Slug+Sox7+) likely have greater resilience for HBV replication. In line with this, the inactive HBVCP in PC-3 could not be activated by HNF4α overexpression alone (FIG. 16a). Slug or Sox7 expression downregulated singly was sufficient to block HBVCP transcription in the presence of HNF4α3 (FIG. 8e) and only when both Slug and Sox7 were concurrently downregulated was transcription activated in the presence of HNF4α3.

Figure 16B:
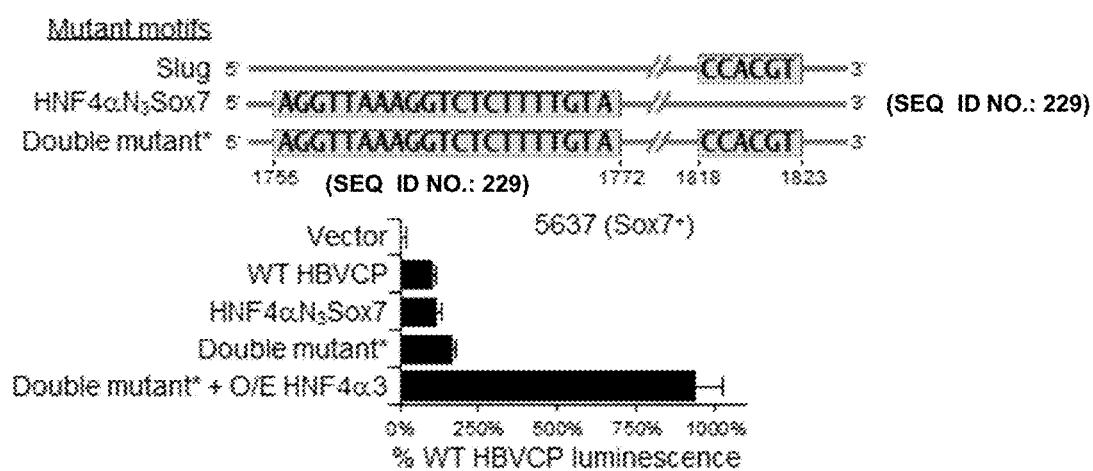

Similarly in 5637 cells, simultaneous mutation of Slug and Sox7 binding motifs lifted the barrier to transcription, activating the HBVCP in the presence of HNF4α3 (FIG. 16b).

Validation Assay (siRNA)

Figure 8G:
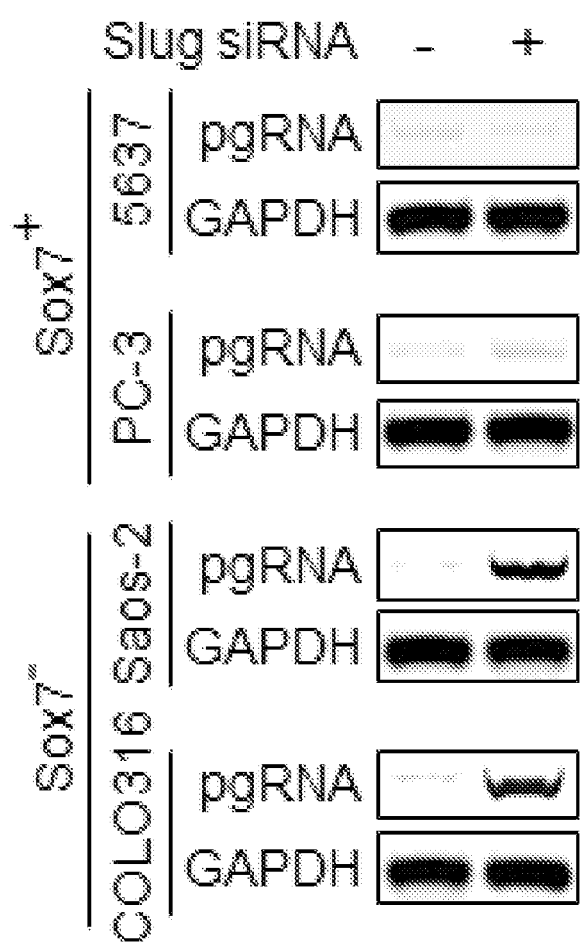

As further confirmation of their cooperative effects, HNF4α3 was overexpressed in PC-3 (Sox7+) and Saos-2 (Sox7−) cells treated with Slug siRNA. Only the Saos-2 cell line responded positively (FIG. 8f), indicating that HBV replicates readily in Sox7− non-permissive cells simply by downregulating a single factor—Slug. Indeed, Sox7− non-permissive cells treated with Slug siRNA synthesized pgRNA from HBV replicon whereas Sox7+ cells remained non-permissive (FIG. 8g).

Figure 8H:
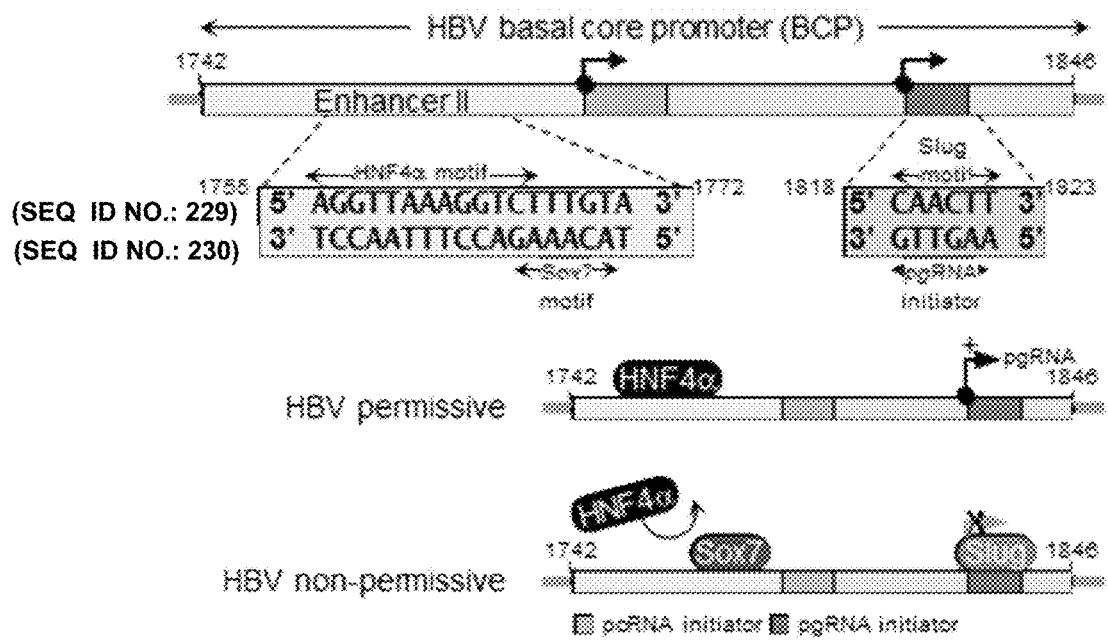

Taken together, these results show that HNF4α alone cannot overcome the Slug repression signal in the presence of Sox7, and that Slug and Sox7 determine HBV non-permissiveness to silence HBV replication (FIG. 8h).

Validation of SNAI2(Slug) and Sox7 on HBV Transcription

To validate the functionality of host Slug and Sox7 short stapled peptides were generated from their respective DNA-binding domains to test for their ability to silence HBV transcription.

Figure 17A:
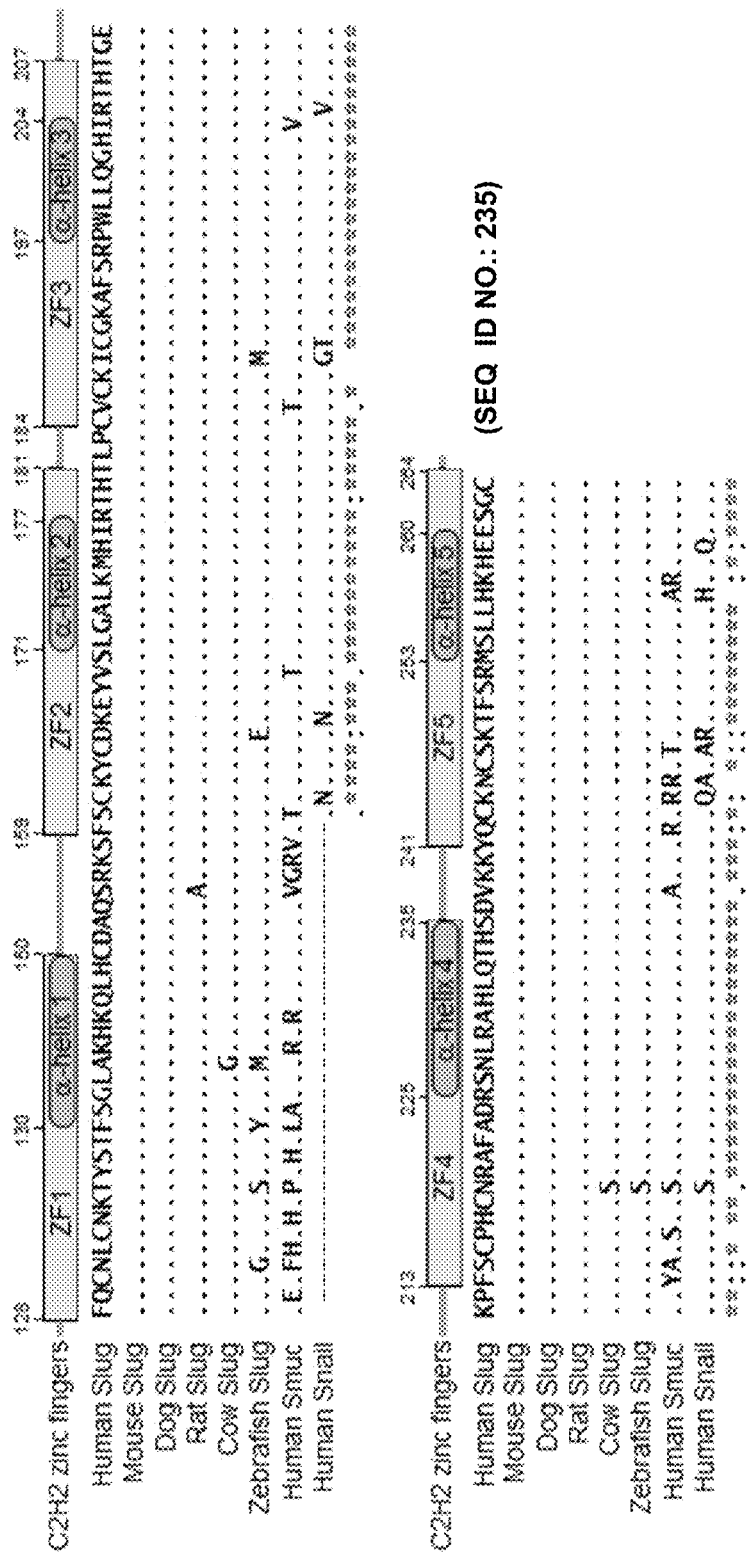

Slug binds DNA through conserved residues −1, +2, +3 and +6 relative to the α-helices within its five $C_2H_2$ zinc fingers (ZFs) that span amino acid residues 128-264 of slug (FIG. 17a). Specifically, the amino acid residues making up each of the zinc fingers are annotated as follows: ZF1=128-150; ZF2=159-181; ZF3=184-207; ZF4=213-235; ZF5=241-264.

A stapled peptide was designed for each α-helix (FIG. 9a) and relative function determined by comparing $IC_{50}$ in using HBVCP-Luc reporter (FIG. 9b). In particular, the amino acid sequences of the stapled peptides used are as follows:

```
                                          (SEQ ID NO: 215)
    Slug-ZF1s = 127-YSTFSGLAKHKQLH-150;

(SEQ ID NO: 216)
    Slug-ZF2s = 166-KEYVSLGALKMHIRTH-181;

(SEQ ID NO: 217)
    Slug-ZF3s = 192-KAFSRPWLLQGHIRTH-207;

(SEQ ID NO: 218)
    Slug-ZF4s = 222-FADRSNLRAHLQTH-235;
    and (SEQ ID NO: 219)
    Slug-ZF5s = 250-FSRMSLLHKHEES-262.
```

The underlining in these Slug sequences indicates the amino acid residues the staples are attached and cross-link. Specifically, the staple in Slug-ZF1s cross-links residues 130 and 134; the staple in Slug-ZF2s cross-links residues 171 and 178; the staple in Slug-ZF3s cross-links residues 197 and 201; the staple in Slug-ZF4s cross-links residues 229 and 233; and the staple in Slug-ZF5s cross-links residues 253 and 257.

Figure 17B:
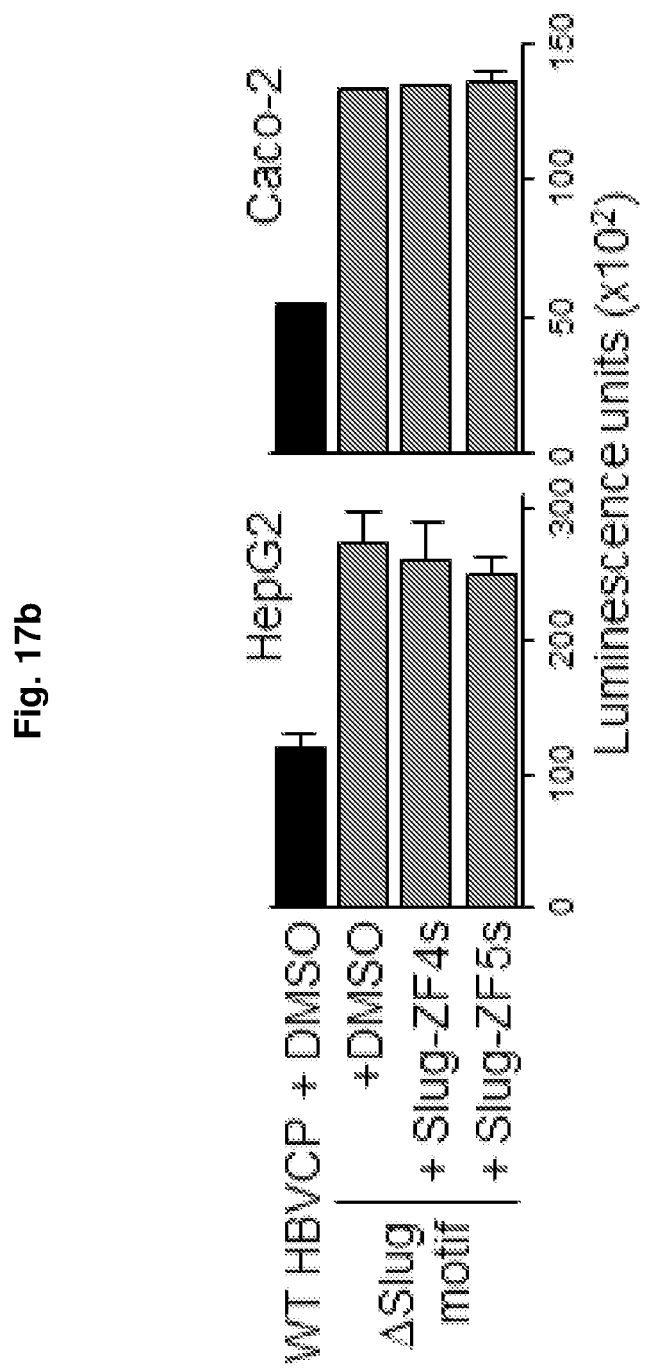
Figure 17C:
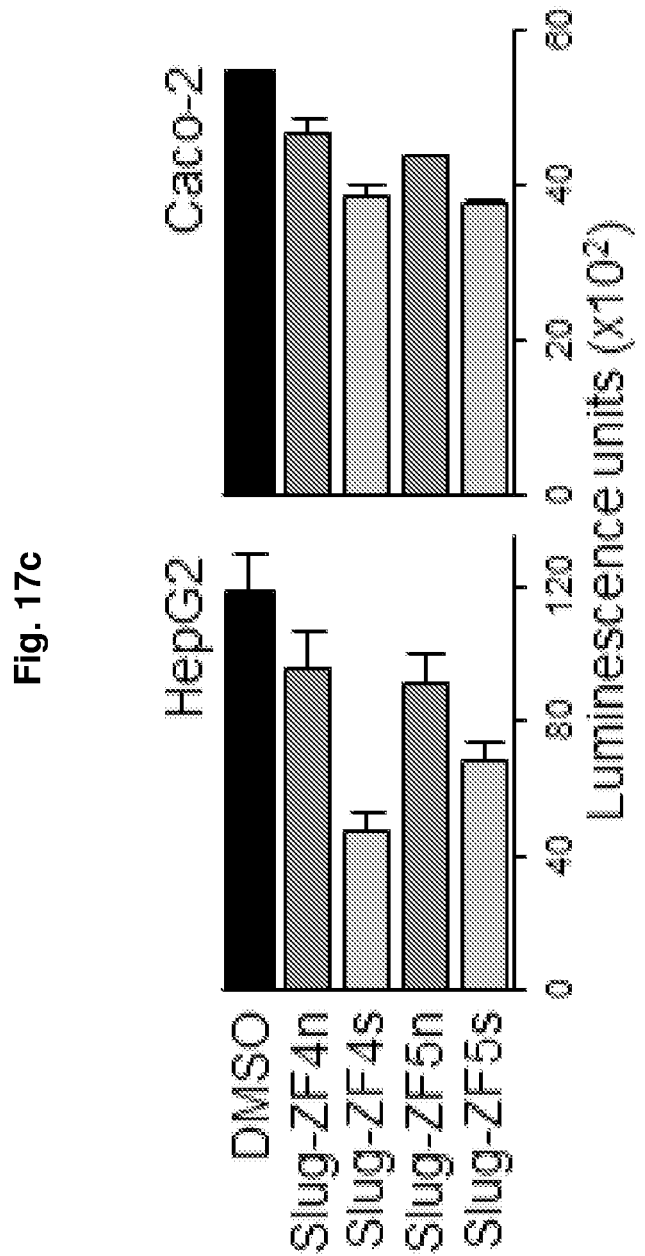

All peptides recapitulated Slug function by inhibiting transcription at the HBVCP (FIG. 9b) except Slug-ZF1s. Remarkably Slug-ZF4s and Slug-ZF5s were potent peptides that individually suppressed HBVCP transcription in HepG2 to a similar extent as native Slug protein (FIG. 9c). They acted specifically at the HBVCP as Slug motif deletion abrogated their inhibitory effect (FIG. 17b). The hydrocarbon staples were needed for functionality as non-stapled versions exhibited weaker transcription inhibition (FIG. 17c).

Sox7 binds DNA through its HMG-Box spanning amino acid residues 45-116 and contains 3 α-helices (H1-H3), wherein H1=residues 51-64, H2=residues 71-85 and H3=residues 88-107.

Figure 9E:
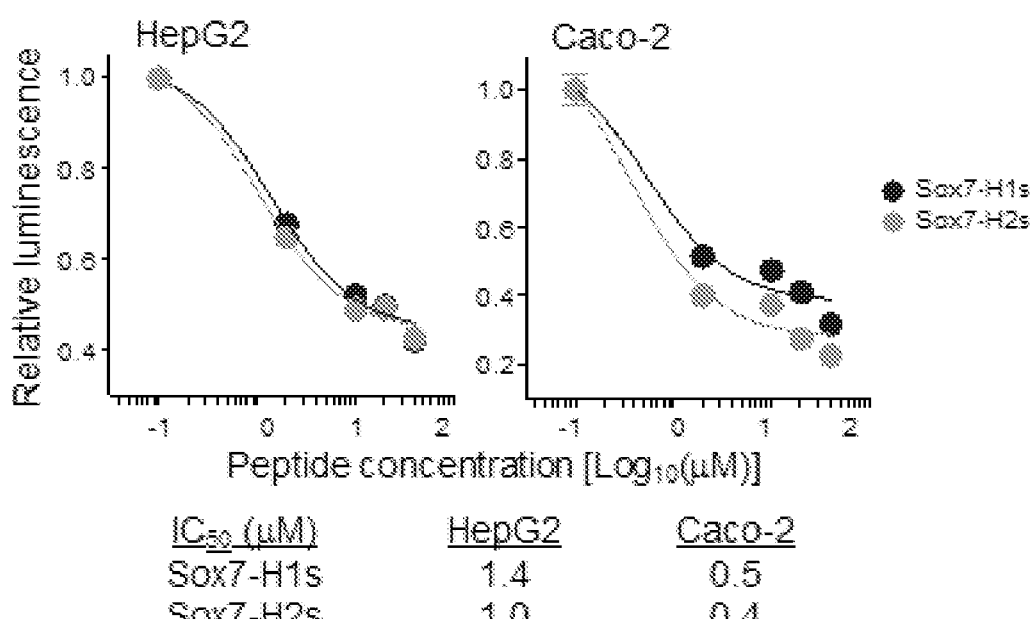

Based on Sox17-DNA crystallographic data and sequence conservation between orthologues and human Sox17 and Sox18, only α-helices H1 and H2 have high affinity for DNA (FIG. 18a) and thus H1 and H2 may be more relevant for DNA-binding than H3. The stapled peptides Sox7-H1s and Sox7-H2s (FIG. 9d) independently mimic Sox7 function by reducing transcription the HBVCP in a dose-dependent manner (FIG. 9e). In particular, the amino acid sequences of the stapled peptide used are as follows:

```
                                          (SEQ ID NO: 220)
    Sox7-H1s = 51-AFMVWAKDERKRLA-64;
    and
                                          (SEQ ID NO: 221)
    Sox7-H2s = 71-HNAELSKMLGKSWKA-85.
```

The underlining in these Sox7 sequences indicates the amino acid residues the staples are attached and cross-link. Specifically, the staple in Sox7-H1s cross-links residues 54 and 58; and the staple in Sox7-H2s cross-links residues 75 and 82.

Figure 9F:
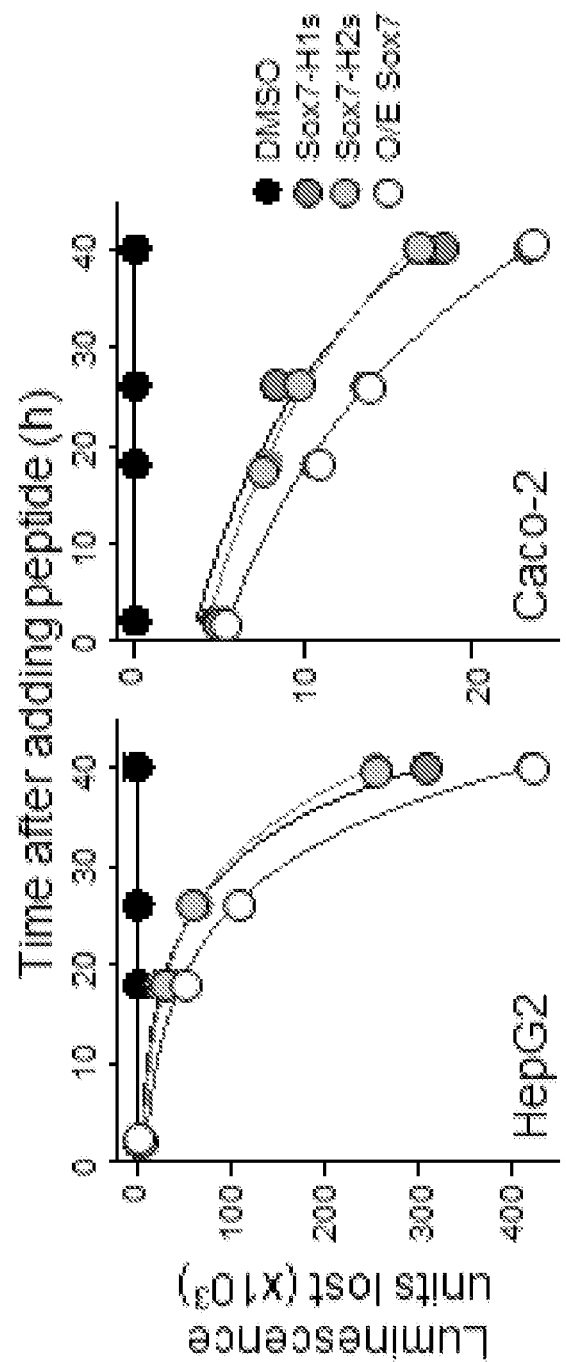

The stapled peptides inhibited transcription to a similar extent (FIG. 9f) but did not function as well as Sox7 protein, perhaps indicating that both are necessary to recapitulate Sox7 function.

Peptide stapling was necessary to preserve peptide function as non-stapled versions could not suppress HBVCP transcription as well (FIG. 19b).

Discussion

Figure 9G:
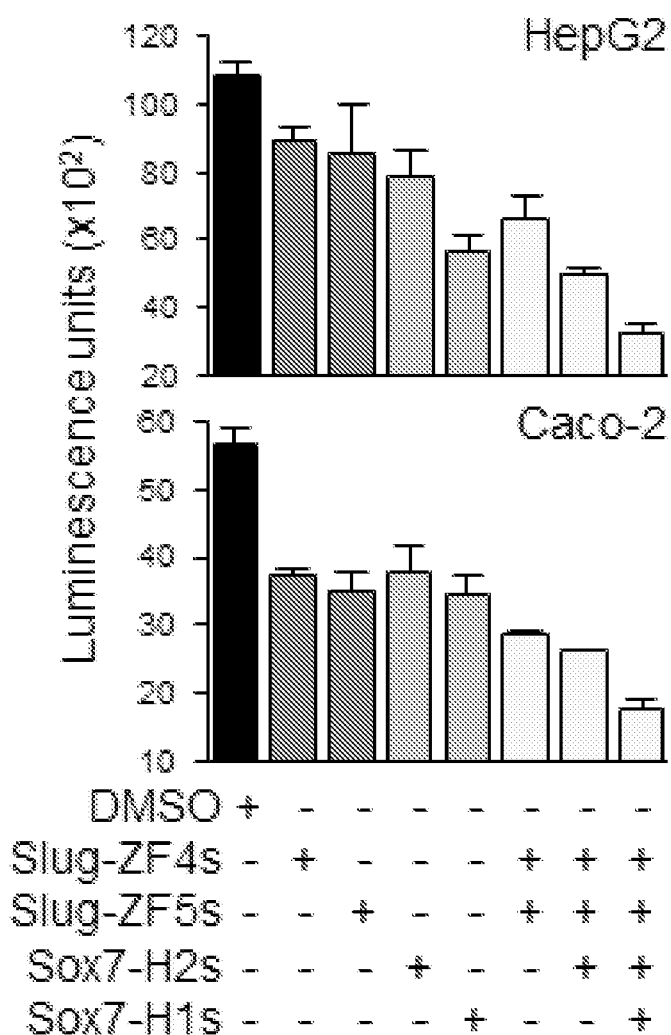
Figure 9H:
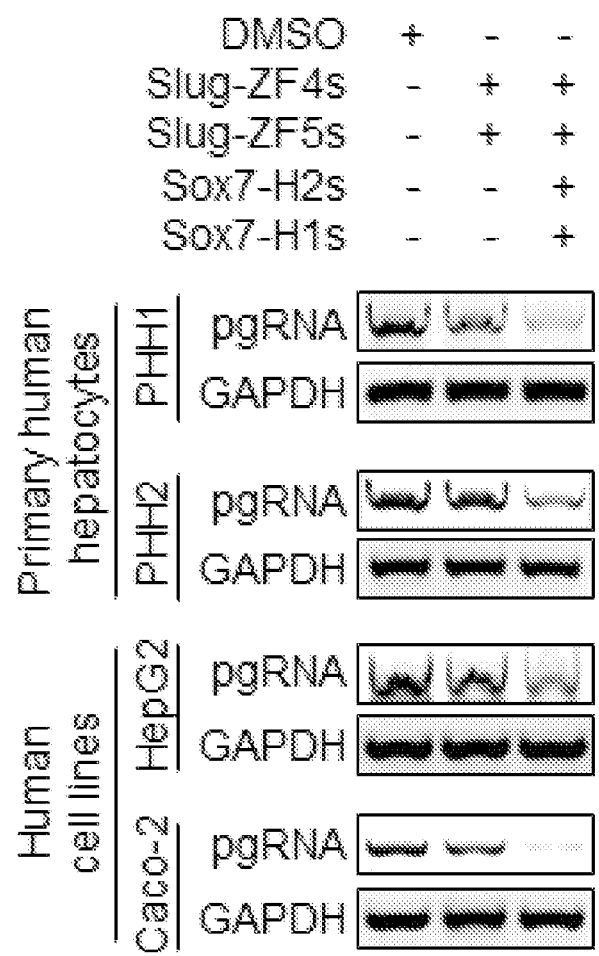

As Slug and Sox7 together prohibit HBV replication, the mimetics Slug-ZF4s, Slug-ZF5s, Sox7-H1s and Sox7-H2s may achieve the greatest inhibition when used together. Sequential addition of mimetics confirmed this, as Slug mimetics outperformed either Slug-ZF4s or Slug-ZF5s alone, adding Sox7-H2s reduced HBVCP activity further with maximal loss when Sox7-H1s was also added (FIG. 9g). When assessed for the ability to suppress HBV replication, it was observed that pgRNA was reduced with Slug mimetics alone, and was remarkably further diminished to negligible levels when Sox7 mimetics were added into primary humanhepatocytes and HBV permissive cells transfected with HBV replicon (FIG. 9h). This was not a consequence of cytotoxicity as the proliferative capacity of cells did not differ from DMSO treated controls (Extended Data FIG. 18c).

Accordingly, the stapled peptides and mimics described herein are capable of inhibiting HBV replication in cell lines (FIGS. 9c, e, f) and primary human hepatocytes (FIG. 9g) In particular, the extent of HBV inhibition for some peptides is comparable to the overexpression of the whole protein in HepG2 liver cells.

Figure 18C:
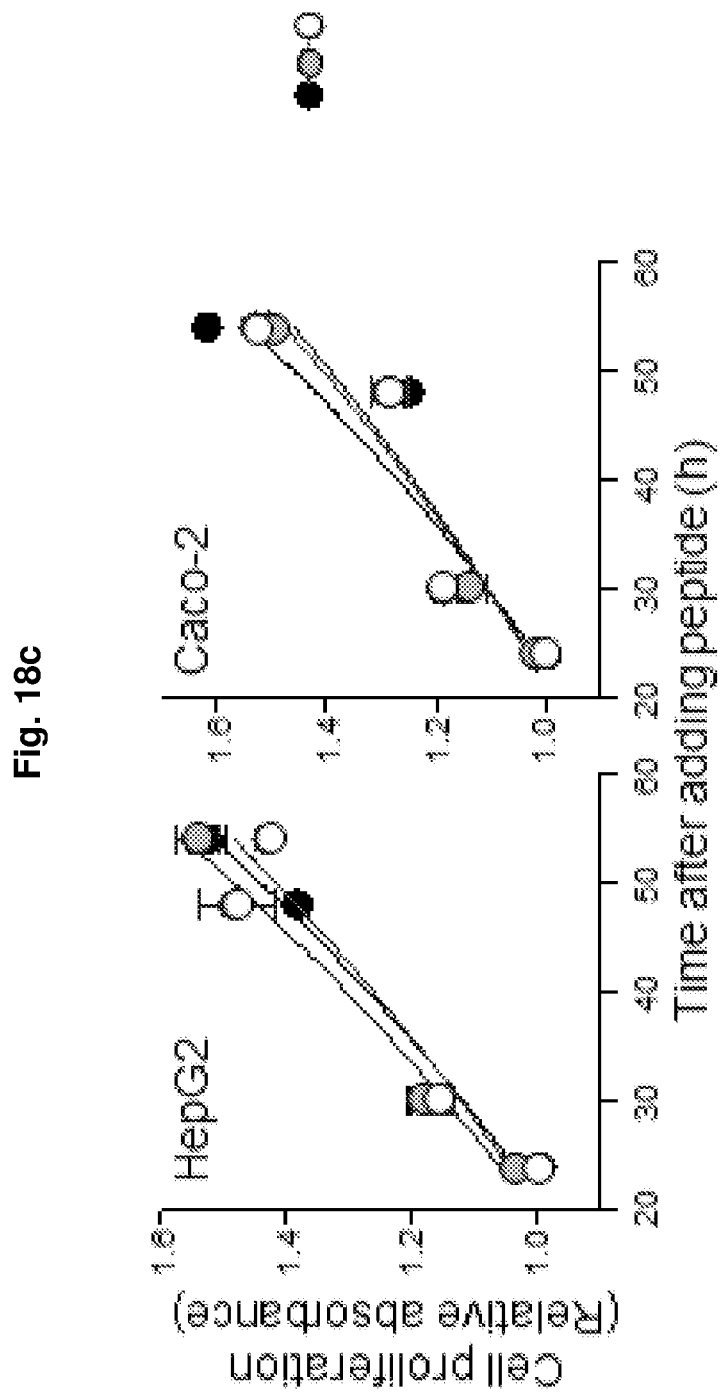

In this regard, the stapled peptides or mimics only require minor modification in terms of length and staple positions to be functionally optimized. Moreover, the stapled peptides or mimics are not cytotoxic to HepG2 cells when used at concentrations sufficient to inhibit HBV replication (FIG. 18c). It is noteworthy that HepG2 cells are often the cells of choice for cytotoxicity assays, as they possess most of the functional enzymes required for detoxification and are second to primary human hepatocytes.

While nucleoside/nucleotide analogues and interferons are available for the treatment of HBV infection, they require long-term use because they cannot suppress HBV replication to sufficiently low levels for immune clearance. Thus, stapled peptides or mimics developed on the findings and data disclosed herein may bring HBV replication to a minimum for current therapeutics to be more effective, hence resulting the advantage of reducing drug dependency of patients for viral clearance. In this regard, the representative stapled peptides or mimics described herein were shown to be significantly advantageous as they were almost as potent as the native whole proteins (for example, Slug and Sox7). In that regard, the specific peptide sequences of a length of about 13-14 amino acids appear to be sufficiently specific as they possess the required potency to inhibit HBVCP.

FIG. 9h shows that 2 fragments from Slug and 2 fragments from Sox7 conferred very high potency in inhibiting HBV transcription. These experiments were performed with primary human hepatocytes (as well as cell lines), which further supports and validate their relevance in modulating HBV replication and use in the methods and therapeutic treatments disclosed herein.

In summary, the present invention has elucidated that Slug and Sox7 are independent transcription repressors that decide the ability of a cell to support HBV replication. While HNF4α is an activator that enhances viral replication efficiency, it can only do so when Slug and Sox7 are absent. Since the potent HBVCP activator HNF4α1 is preferentially enriched in liver cells, the data disclosed herein provides fundamental insights on HBV replication primarily in the liver.

Using stapled peptides and mimics derived from DNA-binding domains of Slug and Sox7, HBV replication has been shown to be successfully silenced by inhibiting HBVCP activity and pgRNA transcription, demonstrating that novel HBV therapeutics can be developed by targeting the identified host factors described herein. Moreover, as viruses are dependent on host factors for replication, this approach of host repressor molecular mimicry may also be useful for inhibiting replication of other viruses.

What is claimed is:

1. A method of screening at least one agent for modulating HBV replication, comprising:
    a) contacting a cell expressing the HBV virus with the at least one agent,
        wherein the at least one agent modulates the expression of SNAI2, SOX7, or both;
    b) obtaining a HBV expression profile of the cell contacted with the at least one agent; and
    c) comparing the HBV expression profile of the cell in b) with an HBV expression profile of a control cell that has not been contacted with said at least one agent,
    wherein a decrease or increase in the expression of the HBV virus in the cell, relative to the control cell, indicates a modulation of HBV replication by said at least one agent.

2. The method of claim 1, wherein the at least one agent is selected from the group consisting of a chemical compound, a small molecule, a oligonucleotide, a protein, a peptide, a stapled peptide, a peptidomimetic, an antibody and an antigen binding molecule; optionally wherein the oligonucleotide is a siRNA or shRNA.

3. The method of claim 1, wherein the contacting step comprises transfecting the cell with the siRNA or shRNA: optionally wherein the cell is permissive of HBV replication; optionally wherein the cell is selected from the group consisting of a liver cell, colon cell, stomach cell, blood cell, kidney cell and lung cell; optionally wherein the cell is comprised in a biological sample; optionally wherein the biological sample has been obtained from an HBV infected subject; optionally wherein the cell is derived from a cell line selected from the group consisting of HepG2, HuH6, HuH7, HuH4, PLC/PRF/5, Kato III, AGS, HCT116,Caco-2, HL-60, HEK293 and A549.

4. The method of claim 1, wherein the contacting step comprises culturing the cell in a suitable culture medium that promotes HBV replication; optionally wherein the contacting step comprises transfecting the cell with a HBV replicon.

5. The method of claim 1, wherein obtaining the HBV expression profile comprises measuring one or more markers of HBV replication; optionally wherein the one or more markers of HBV replication are selected from the group consisting of pre-genomic RNA levels of the HBV replicon, hepatitis B surface antigen levels, and hepatitis B core antigen levels; optionally wherein obtaining the HBV expression profile comprises western blot analysis of the at least one factor in the cell and measuring a band intensity of the at least one factor; optionally wherein the band intensity of the at least one factor is normalized to a control, and wherein a relative difference of 1 to 35% or greater between the band intensity of the at least one factor and the control indicates a modulation of HBV replication by said at least one agent.

* * * * *

SEQUENCE LISTING

```
<160> NUMBER OF SEQ ID NOS: 236

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
tgagcggccg cgatatgcga tctc                                         24

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
tgagcggccg cgatatggtc agcg                                         24

<210> SEQ ID NO 3
<211> LENGTH: 27
<212> TYPE: DNA
<213> ORGANISM: Artificial Sequence
<220> FEATURE:
<223> OTHER INFORMATION: Primer

<400> SEQUENCE: 3
attcccggga taacttcctg cttggtg                                      27

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
attcccggga gcaacttgcc caaagcg                                      27

<210> SEQ ID NO 5
<211> LENGTH: 27
<212> TYPE: DNA
<213> ORGANISM: Artificial Sequence
<220> FEATURE:
<223> OTHER INFORMATION: Primer
```

<400> SEQUENCE: 5
aacggacaga tgtccacccc tgagacc                                       27

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
ggtctcaggg gtggacatct gtccgtt                                       27

<210> SEQ ID NO 7
<211> LENGTH: 26
<212> TYPE: DNA
<213> ORGANISM: Artificial Sequence
<220> FEATURE:
<223> OTHER INFORMATION: Primer

<400> SEQUENCE: 7
agcaacggac agatgtgtga gtggcc                                        26

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
ggccactcac acatctgtcc gttgct                                        26

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
acaccgcctc agctctgtat cgag                                          24

<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10
ttctttataa gggtcaatgt ccatgcccc                                     29

<210> SEQ ID NO 11
<211> LENGTH: 19
<212> TYPE: RNA
<213> ORGANISM: Artificial Sequence
<220> FEATURE:
<223> OTHER INFORMATION: ARID3A siRNA 1

<400> SEQUENCE: 11
gagaucaacg gcaucaugu                                                19

<210> SEQ ID NO 12
<211> LENGTH: 19

```
<212> TYPE: RNA
<213> ORGANISM: Artificial Sequence
<220> FEATURE:
<223> OTHER INFORMATION: ARID3A siRNA 2

<400> SEQUENCE: 12
cuuacgagga gcaguuuaa                                                      19

<210> SEQ ID NO 13
<211> LENGTH: 19
<212> TYPE: RNA
<213> ORGANISM: Artificial Sequence
<220> FEATURE:
<223> OTHER INFORMATION: ARID3A siRNA 3

<400> SEQUENCE: 13
ucaaauaacu cguugccuu                                                      19

<210> SEQ ID NO 14
<211> LENGTH: 19
<212> TYPE: RNA
<213> ORGANISM: Artificial Sequence
<220> FEATURE:
<223> OTHER INFORMATION: ARID3A siRNA 4

<400> SEQUENCE: 14
gaaacuacag gccgugaug                                                      19

<210> SEQ ID NO 15
<211> LENGTH: 19
<212> TYPE: RNA
<213> ORGANISM: Artificial Sequence
<220> FEATURE:
<223> OTHER INFORMATION: ATF2 siRNA 1

<400> SEQUENCE: 15
gagaagagca gcuaacgaa                                                      19

<210> SEQ ID NO 16
<211> LENGTH: 19
<212> TYPE: RNA
<213> ORGANISM: Artificial Sequence
<220> FEATURE:
<223> OTHER INFORMATION: ATF2 siRNA 2

<400> SEQUENCE: 16
caugguagcg gauugguua                                                      19

<210> SEQ ID NO 17
<211> LENGTH: 19
<212> TYPE: RNA
<213> ORGANISM: Artificial Sequence
<220> FEATURE:
<223> OTHER INFORMATION: ATF2 siRNA 3

<400> SEQUENCE: 17
ggaaguacca uuggcacaa                                                      19

<210> SEQ ID NO 18
<211> LENGTH: 19
<212> TYPE: RNA
<213> ORGANISM: Artificial Sequence
<220> FEATURE:
<223> OTHER INFORMATION: ATF2 siRNA 4

<400> SEQUENCE: 18
```

```
ugaggagccu ucuguugua                                                    19

<210> SEQ ID NO 19
<211> LENGTH: 19
<212> TYPE: RNA
<213> ORGANISM: Artificial Sequence
<220> FEATURE:
<223> OTHER INFORMATION: ATF3 siRNA 1

<400> SEQUENCE: 19
gagcuaagca gucguggua                                                    19

<210> SEQ ID NO 20
<211> LENGTH: 19
<212> TYPE: RNA
<213> ORGANISM: Artificial Sequence
<220> FEATURE:
<223> OTHER INFORMATION: ATF3 siRNA 2

<400> SEQUENCE: 20
gcaaagugcc gaaacaaga                                                    19

<210> SEQ ID NO 21
<211> LENGTH: 19
<212> TYPE: RNA
<213> ORGANISM: Artificial Sequence
<220> FEATURE:
<223> OTHER INFORMATION: ATF3 siRNA 3

<400> SEQUENCE: 21
agaagcagca uuugauaua                                                    19

<210> SEQ ID NO 22
<211> LENGTH: 19
<212> TYPE: RNA
<213> ORGANISM: Artificial Sequence
<220> FEATURE:
<223> OTHER INFORMATION: ATF3 siRNA 4

<400> SEQUENCE: 22
cgagaaagaa auaagauug                                                    19

<210> SEQ ID NO 23
<211> LENGTH: 19
<212> TYPE: RNA
<213> ORGANISM: Artificial Sequence
<220> FEATURE:
<223> OTHER INFORMATION: ATF4 siRNA 1

<400> SEQUENCE: 23
cagauuggau guuggagaa                                                    19

<210> SEQ ID NO 24
<211> LENGTH: 19
<212> TYPE: RNA
<213> ORGANISM: Artificial Sequence
<220> FEATURE:
<223> OTHER INFORMATION: ATF4 siRNA 2

<400> SEQUENCE: 24
cgacuuggau gcccuguug                                                    19

<210> SEQ ID NO 25
<211> LENGTH: 19
<212> TYPE: RNA
<213> ORGANISM: Artificial Sequence
```

```
<220> FEATURE:
<223> OTHER INFORMATION: ATF4 siRNA 3

<400> SEQUENCE: 25
gaagaacgag gcucuaaaa                                                    19

<210> SEQ ID NO 26
<211> LENGTH: 19
<212> TYPE: RNA
<213> ORGANISM: Artificial Sequence
<220> FEATURE:
<223> OTHER INFORMATION: ATF4 siRNA 4

<400> SEQUENCE: 26
gagauaggaa gccagacua                                                    19

<210> SEQ ID NO 27
<211> LENGTH: 19
<212> TYPE: RNA
<213> ORGANISM: Artificial Sequence
<220> FEATURE:
<223> OTHER INFORMATION: CALCOCO1 siRNA 1

<400> SEQUENCE: 27
gugcagagau acuucgauu                                                    19

<210> SEQ ID NO 28
<211> LENGTH: 19
<212> TYPE: RNA
<213> ORGANISM: Artificial Sequence
<220> FEATURE:
<223> OTHER INFORMATION: CALCOCO1 siRNA 2

<400> SEQUENCE: 28
ggacauccug agccggcaa                                                    19

<210> SEQ ID NO 29
<211> LENGTH: 19
<212> TYPE: RNA
<213> ORGANISM: Artificial Sequence
<220> FEATURE:
<223> OTHER INFORMATION: CALCOCO1 siRNA 3

<400> SEQUENCE: 29
ugacagacuc agaggacga                                                    19

<210> SEQ ID NO 30
<211> LENGTH: 19
<212> TYPE: RNA
<213> ORGANISM: Artificial Sequence
<220> FEATURE:
<223> OTHER INFORMATION: CALCOCO1 siRNA 4

<400> SEQUENCE: 30
ugucagaaag uaagcggga                                                    19

<210> SEQ ID NO 31
<211> LENGTH: 19
<212> TYPE: RNA
<213> ORGANISM: Artificial Sequence
<220> FEATURE:
<223> OTHER INFORMATION: CHD3 siRNA 1

<400> SEQUENCE: 31 gaauacccu gaauacgaa                                                     19
```

<210> SEQ ID NO 32
<211> LENGTH: 19
<212> TYPE: RNA
<213> ORGANISM: Artificial Sequence
<220> FEATURE:
<223> OTHER INFORMATION: CHD3 siRNA 2

<400> SEQUENCE: 32
ccagaaugau gcucaauuu                                                  19

<210> SEQ ID NO 33
<211> LENGTH: 19
<212> TYPE: RNA
<213> ORGANISM: Artificial Sequence
<220> FEATURE:
<223> OTHER INFORMATION: CHD3 siRNA 3

<400> SEQUENCE: 33
cauaagaggc ggaguaaga                                                  19

<210> SEQ ID NO 34
<211> LENGTH: 19
<212> TYPE: RNA
<213> ORGANISM: Artificial Sequence
<220> FEATURE:
<223> OTHER INFORMATION: CHD3 siRNA 4

<400> SEQUENCE: 34
cguaugagcu gaucaccau                                                  19

<210> SEQ ID NO 35
<211> LENGTH: 19
<212> TYPE: RNA
<213> ORGANISM: Artificial Sequence
<220> FEATURE:
<223> OTHER INFORMATION: CNOT11 siRNA 1

<400> SEQUENCE: 35
ggaugaacuu gcuuggcua                                                  19

<210> SEQ ID NO 36
<211> LENGTH: 19
<212> TYPE: RNA
<213> ORGANISM: Artificial Sequence
<220> FEATURE:
<223> OTHER INFORMATION: CNOT11 siRNA 2

<400> SEQUENCE: 36
guguggagau caaacgaau                                                  19

<210> SEQ ID NO 37
<211> LENGTH: 19
<212> TYPE: RNA
<213> ORGANISM: Artificial Sequence
<220> FEATURE:
<223> OTHER INFORMATION: CNOT11 siRNA 3

<400> SEQUENCE: 37
ggaaguugua aaucgacua                                                  19

<210> SEQ ID NO 38
<211> LENGTH: 19
<212> TYPE: RNA
<213> ORGANISM: Artificial Sequence
<220> FEATURE:
<223> OTHER INFORMATION: CNOT11 siRNA 4

```
<400> SEQUENCE: 38
auucaguagg auacgagaa                                                    19

<210> SEQ ID NO 39
<211> LENGTH: 19
<212> TYPE: RNA
<213> ORGANISM: Artificial Sequence
<220> FEATURE:
<223> OTHER INFORMATION: DCP1A siRNA 1

<400> SEQUENCE: 39
gcaagcuugu cgauauaua                                                    19

<210> SEQ ID NO 40
<211> LENGTH: 19
<212> TYPE: RNA
<213> ORGANISM: Artificial Sequence
<220> FEATURE:
<223> OTHER INFORMATION: DCP1A siRNA 2

<400> SEQUENCE: 40
acucauggcu gauguggua                                                    19

<210> SEQ ID NO 41
<211> LENGTH: 19
<212> TYPE: RNA
<213> ORGANISM: Artificial Sequence
<220> FEATURE:
<223> OTHER INFORMATION: DCP1A siRNA 3

<400> SEQUENCE: 41
acaagcaucu gacgguaga                                                    19

<210> SEQ ID NO 42
<211> LENGTH: 19
<212> TYPE: RNA
<213> ORGANISM: Artificial Sequence
<220> FEATURE:
<223> OTHER INFORMATION: DCP1A siRNA 4

<400> SEQUENCE: 42
ccaauucauu ccuaccauu                                                    19

<210> SEQ ID NO 43
<211> LENGTH: 19
<212> TYPE: RNA
<213> ORGANISM: Artificial Sequence
<220> FEATURE:
<223> OTHER INFORMATION: DDX39B siRNA 1

<400> SEQUENCE: 43
guagaagacu cgcccauuu                                                    19

<210> SEQ ID NO 44
<211> LENGTH: 19
<212> TYPE: RNA
<213> ORGANISM: Artificial Sequence
<220> FEATURE:
<223> OTHER INFORMATION: DDX39B siRNA 2

<400> SEQUENCE: 44
gggcuuggcu aucacauuu                                                    19

<210> SEQ ID NO 45
```

```
<211> LENGTH: 19
<212> TYPE: RNA
<213> ORGANISM: Artificial Sequence
<220> FEATURE:
<223> OTHER INFORMATION: DDX39B siRNA 3

<400> SEQUENCE: 45
gaauggaugu ccugugcca                                                19

<210> SEQ ID NO 46
<211> LENGTH: 19
<212> TYPE: RNA
<213> ORGANISM: Artificial Sequence
<220> FEATURE:
<223> OTHER INFORMATION: DDX39B siRNA 4

<400> SEQUENCE: 46
gaacugcccg cauaucguc                                                19

<210> SEQ ID NO 47
<211> LENGTH: 19
<212> TYPE: RNA
<213> ORGANISM: Artificial Sequence
<220> FEATURE:
<223> OTHER INFORMATION: DYRK1B siRNA 1

<400> SEQUENCE: 47
gagaugaagu acuauauag                                                19

<210> SEQ ID NO 48
<211> LENGTH: 19
<212> TYPE: RNA
<213> ORGANISM: Artificial Sequence
<220> FEATURE:
<223> OTHER INFORMATION: DYRK1B siRNA 2

<400> SEQUENCE: 48
cgaaagaacu caggaagga                                                19

<210> SEQ ID NO 49
<211> LENGTH: 19
<212> TYPE: RNA
<213> ORGANISM: Artificial Sequence
<220> FEATURE:
<223> OTHER INFORMATION: DYRK1B siRNA 3

<400> SEQUENCE: 49
ggugaaagcc uaugaucau                                                19

<210> SEQ ID NO 50
<211> LENGTH: 19
<212> TYPE: RNA
<213> ORGANISM: Artificial Sequence
<220> FEATURE:
<223> OTHER INFORMATION: DYRK1B siRNA 4

<400> SEQUENCE: 50
ggaccuaccg cuacagcaa                                                19

<210> SEQ ID NO 51
<211> LENGTH: 19
<212> TYPE: RNA
<213> ORGANISM: Artificial Sequence
<220> FEATURE:
<223> OTHER INFORMATION: E2F6 siRNA 1

<400> SEQUENCE: 51
```

-continued caacggaccu aucgauguc                                                    19

<210> SEQ ID NO 52
<211> LENGTH: 19
<212> TYPE: RNA
<213> ORGANISM: Artificial Sequence
<220> FEATURE:
<223> OTHER INFORMATION: E2F6 siRNA 2

<400> SEQUENCE: 52
uagcauaugu gaccuauca                                                    19

<210> SEQ ID NO 53
<211> LENGTH: 19
<212> TYPE: RNA
<213> ORGANISM: Artificial Sequence
<220> FEATURE:
<223> OTHER INFORMATION: E2F6 siRNA 3

<400> SEQUENCE: 53
guaagcaacu gauggcauu                                                    19

<210> SEQ ID NO 54
<211> LENGTH: 19
<212> TYPE: RNA
<213> ORGANISM: Artificial Sequence
<220> FEATURE:
<223> OTHER INFORMATION: E2F6 siRNA 4

<400> SEQUENCE: 54
gaacagaucg ucauugcag                                                    19

<210> SEQ ID NO 55
<211> LENGTH: 19
<212> TYPE: RNA
<213> ORGANISM: Artificial Sequence
<220> FEATURE:
<223> OTHER INFORMATION: E2F7 siRNA 1

<400> SEQUENCE: 55
gcacacaucg ugagacguu                                                    19

<210> SEQ ID NO 56
<211> LENGTH: 19
<212> TYPE: RNA
<213> ORGANISM: Artificial Sequence
<220> FEATURE:
<223> OTHER INFORMATION: E2F7 siRNA 2

<400> SEQUENCE: 56
ugacuaaccu gccgcuuug                                                    19

<210> SEQ ID NO 57
<211> LENGTH: 19
<212> TYPE: RNA
<213> ORGANISM: Artificial Sequence
<220> FEATURE:
<223> OTHER INFORMATION: E2F7 siRNA 3

<400> SEQUENCE: 57
caaggacgau gcauuuaca                                                    19

<210> SEQ ID NO 58
<211> LENGTH: 19
<212> TYPE: RNA

```
<213> ORGANISM: Artificial Sequence
<220> FEATURE:
<223> OTHER INFORMATION: E2F7 siRNA 4

<400> SEQUENCE: 58
ggacuauucc gacccauug                                                    19

<210> SEQ ID NO 59
<211> LENGTH: 19
<212> TYPE: RNA
<213> ORGANISM: Artificial Sequence
<220> FEATURE:
<223> OTHER INFORMATION: EPAS1 siRNA 1

<400> SEQUENCE: 59
ggcagcaccu cacauuuga                                                    19

<210> SEQ ID NO 60
<211> LENGTH: 19
<212> TYPE: RNA
<213> ORGANISM: Artificial Sequence
<220> FEATURE:
<223> OTHER INFORMATION: EPAS1 siRNA 2

<400> SEQUENCE: 60
gagcgcaaau guacccaau                                                    19

<210> SEQ ID NO 61
<211> LENGTH: 19
<212> TYPE: RNA
<213> ORGANISM: Artificial Sequence
<220> FEATURE:
<223> OTHER INFORMATION: EPAS1 siRNA 3

<400> SEQUENCE: 61
gacaaggucu gcaaagggu                                                    19

<210> SEQ ID NO 62
<211> LENGTH: 19
<212> TYPE: RNA
<213> ORGANISM: Artificial Sequence
<220> FEATURE:
<223> OTHER INFORMATION: EPAS1 siRNA 4

<400> SEQUENCE: 62
gcaaagacau guccacaga                                                    19

<210> SEQ ID NO 63
<211> LENGTH: 19
<212> TYPE: RNA
<213> ORGANISM: Artificial Sequence
<220> FEATURE:
<223> OTHER INFORMATION: FOXN2 siRNA 1

<400> SEQUENCE: 63
ccuuuagucu ucucauuua                                                    19

<210> SEQ ID NO 64
<211> LENGTH: 19
<212> TYPE: RNA
<213> ORGANISM: Artificial Sequence
<220> FEATURE:
<223> OTHER INFORMATION: FOXN2 siRNA 2

<400> SEQUENCE: 64
ggaugaggua uaugaauuu                                                    19
```

<210> SEQ ID NO 65
<211> LENGTH: 19
<212> TYPE: RNA
<213> ORGANISM: Artificial Sequence
<220> FEATURE:
<223> OTHER INFORMATION: FOXN2 siRNA 3

<400> SEQUENCE: 65
ggauuaagcc agauuuaca                                                19

<210> SEQ ID NO 66
<211> LENGTH: 19
<212> TYPE: RNA
<213> ORGANISM: Artificial Sequence
<220> FEATURE:
<223> OTHER INFORMATION: FOXN2 siRNA 4

<400> SEQUENCE: 66
caugaaagca cuaaucuuc                                                19

<210> SEQ ID NO 67
<211> LENGTH: 19
<212> TYPE: RNA
<213> ORGANISM: Artificial Sequence
<220> FEATURE:
<223> OTHER INFORMATION: HIVEP2 siRNA 1

<400> SEQUENCE: 67
caucauggcu uccgauuau                                                19

<210> SEQ ID NO 68
<211> LENGTH: 19
<212> TYPE: RNA
<213> ORGANISM: Artificial Sequence
<220> FEATURE:
<223> OTHER INFORMATION: HIVEP2 siRNA 2

<400> SEQUENCE: 68
cgaagcauau gaaaucuaa                                                19

<210> SEQ ID NO 69
<211> LENGTH: 19
<212> TYPE: RNA
<213> ORGANISM: Artificial Sequence
<220> FEATURE:
<223> OTHER INFORMATION: HIVEP2 siRNA 3

<400> SEQUENCE: 69
gcacuuaaga ccuugugua                                                19

<210> SEQ ID NO 70
<211> LENGTH: 19
<212> TYPE: RNA
<213> ORGANISM: Artificial Sequence
<220> FEATURE:
<223> OTHER INFORMATION: HIVEP2 siRNA 4

<400> SEQUENCE: 70
gggauaggau ucaacauug                                                19

<210> SEQ ID NO 71
<211> LENGTH: 19
<212> TYPE: RNA
<213> ORGANISM: Artificial Sequence
<220> FEATURE:

```
<223> OTHER INFORMATION: KANK2 siRNA 1

<400> SEQUENCE: 71
cgugcgaucu aucaugaaa                                                19

<210> SEQ ID NO 72
<211> LENGTH: 19
<212> TYPE: RNA
<213> ORGANISM: Artificial Sequence
<220> FEATURE:
<223> OTHER INFORMATION: KANK2 siRNA 2

<400> SEQUENCE: 72
cagcucacag uacaacuua                                                19

<210> SEQ ID NO 73
<211> LENGTH: 19
<212> TYPE: RNA
<213> ORGANISM: Artificial Sequence
<220> FEATURE:
<223> OTHER INFORMATION: KANK2 siRNA 3

<400> SEQUENCE: 73
gacgagagcc cuacaucau                                                19

<210> SEQ ID NO 74
<211> LENGTH: 19
<212> TYPE: RNA
<213> ORGANISM: Artificial Sequence
<220> FEATURE:
<223> OTHER INFORMATION: KANK2 siRNA 4

<400> SEQUENCE: 74
gaacgggacu ugggcaugc                                                19

<210> SEQ ID NO 75
<211> LENGTH: 19
<212> TYPE: RNA
<213> ORGANISM: Artificial Sequence
<220> FEATURE:
<223> OTHER INFORMATION: LIN54 siRNA 1

<400> SEQUENCE: 75
aaauagugga ggcggaaaa                                                19

<210> SEQ ID NO 76
<211> LENGTH: 19
<212> TYPE: RNA
<213> ORGANISM: Artificial Sequence
<220> FEATURE:
<223> OTHER INFORMATION: LIN54 siRNA 2

<400> SEQUENCE: 76
gaacagggaa uguggguua                                                19

<210> SEQ ID NO 77
<211> LENGTH: 19
<212> TYPE: RNA
<213> ORGANISM: Artificial Sequence
<220> FEATURE:
<223> OTHER INFORMATION: LIN54 siRNA 3

<400> SEQUENCE: 77
gucaggagau gcuaaguua                                                19
```

```
<210> SEQ ID NO 78
<211> LENGTH: 19
<212> TYPE: RNA
<213> ORGANISM: Artificial Sequence
<220> FEATURE:
<223> OTHER INFORMATION: LIN54 siRNA 4

<400> SEQUENCE: 78
gugaaugcua ugaggcaaa                                                19

<210> SEQ ID NO 79
<211> LENGTH: 19
<212> TYPE: RNA
<213> ORGANISM: Artificial Sequence
<220> FEATURE:
<223> OTHER INFORMATION: NCL siRNA 1

<400> SEQUENCE: 79
gcaaagaagg uggucguuu                                                19

<210> SEQ ID NO 80
<211> LENGTH: 19
<212> TYPE: RNA
<213> ORGANISM: Artificial Sequence
<220> FEATURE:
<223> OTHER INFORMATION: NCL siRNA 2

<400> SEQUENCE: 80
gauaguuacu gaccgggaa                                                19

<210> SEQ ID NO 81
<211> LENGTH: 19
<212> TYPE: RNA
<213> ORGANISM: Artificial Sequence
<220> FEATURE:
<223> OTHER INFORMATION: NCL siRNA 3

<400> SEQUENCE: 81
caaaucugcu ccugaauua                                                19

<210> SEQ ID NO 82
<211> LENGTH: 19
<212> TYPE: RNA
<213> ORGANISM: Artificial Sequence
<220> FEATURE:
<223> OTHER INFORMATION: NCL siRNA 4

<400> SEQUENCE: 82
gaaagaagac gaaguuuga                                                19

<210> SEQ ID NO 83
<211> LENGTH: 19
<212> TYPE: RNA
<213> ORGANISM: Artificial Sequence
<220> FEATURE:
<223> OTHER INFORMATION: PNPT1 siRNA 1

<400> SEQUENCE: 83
gacagaagua guauuguaa                                                19

<210> SEQ ID NO 84
<211> LENGTH: 19
<212> TYPE: RNA
<213> ORGANISM: Artificial Sequence
<220> FEATURE:
<223> OTHER INFORMATION: PNPT1 siRNA 2
```

```
<400> SEQUENCE: 84
acagaaagau uauuggcua                                                19

<210> SEQ ID NO 85
<211> LENGTH: 19
<212> TYPE: RNA
<213> ORGANISM: Artificial Sequence
<220> FEATURE:
<223> OTHER INFORMATION: PNPT1 siRNA 3

<400> SEQUENCE: 85
gaauguaagu ugugaggua                                                19

<210> SEQ ID NO 86
<211> LENGTH: 19
<212> TYPE: RNA
<213> ORGANISM: Artificial Sequence
<220> FEATURE:
<223> OTHER INFORMATION: PNPT1 siRNA 4

<400> SEQUENCE: 86
aaucagagau acuggugua                                                19

<210> SEQ ID NO 87
<211> LENGTH: 19
<212> TYPE: RNA
<213> ORGANISM: Artificial Sequence
<220> FEATURE:
<223> OTHER INFORMATION: POLR3E siRNA 1

<400> SEQUENCE: 87
uggauaaggc ugacgccaa                                                19

<210> SEQ ID NO 88
<211> LENGTH: 19
<212> TYPE: RNA
<213> ORGANISM: Artificial Sequence
<220> FEATURE:
<223> OTHER INFORMATION: POLR3E siRNA 2

<400> SEQUENCE: 88
gggagcagau ugcgcugaa                                                19

<210> SEQ ID NO 89
<211> LENGTH: 19
<212> TYPE: RNA
<213> ORGANISM: Artificial Sequence
<220> FEATURE:
<223> OTHER INFORMATION: POLR3E siRNA 3

<400> SEQUENCE: 89
cgacgagacc agcacguau                                                19

<210> SEQ ID NO 90
<211> LENGTH: 19
<212> TYPE: RNA
<213> ORGANISM: Artificial Sequence
<220> FEATURE:
<223> OTHER INFORMATION: POLR3E siRNA 4

<400> SEQUENCE: 90
ccucgaugac cuacgauga                                                19

<210> SEQ ID NO 91
<211> LENGTH: 19
```

```
<212> TYPE: RNA
<213> ORGANISM: Artificial Sequence
<220> FEATURE:
<223> OTHER INFORMATION: RNASEH2A siRNA 1

<400> SEQUENCE: 91
cgggaaaggc uguuugcga                                                    19

<210> SEQ ID NO 92
<211> LENGTH: 19
<212> TYPE: RNA
<213> ORGANISM: Artificial Sequence
<220> FEATURE:
<223> OTHER INFORMATION: RNASEH2A siRNA 2

<400> SEQUENCE: 92
aaauggagga cacggacuu                                                    19

<210> SEQ ID NO 93
<211> LENGTH: 19
<212> TYPE: RNA
<213> ORGANISM: Artificial Sequence
<220> FEATURE:
<223> OTHER INFORMATION: RNASEH2A siRNA 3

<400> SEQUENCE: 93
augcauugga ccagggcgu                                                    19

<210> SEQ ID NO 94
<211> LENGTH: 19
<212> TYPE: RNA
<213> ORGANISM: Artificial Sequence
<220> FEATURE:
<223> OTHER INFORMATION: RNASEH2A siRNA 4

<400> SEQUENCE: 94
agacccuauu ggagagcga                                                    19

<210> SEQ ID NO 95
<211> LENGTH: 19
<212> TYPE: RNA
<213> ORGANISM: Artificial Sequence
<220> FEATURE:
<223> OTHER INFORMATION: RNF4 siRNA 1

<400> SEQUENCE: 95
gcuaauacuu gcccaacuu                                                    19

<210> SEQ ID NO 96
<211> LENGTH: 19
<212> TYPE: RNA
<213> ORGANISM: Artificial Sequence
<220> FEATURE:
<223> OTHER INFORMATION: RNF4 siRNA 2

<400> SEQUENCE: 96
gaauggacgu cucaucguu                                                    19

<210> SEQ ID NO 97
<211> LENGTH: 19
<212> TYPE: RNA
<213> ORGANISM: Artificial Sequence
<220> FEATURE:
<223> OTHER INFORMATION: RNF4 siRNA 3

<400> SEQUENCE: 97
```

```
gacagagacg uauauguga                                                    19

<210> SEQ ID NO 98
<211> LENGTH: 19
<212> TYPE: RNA
<213> ORGANISM: Artificial Sequence
<220> FEATURE:
<223> OTHER INFORMATION: RNF4 siRNA 4

<400> SEQUENCE: 98
gcaauaaauu cuagacaag                                                    19

<210> SEQ ID NO 99
<211> LENGTH: 19
<212> TYPE: RNA
<213> ORGANISM: Artificial Sequence
<220> FEATURE:
<223> OTHER INFORMATION: SERBP1 siRNA 1

<400> SEQUENCE: 99
caaaauaagg accgggcaa                                                    19

<210> SEQ ID NO 100
<211> LENGTH: 19
<212> TYPE: RNA
<213> ORGANISM: Artificial Sequence
<220> FEATURE:
<223> OTHER INFORMATION: SERBP1 siRNA 2

<400> SEQUENCE: 100
aggcugagga agucgguaa                                                    19

<210> SEQ ID NO 101
<211> LENGTH: 19
<212> TYPE: RNA
<213> ORGANISM: Artificial Sequence
<220> FEATURE:
<223> OTHER INFORMATION: SERBP1 siRNA 3

<400> SEQUENCE: 101
gggugaagga ggcgaauuu                                                    19

<210> SEQ ID NO 102
<211> LENGTH: 19
<212> TYPE: RNA
<213> ORGANISM: Artificial Sequence
<220> FEATURE:
<223> OTHER INFORMATION: SERBP1 siRNA 4

<400> SEQUENCE: 102
gaaagaagga auaagacga                                                    19

<210> SEQ ID NO 103
<211> LENGTH: 19
<212> TYPE: RNA
<213> ORGANISM: Artificial Sequence
<220> FEATURE:
<223> OTHER INFORMATION: SKA1 siRNA 1

<400> SEQUENCE: 103
gggaggacuu acucguuau                                                    19

<210> SEQ ID NO 104
<211> LENGTH: 19
<212> TYPE: RNA
<213> ORGANISM: Artificial Sequence
```

```
<220> FEATURE:
<223> OTHER INFORMATION: SKA1 siRNA 2

<400> SEQUENCE: 104
auuauugggc uuucguaua                                                  19

<210> SEQ ID NO 105
<211> LENGTH: 19
<212> TYPE: RNA
<213> ORGANISM: Artificial Sequence
<220> FEATURE:
<223> OTHER INFORMATION: SKA1 siRNA 3

<400> SEQUENCE: 105
ugaagaaccu gaacccgua                                                  19

<210> SEQ ID NO 106
<211> LENGTH: 19
<212> TYPE: RNA
<213> ORGANISM: Artificial Sequence
<220> FEATURE:
<223> OTHER INFORMATION: SKA1 siRNA 4

<400> SEQUENCE: 106
guacaugaaa ucccgcuua                                                  19

<210> SEQ ID NO 107
<211> LENGTH: 19
<212> TYPE: RNA
<213> ORGANISM: Artificial Sequence
<220> FEATURE:
<223> OTHER INFORMATION: SMAD3 siRNA 1

<400> SEQUENCE: 107
caacaggaau gcagcagug                                                  19

<210> SEQ ID NO 108
<211> LENGTH: 19
<212> TYPE: RNA
<213> ORGANISM: Artificial Sequence
<220> FEATURE:
<223> OTHER INFORMATION: SMAD3 siRNA 2

<400> SEQUENCE: 108
gaguucgccu ucaauauga                                                  19

<210> SEQ ID NO 109
<211> LENGTH: 19
<212> TYPE: RNA
<213> ORGANISM: Artificial Sequence
<220> FEATURE:
<223> OTHER INFORMATION: SMAD3 siRNA 3

<400> SEQUENCE: 109
ggacgcaggu ucuccaaac                                                  19

<210> SEQ ID NO 110
<211> LENGTH: 19
<212> TYPE: RNA
<213> ORGANISM: Artificial Sequence
<220> FEATURE:
<223> OTHER INFORMATION: SMAD3 siRNA 4

<400> SEQUENCE: 110
uuagagacau caaguaugg                                                  19
```

```
<210> SEQ ID NO 111
<211> LENGTH: 19
<212> TYPE: RNA
<213> ORGANISM: Artificial Sequence
<220> FEATURE:
<223> OTHER INFORMATION: SNAI2 siRNA 1

<400> SEQUENCE: 111
ucucuccucu uuccggaua                                                    19

<210> SEQ ID NO 112
<211> LENGTH: 19
<212> TYPE: RNA
<213> ORGANISM: Artificial Sequence
<220> FEATURE:
<223> OTHER INFORMATION: SNAI2 siRNA 2

<400> SEQUENCE: 112
gcgaugccca gucuagaaa                                                    19

<210> SEQ ID NO 113
<211> LENGTH: 19
<212> TYPE: RNA
<213> ORGANISM: Artificial Sequence
<220> FEATURE:
<223> OTHER INFORMATION: SNAI2 siRNA 3

<400> SEQUENCE: 113
acagcgaacu ggacacaca                                                    19

<210> SEQ ID NO 114
<211> LENGTH: 19
<212> TYPE: RNA
<213> ORGANISM: Artificial Sequence
<220> FEATURE:
<223> OTHER INFORMATION: SNAI2 siRNA 4

<400> SEQUENCE: 114
gaaugucucu ccugcacaa                                                    19

<210> SEQ ID NO 115
<211> LENGTH: 19
<212> TYPE: RNA
<213> ORGANISM: Artificial Sequence
<220> FEATURE:
<223> OTHER INFORMATION: SOX7 siRNA 1

<400> SEQUENCE: 115
agagcaacuu cccgcaaau                                                    19

<210> SEQ ID NO 116
<211> LENGTH: 19
<212> TYPE: RNA
<213> ORGANISM: Artificial Sequence
<220> FEATURE:
<223> OTHER INFORMATION: SOX7 siRNA 2

<400> SEQUENCE: 116
gaaaauggga uugaguuaa                                                    19

<210> SEQ ID NO 117
<211> LENGTH: 19
<212> TYPE: RNA
<213> ORGANISM: Artificial Sequence
<220> FEATURE:
<223> OTHER INFORMATION: SOX7 siRNA 3
```

```
<400> SEQUENCE: 117
caaagggacu cauacaauu                                                19

<210> SEQ ID NO 118
<211> LENGTH: 19
<212> TYPE: RNA
<213> ORGANISM: Artificial Sequence
<220> FEATURE:
<223> OTHER INFORMATION: SOX7 siRNA 4

<400> SEQUENCE: 118
gcauaacagu gugcugaaa                                                19

<210> SEQ ID NO 119
<211> LENGTH: 19
<212> TYPE: RNA
<213> ORGANISM: Artificial Sequence
<220> FEATURE:
<223> OTHER INFORMATION: SSB siRNA 1

<400> SEQUENCE: 119
ggucguagau uuaaaggaa                                                19

<210> SEQ ID NO 120
<211> LENGTH: 19
<212> TYPE: RNA
<213> ORGANISM: Artificial Sequence
<220> FEATURE:
<223> OTHER INFORMATION: SSB siRNA 2

<400> SEQUENCE: 120
gguuagaaga uaaagguca                                                19

<210> SEQ ID NO 121
<211> LENGTH: 19
<212> TYPE: RNA
<213> ORGANISM: Artificial Sequence
<220> FEATURE:
<223> OTHER INFORMATION: SSB siRNA 3

<400> SEQUENCE: 121
gagaccagua guuuaguaa                                                19

<210> SEQ ID NO 122
<211> LENGTH: 19
<212> TYPE: RNA
<213> ORGANISM: Artificial Sequence
<220> FEATURE:
<223> OTHER INFORMATION: SSB siRNA 4

<400> SEQUENCE: 122
gggaaguacu agaaggaga                                                19

<210> SEQ ID NO 123
<211> LENGTH: 19
<212> TYPE: RNA
<213> ORGANISM: Artificial Sequence
<220> FEATURE:
<223> OTHER INFORMATION: STAM siRNA 1

<400> SEQUENCE: 123
gaacgaagau ccgauguau                                                19

<210> SEQ ID NO 124
```

```
<211> LENGTH: 19
<212> TYPE: RNA
<213> ORGANISM: Artificial Sequence
<220> FEATURE:
<223> OTHER INFORMATION: STAM siRNA 2

<400> SEQUENCE: 124
ccacaaagau ccucacguu                                                   19

<210> SEQ ID NO 125
<211> LENGTH: 19
<212> TYPE: RNA
<213> ORGANISM: Artificial Sequence
<220> FEATURE:
<223> OTHER INFORMATION: STAM siRNA 3

<400> SEQUENCE: 125
ggaguuacgu ucccagcua                                                   19

<210> SEQ ID NO 126
<211> LENGTH: 19
<212> TYPE: RNA
<213> ORGANISM: Artificial Sequence
<220> FEATURE:
<223> OTHER INFORMATION: STAM siRNA 4

<400> SEQUENCE: 126
cauccagucu cuuaacuaa                                                   19

<210> SEQ ID NO 127
<211> LENGTH: 19
<212> TYPE: RNA
<213> ORGANISM: Artificial Sequence
<220> FEATURE:
<223> OTHER INFORMATION: TFAP2A siRNA 1

<400> SEQUENCE: 127
guauuaacau cccagauca                                                   19

<210> SEQ ID NO 128
<211> LENGTH: 19
<212> TYPE: RNA
<213> ORGANISM: Artificial Sequence
<220> FEATURE:
<223> OTHER INFORMATION: TFAP2A siRNA 2

<400> SEQUENCE: 128
cguaaagcug ccaacguua                                                   19

<210> SEQ ID NO 129
<211> LENGTH: 19
<212> TYPE: RNA
<213> ORGANISM: Artificial Sequence
<220> FEATURE:
<223> OTHER INFORMATION: TFAP2A siRNA 3

<400> SEQUENCE: 129
ccaccuagcc agggacuuu                                                   19

<210> SEQ ID NO 130
<211> LENGTH: 19
<212> TYPE: RNA
<213> ORGANISM: Artificial Sequence
<220> FEATURE:
<223> OTHER INFORMATION: TFAP2A siRNA 4

<400> SEQUENCE: 130
```

-continued uaacaaggac aaccucuuc                                        19

<210> SEQ ID NO 131
<211> LENGTH: 19
<212> TYPE: RNA
<213> ORGANISM: Artificial Sequence
<220> FEATURE:
<223> OTHER INFORMATION: TFAP2C siRNA 1

<400> SEQUENCE: 131
ccgauaaugu caaguacga                                        19

<210> SEQ ID NO 132
<211> LENGTH: 19
<212> TYPE: RNA
<213> ORGANISM: Artificial Sequence
<220> FEATURE:
<223> OTHER INFORMATION: TFAP2C siRNA 2

<400> SEQUENCE: 132
acacuggagu cgccgaaua                                        19

<210> SEQ ID NO 133
<211> LENGTH: 19
<212> TYPE: RNA
<213> ORGANISM: Artificial Sequence
<220> FEATURE:
<223> OTHER INFORMATION: TFAP2C siRNA 3

<400> SEQUENCE: 133
guaaaccagu ggcagaaua                                        19

<210> SEQ ID NO 134
<211> LENGTH: 19
<212> TYPE: RNA
<213> ORGANISM: Artificial Sequence
<220> FEATURE:
<223> OTHER INFORMATION: TFAP2C siRNA 4

<400> SEQUENCE: 134
ggacaagauu ggguugaau                                        19

<210> SEQ ID NO 135
<211> LENGTH: 19
<212> TYPE: RNA
<213> ORGANISM: Artificial Sequence
<220> FEATURE:
<223> OTHER INFORMATION: TFB2M siRNA 1

<400> SEQUENCE: 135
caaaugauuc cucgucaaa                                        19

<210> SEQ ID NO 136
<211> LENGTH: 19
<212> TYPE: RNA
<213> ORGANISM: Artificial Sequence
<220> FEATURE:
<223> OTHER INFORMATION: TFB2M siRNA 2

<400> SEQUENCE: 136
accaagaacu uaacaccua                                        19

<210> SEQ ID NO 137
<211> LENGTH: 19
<212> TYPE: RNA

```
<213> ORGANISM: Artificial Sequence
<220> FEATURE:
<223> OTHER INFORMATION: TFB2M siRNA 3

<400> SEQUENCE: 137
gaaacucgca uaugacuug                                                 19

<210> SEQ ID NO 138
<211> LENGTH: 19
<212> TYPE: RNA
<213> ORGANISM: Artificial Sequence
<220> FEATURE:
<223> OTHER INFORMATION: TFB2M siRNA 4

<400> SEQUENCE: 138
gaucggagau uggcugaga                                                 19

<210> SEQ ID NO 139
<211> LENGTH: 19
<212> TYPE: RNA
<213> ORGANISM: Artificial Sequence
<220> FEATURE:
<223> OTHER INFORMATION: TP73 siRNA 1

<400> SEQUENCE: 139
gagacgagga cacguacua                                                 19

<210> SEQ ID NO 140
<211> LENGTH: 19
<212> TYPE: RNA
<213> ORGANISM: Artificial Sequence
<220> FEATURE:
<223> OTHER INFORMATION: TP73 siRNA 2

<400> SEQUENCE: 140
gcaauaaucu cucgcagua                                                 19

<210> SEQ ID NO 141
<211> LENGTH: 19
<212> TYPE: RNA
<213> ORGANISM: Artificial Sequence
<220> FEATURE:
<223> OTHER INFORMATION: TP73 siRNA 3

<400> SEQUENCE: 141
gaacuuugag auccugaug                                                 19

<210> SEQ ID NO 142
<211> LENGTH: 19
<212> TYPE: RNA
<213> ORGANISM: Artificial Sequence
<220> FEATURE:
<223> OTHER INFORMATION: TP73 siRNA 4

<400> SEQUENCE: 142
ccaccauccu guacaacuu                                                 19

<210> SEQ ID NO 143
<211> LENGTH: 19
<212> TYPE: RNA
<213> ORGANISM: Artificial Sequence
<220> FEATURE:
<223> OTHER INFORMATION: TRIM24 siRNA 1

<400> SEQUENCE: 143
gagcauagau accaauuua                                                 19
```

<210> SEQ ID NO 144
<211> LENGTH: 19
<212> TYPE: RNA
<213> ORGANISM: Artificial Sequence
<220> FEATURE:
<223> OTHER INFORMATION: TRIM24 siRNA 2

<400> SEQUENCE: 144
gaagaacgcc aguugcuua                                                19

<210> SEQ ID NO 145
<211> LENGTH: 19
<212> TYPE: RNA
<213> ORGANISM: Artificial Sequence
<220> FEATURE:
<223> OTHER INFORMATION: TRIM24 siRNA 3

<400> SEQUENCE: 145
gaucauagau acacuaauc                                                19

<210> SEQ ID NO 146
<211> LENGTH: 19
<212> TYPE: RNA
<213> ORGANISM: Artificial Sequence
<220> FEATURE:
<223> OTHER INFORMATION: TRIM24 siRNA 4

<400> SEQUENCE: 146
uaacugugcc ugauuauua                                                19

<210> SEQ ID NO 147
<211> LENGTH: 19
<212> TYPE: RNA
<213> ORGANISM: Artificial Sequence
<220> FEATURE:
<223> OTHER INFORMATION: TRIM27 siRNA 1

<400> SEQUENCE: 147
cggagagucu aaagcaguu                                                19

<210> SEQ ID NO 148
<211> LENGTH: 19
<212> TYPE: RNA
<213> ORGANISM: Artificial Sequence
<220> FEATURE:
<223> OTHER INFORMATION: TRIM27 siRNA 2

<400> SEQUENCE: 148
gaaccagcuc gaccauuua                                                19

<210> SEQ ID NO 149
<211> LENGTH: 19
<212> TYPE: RNA
<213> ORGANISM: Artificial Sequence
<220> FEATURE:
<223> OTHER INFORMATION: TRIM27 siRNA 3

<400> SEQUENCE: 149
gagaugggcg ugugcgaga                                                19

<210> SEQ ID NO 150
<211> LENGTH: 19
<212> TYPE: RNA
<213> ORGANISM: Artificial Sequence
<220> FEATURE:

```
<223> OTHER INFORMATION: TRIM27 siRNA 4

<400> SEQUENCE: 150
uaagagaggc ucaguuaua                                                19

<210> SEQ ID NO 151
<211> LENGTH: 19
<212> TYPE: RNA
<213> ORGANISM: Artificial Sequence
<220> FEATURE:
<223> OTHER INFORMATION: TRIM68 siRNA 1

<400> SEQUENCE: 151
gaagggaaau gaguaccga                                                19

<210> SEQ ID NO 152
<211> LENGTH: 19
<212> TYPE: RNA
<213> ORGANISM: Artificial Sequence
<220> FEATURE:
<223> OTHER INFORMATION: TRIM68 siRNA 2

<400> SEQUENCE: 152
gaacuggggu uacaccugu                                                19

<210> SEQ ID NO 153
<211> LENGTH: 19
<212> TYPE: RNA
<213> ORGANISM: Artificial Sequence
<220> FEATURE:
<223> OTHER INFORMATION: TRIM68 siRNA 3

<400> SEQUENCE: 153
gagagauccu gaagacuua                                                19

<210> SEQ ID NO 154
<211> LENGTH: 19
<212> TYPE: RNA
<213> ORGANISM: Artificial Sequence
<220> FEATURE:
<223> OTHER INFORMATION: TRIM68 siRNA 4

<400> SEQUENCE: 154
gaggaugucu ugauaaugu                                                19

<210> SEQ ID NO 155
<211> LENGTH: 19
<212> TYPE: RNA
<213> ORGANISM: Artificial Sequence
<220> FEATURE:
<223> OTHER INFORMATION: WDR54 siRNA 1

<400> SEQUENCE: 155
gcuaugaccu ugcggagau                                                19

<210> SEQ ID NO 156
<211> LENGTH: 19
<212> TYPE: RNA
<213> ORGANISM: Artificial Sequence
<220> FEATURE:
<223> OTHER INFORMATION: WDR54 siRNA 2

<400> SEQUENCE: 156
ccaacauugu acugagcga                                                19
```

```
<210> SEQ ID NO 157
<211> LENGTH: 19
<212> TYPE: RNA
<213> ORGANISM: Artificial Sequence
<220> FEATURE:
<223> OTHER INFORMATION: WDR54 siRNA 3

<400> SEQUENCE: 157
aggcuauggg aacggacaa                                              19

<210> SEQ ID NO 158
<211> LENGTH: 19
<212> TYPE: RNA
<213> ORGANISM: Artificial Sequence
<220> FEATURE:
<223> OTHER INFORMATION: WDR54 siRNA 4

<400> SEQUENCE: 158
gcucgcaacc ucacguauu                                              19

<210> SEQ ID NO 159
<211> LENGTH: 19
<212> TYPE: RNA
<213> ORGANISM: Artificial Sequence
<220> FEATURE:
<223> OTHER INFORMATION: ZNF518A siRNA 1

<400> SEQUENCE: 159
cgauauagcc caaaugauu                                              19

<210> SEQ ID NO 160
<211> LENGTH: 19
<212> TYPE: RNA
<213> ORGANISM: Artificial Sequence
<220> FEATURE:
<223> OTHER INFORMATION: ZNF518A siRNA 2

<400> SEQUENCE: 160
gcuaauauuc gcagcacua                                              19

<210> SEQ ID NO 161
<211> LENGTH: 19
<212> TYPE: RNA
<213> ORGANISM: Artificial Sequence
<220> FEATURE:
<223> OTHER INFORMATION: ZNF518A siRNA 3

<400> SEQUENCE: 161
cuugcuaagu auucaguaa                                              19

<210> SEQ ID NO 162
<211> LENGTH: 19
<212> TYPE: RNA
<213> ORGANISM: Artificial Sequence
<220> FEATURE:
<223> OTHER INFORMATION: ZNF518A siRNA 4

<400> SEQUENCE: 162
gcaaaggacg guacugcua                                              19

<210> SEQ ID NO 163
<211> LENGTH: 19
<212> TYPE: RNA
<213> ORGANISM: Artificial Sequence
<220> FEATURE:
<223> OTHER INFORMATION: HNF4a siRNA 1
```

```
<400> SEQUENCE: 163
gaccggauca gcacucgaa                                                  19

<210> SEQ ID NO 164
<211> LENGTH: 19
<212> TYPE: RNA
<213> ORGANISM: Artificial Sequence
<220> FEATURE:
<223> OTHER INFORMATION: HNF4a siRNA 2

<400> SEQUENCE: 164
cggaagaacc acauguacu                                                  19

<210> SEQ ID NO 165
<211> LENGTH: 19
<212> TYPE: RNA
<213> ORGANISM: Artificial Sequence
<220> FEATURE:
<223> OTHER INFORMATION: HNF4a siRNA 3

<400> SEQUENCE: 165
gggcuggcau gaagaagga                                                  19

<210> SEQ ID NO 166
<211> LENGTH: 19
<212> TYPE: RNA
<213> ORGANISM: Artificial Sequence
<220> FEATURE:
<223> OTHER INFORMATION: HNF4a siRNA 4

<400> SEQUENCE: 166
ccaaguacau cccagcuuu                                                  19

<210> SEQ ID NO 167
<211> LENGTH: 19
<212> TYPE: RNA
<213> ORGANISM: Artificial Sequence
<220> FEATURE:
<223> OTHER INFORMATION: CPD siRNA 1

<400> SEQUENCE: 167
gaaauucgca ugaugucua                                                  19

<210> SEQ ID NO 168
<211> LENGTH: 19
<212> TYPE: RNA
<213> ORGANISM: Artificial Sequence
<220> FEATURE:
<223> OTHER INFORMATION: CPD siRNA 2

<400> SEQUENCE: 168
gaacuagguu gugugaaau                                                  19

<210> SEQ ID NO 169
<211> LENGTH: 19
<212> TYPE: RNA
<213> ORGANISM: Artificial Sequence
<220> FEATURE:
<223> OTHER INFORMATION: CPD siRNA 3

<400> SEQUENCE: 169
ggagaacaau cgugagucu                                                  19

<210> SEQ ID NO 170
<211> LENGTH: 19
```

```
<212> TYPE: RNA
<213> ORGANISM: Artificial Sequence
<220> FEATURE:
<223> OTHER INFORMATION: CPD siRNA 4

<400> SEQUENCE: 170
gcacaguugc uauaccuaa                                                  19

<210> SEQ ID NO 171
<211> LENGTH: 19
<212> TYPE: RNA
<213> ORGANISM: Artificial Sequence
<220> FEATURE:
<223> OTHER INFORMATION: CSNK2A2 siRNA 1

<400> SEQUENCE: 171
gaguuugggc uguauguua                                                  19

<210> SEQ ID NO 172
<211> LENGTH: 19
<212> TYPE: RNA
<213> ORGANISM: Artificial Sequence
<220> FEATURE:
<223> OTHER INFORMATION: CSNK2A2 siRNA 2

<400> SEQUENCE: 172
gggacaacau ucacggaaa                                                  19

<210> SEQ ID NO 173
<211> LENGTH: 19
<212> TYPE: RNA
<213> ORGANISM: Artificial Sequence
<220> FEATURE:
<223> OTHER INFORMATION: CSNK2A2 siRNA 3

<400> SEQUENCE: 173
gauagaucac caacagaaa                                                  19

<210> SEQ ID NO 174
<211> LENGTH: 19
<212> TYPE: RNA
<213> ORGANISM: Artificial Sequence
<220> FEATURE:
<223> OTHER INFORMATION: CSNK2A2 siRNA 4

<400> SEQUENCE: 174
uuaagcaacu cuaccagau                                                  19

<210> SEQ ID NO 175
<211> LENGTH: 19
<212> TYPE: RNA
<213> ORGANISM: Artificial Sequence
<220> FEATURE:
<223> OTHER INFORMATION: HERPUD1 siRNA 1

<400> SEQUENCE: 175
cgacaguacu acaugcaau                                                  19

<210> SEQ ID NO 176
<211> LENGTH: 19
<212> TYPE: RNA
<213> ORGANISM: Artificial Sequence
<220> FEATURE:
<223> OTHER INFORMATION: HERPUD1 siRNA 2

<400> SEQUENCE: 176
```
gggccaccgu uguuaugua                                    19

<210> SEQ ID NO 177
<211> LENGTH: 19
<212> TYPE: RNA
<213> ORGANISM: Artificial Sequence
<220> FEATURE:
<223> OTHER INFORMATION: HERPUD1 siRNA 3

<400> SEQUENCE: 177
ggcuucagcu uuccugguu                                    19

<210> SEQ ID NO 178
<211> LENGTH: 19
<212> TYPE: RNA
<213> ORGANISM: Artificial Sequence
<220> FEATURE:
<223> OTHER INFORMATION: HERPUD1 siRNA 4

<400> SEQUENCE: 178
gcggaugaau gcacaaggu                                    19

<210> SEQ ID NO 179
<211> LENGTH: 19
<212> TYPE: RNA
<213> ORGANISM: Artificial Sequence
<220> FEATURE:
<223> OTHER INFORMATION: KPNA3 siRNA 1

<400> SEQUENCE: 179
gucaaucucu gcaggaaua                                    19

<210> SEQ ID NO 180
<211> LENGTH: 19
<212> TYPE: RNA
<213> ORGANISM: Artificial Sequence
<220> FEATURE:
<223> OTHER INFORMATION: KPNA3 siRNA 2

<400> SEQUENCE: 180
gauaauggcc ggugaugaa                                    19

<210> SEQ ID NO 181
<211> LENGTH: 19
<212> TYPE: RNA
<213> ORGANISM: Artificial Sequence
<220> FEATURE:
<223> OTHER INFORMATION: KPNA3 siRNA 3

<400> SEQUENCE: 181
gaaaagauca gguugagua                                    19

<210> SEQ ID NO 182
<211> LENGTH: 19
<212> TYPE: RNA
<213> ORGANISM: Artificial Sequence
<220> FEATURE:
<223> OTHER INFORMATION: KPNA3 siRNA 4

<400> SEQUENCE: 182
acaaggaggu accacaau                                     19

<210> SEQ ID NO 183
<211> LENGTH: 19
<212> TYPE: RNA
<213> ORGANISM: Artificial Sequence

```
<220> FEATURE:
<223> OTHER INFORMATION: PAK1IP1 siRNA 1

<400> SEQUENCE: 183
cuagugugcc ucugcgaau                                              19

<210> SEQ ID NO 184
<211> LENGTH: 19
<212> TYPE: RNA
<213> ORGANISM: Artificial Sequence
<220> FEATURE:
<223> OTHER INFORMATION: PAK1IP1 siRNA 2

<400> SEQUENCE: 184
uuuaaucagu ggagcggaa                                              19

<210> SEQ ID NO 185
<211> LENGTH: 19
<212> TYPE: RNA
<213> ORGANISM: Artificial Sequence
<220> FEATURE:
<223> OTHER INFORMATION: PAK1IP1 siRNA 3

<400> SEQUENCE: 185
caucacagug guacaauaa                                              19

<210> SEQ ID NO 186
<211> LENGTH: 19
<212> TYPE: RNA
<213> ORGANISM: Artificial Sequence
<220> FEATURE:
<223> OTHER INFORMATION: PAK1IP1 siRNA 4

<400> SEQUENCE: 186
gucgguuggu acagauaaa                                              19

<210> SEQ ID NO 187
<211> LENGTH: 19
<212> TYPE: RNA
<213> ORGANISM: Artificial Sequence
<220> FEATURE:
<223> OTHER INFORMATION: PRDX3 siRNA 1

<400> SEQUENCE: 187
guagaucacc cauguguau                                              19

<210> SEQ ID NO 188
<211> LENGTH: 19
<212> TYPE: RNA
<213> ORGANISM: Artificial Sequence
<220> FEATURE:
<223> OTHER INFORMATION: PRDX3 siRNA 2

<400> SEQUENCE: 188
gaacaucgca cucuuguca                                              19

<210> SEQ ID NO 189
<211> LENGTH: 19
<212> TYPE: RNA
<213> ORGANISM: Artificial Sequence
<220> FEATURE:
<223> OTHER INFORMATION: PRDX3 siRNA 3

<400> SEQUENCE: 189
agacuacggu gugcuguua                                              19
```

```
<210> SEQ ID NO 190
<211> LENGTH: 19
<212> TYPE: RNA
<213> ORGANISM: Artificial Sequence
<220> FEATURE:
<223> OTHER INFORMATION: PRDX3 siRNA 4

<400> SEQUENCE: 190
gagcuugaca aauuuauug                                                19

<210> SEQ ID NO 191
<211> LENGTH: 19
<212> TYPE: RNA
<213> ORGANISM: Artificial Sequence
<220> FEATURE:
<223> OTHER INFORMATION: PTP4A1 siRNA 1

<400> SEQUENCE: 191
gauuguugau gacugguua                                                19

<210> SEQ ID NO 192
<211> LENGTH: 19
<212> TYPE: RNA
<213> ORGANISM: Artificial Sequence
<220> FEATURE:
<223> OTHER INFORMATION: PTP4A1 siRNA 2

<400> SEQUENCE: 192
ccaaugcgac cuuaaacaa                                                19

<210> SEQ ID NO 193
<211> LENGTH: 19
<212> TYPE: RNA
<213> ORGANISM: Artificial Sequence
<220> FEATURE:
<223> OTHER INFORMATION: PTP4A1 siRNA 3

<400> SEQUENCE: 193
gcaagcaacu ucuguauuu                                                19

<210> SEQ ID NO 194
<211> LENGTH: 19
<212> TYPE: RNA
<213> ORGANISM: Artificial Sequence
<220> FEATURE:
<223> OTHER INFORMATION: PTP4A1 siRNA 4

<400> SEQUENCE: 194
gaaagaaggu auccauguu                                                19

<210> SEQ ID NO 195
<211> LENGTH: 19
<212> TYPE: RNA
<213> ORGANISM: Artificial Sequence
<220> FEATURE:
<223> OTHER INFORMATION: RHOB siRNA 1

<400> SEQUENCE: 195
gcauccaagc cuacgacua                                                19

<210> SEQ ID NO 196
<211> LENGTH: 19
<212> TYPE: RNA
<213> ORGANISM: Artificial Sequence
<220> FEATURE:
<223> OTHER INFORMATION: RHOB siRNA 2
```

<400> SEQUENCE: 196
cagaacggcu gcaucaacu                                                    19

<210> SEQ ID NO 197
<211> LENGTH: 19
<212> TYPE: RNA
<213> ORGANISM: Artificial Sequence
<220> FEATURE:
<223> OTHER INFORMATION: RHOB siRNA 3

<400> SEQUENCE: 197
cgacgagcau guccgcaca                                                    19

<210> SEQ ID NO 198
<211> LENGTH: 19
<212> TYPE: RNA
<213> ORGANISM: Artificial Sequence
<220> FEATURE:
<223> OTHER INFORMATION: RHOB siRNA 4

<400> SEQUENCE: 198
aagcacuucu gucccaaug                                                    19

<210> SEQ ID NO 199
<211> LENGTH: 19
<212> TYPE: RNA
<213> ORGANISM: Artificial Sequence
<220> FEATURE:
<223> OTHER INFORMATION: RNF43 siRNA 1

<400> SEQUENCE: 199
gcagaacaga aagcuauua                                                    19

<210> SEQ ID NO 200
<211> LENGTH: 19
<212> TYPE: RNA
<213> ORGANISM: Artificial Sequence
<220> FEATURE:
<223> OTHER INFORMATION: RNF43 siRNA 2

<400> SEQUENCE: 200
uaugaugugu ggauccuaa                                                    19

<210> SEQ ID NO 201
<211> LENGTH: 19
<212> TYPE: RNA
<213> ORGANISM: Artificial Sequence
<220> FEATURE:
<223> OTHER INFORMATION: RNF43 siRNA 3

<400> SEQUENCE: 201
ggagaaagcu auugcacag                                                    19

<210> SEQ ID NO 202
<211> LENGTH: 19
<212> TYPE: RNA
<213> ORGANISM: Artificial Sequence
<220> FEATURE:
<223> OTHER INFORMATION: RNF43 siRNA 4

<400> SEQUENCE: 202
gguggagucu gaaagauca                                                    19

<210> SEQ ID NO 203

```
<210> SEQ ID NO 203
<211> LENGTH: 19
<212> TYPE: RNA
<213> ORGANISM: Artificial Sequence
<220> FEATURE:
<223> OTHER INFORMATION: SRPK1 siRNA 1

<400> SEQUENCE: 203
gaacauaacg gaccacugg                                                   19

<210> SEQ ID NO 204
<211> LENGTH: 19
<212> TYPE: RNA
<213> ORGANISM: Artificial Sequence
<220> FEATURE:
<223> OTHER INFORMATION: SRPK1 siRNA 2

<400> SEQUENCE: 204
gauaccaugu gauccgaaa                                                   19

<210> SEQ ID NO 205
<211> LENGTH: 19
<212> TYPE: RNA
<213> ORGANISM: Artificial Sequence
<220> FEATURE:
<223> OTHER INFORMATION: SRPK1 siRNA 3

<400> SEQUENCE: 205
gcagcuggcu ucacagauu                                                   19

<210> SEQ ID NO 206
<211> LENGTH: 19
<212> TYPE: RNA
<213> ORGANISM: Artificial Sequence
<220> FEATURE:
<223> OTHER INFORMATION: SRPK1 siRNA 4

<400> SEQUENCE: 206
acacauaucu gcaugguau                                                   19

<210> SEQ ID NO 207
<211> LENGTH: 19
<212> TYPE: RNA
<213> ORGANISM: Artificial Sequence
<220> FEATURE:
<223> OTHER INFORMATION: STRADB siRNA 1

<400> SEQUENCE: 207
gcaccaaaau ggcuguauu                                                   19

<210> SEQ ID NO 208
<211> LENGTH: 19
<212> TYPE: RNA
<213> ORGANISM: Artificial Sequence
<220> FEATURE:
<223> OTHER INFORMATION: STRADB siRNA 2

<400> SEQUENCE: 208
gggauuacag caugugaau                                                   19

<210> SEQ ID NO 209
<211> LENGTH: 19
<212> TYPE: RNA
<213> ORGANISM: Artificial Sequence
<220> FEATURE:
<223> OTHER INFORMATION: STRADB siRNA 3

<400> SEQUENCE: 209
```

```
aguaaauagu gaccgauua                                                    19

<210> SEQ ID NO 210
<211> LENGTH: 19
<212> TYPE: RNA
<213> ORGANISM: Artificial Sequence
<220> FEATURE:
<223> OTHER INFORMATION: STRADB siRNA 4

<400> SEQUENCE: 210
gguauaaugu gaagucaga                                                    19

<210> SEQ ID NO 211
<211> LENGTH: 19
<212> TYPE: RNA
<213> ORGANISM: Artificial Sequence
<220> FEATURE:
<223> OTHER INFORMATION: STT3B siRNA 1

<400> SEQUENCE: 211
gagcaucaac cuacgacuu                                                    19

<210> SEQ ID NO 212
<211> LENGTH: 19
<212> TYPE: RNA
<213> ORGANISM: Artificial Sequence
<220> FEATURE:
<223> OTHER INFORMATION: STT3B siRNA 2

<400> SEQUENCE: 212
gaucacaaac cucgaguca                                                    19

<210> SEQ ID NO 213
<211> LENGTH: 19
<212> TYPE: RNA
<213> ORGANISM: Artificial Sequence
<220> FEATURE:
<223> OTHER INFORMATION: STT3B siRNA 3

<400> SEQUENCE: 213
agaugaacau gcacgagua                                                    19

<210> SEQ ID NO 214
<211> LENGTH: 19
<212> TYPE: RNA
<213> ORGANISM: Artificial Sequence
<220> FEATURE:
<223> OTHER INFORMATION: STT3B siRNA 4

<400> SEQUENCE: 214
acauagcacu ggugggaaa                                                    19

<210> SEQ ID NO 215
<211> LENGTH: 14
<212> TYPE: PRT
<213> ORGANISM: Artificial Sequence
<220> FEATURE:
<223> OTHER INFORMATION: Slug-ZF1s

<400> SEQUENCE: 215

Tyr Ser Thr Phe Ser Gly Leu Ala Lys His Lys Gln Leu His
1               5                   10

<210> SEQ ID NO 216
<211> LENGTH: 16
```

<212> TYPE: PRT
<213> ORGANISM: Artificial Sequence
<220> FEATURE:
<223> OTHER INFORMATION: Slug-ZF2s

<400> SEQUENCE: 216

Lys Glu Tyr Val Ser Leu Gly Ala Leu Lys Met His Ile Arg Thr His
1               5                   10                  15

<210> SEQ ID NO 217
<211> LENGTH: 16
<212> TYPE: PRT
<213> ORGANISM: Artificial Sequence
<220> FEATURE:
<223> OTHER INFORMATION: Slug-ZF3s

<400> SEQUENCE: 217

Lys Ala Phe Ser Arg Pro Trp Leu Leu Gln Gly His Ile Arg Thr His
1               5                   10                  15

<210> SEQ ID NO 218
<211> LENGTH: 14
<212> TYPE: PRT
<213> ORGANISM: Artificial Sequence
<220> FEATURE:
<223> OTHER INFORMATION: Slug-ZF4s

<400> SEQUENCE: 218

Phe Ala Asp Arg Ser Asn Leu Arg Ala His Leu Gln Thr His
1               5                   10

<210> SEQ ID NO 219
<211> LENGTH: 13
<212> TYPE: PRT
<213> ORGANISM: Artificial Sequence
<220> FEATURE:
<223> OTHER INFORMATION: Slug-ZF5s

<400> SEQUENCE: 219

Phe Ser Arg Met Ser Leu Leu His Lys His Glu Glu Ser
1               5                   10

<210> SEQ ID NO 220
<211> LENGTH: 14
<212> TYPE: PRT
<213> ORGANISM: Artificial Sequence
<220> FEATURE:
<223> OTHER INFORMATION: Sox7-H1s

<400> SEQUENCE: 220

Ala Phe Met Val Trp Ala Lys Asp Glu Arg Lys Arg Leu Ala
1               5                   10

<210> SEQ ID NO 221
<211> LENGTH: 15
<212> TYPE: PRT
<213> ORGANISM: Artificial Sequence
<220> FEATURE:
<223> OTHER INFORMATION: Sox7-H2s

<400> SEQUENCE: 221

His Asn Ala Glu Leu Ser Lys Met Leu Gly Lys Ser Trp Lys Ala
1               5                   10                  15

<210> SEQ ID NO 222
<211> LENGTH: 18
<212> TYPE: DNA

```
<213> ORGANISM: Artificial Sequence
<220> FEATURE:
<223> OTHER INFORMATION: Slug-F Primer

<400> SEQUENCE: 222
cgatgctgta gggaccgc                                                 18

<210> SEQ ID NO 223
<211> LENGTH: 22
<212> TYPE: DNA
<213> ORGANISM: Artificial Sequence
<220> FEATURE:
<223> OTHER INFORMATION: Slug-R Primer

<400> SEQUENCE: 223
tggtcagcac aggagaaaat gc                                            22

<210> SEQ ID NO 224
<211> LENGTH: 25
<212> TYPE: DNA
<213> ORGANISM: Artificial Sequence
<220> FEATURE:
<223> OTHER INFORMATION: Sox7-F Primer

<400> SEQUENCE: 224
tatgctagca tggcttcgct gctgg                                         25

<210> SEQ ID NO 225
<211> LENGTH: 34
<212> TYPE: DNA
<213> ORGANISM: Artificial Sequence
<220> FEATURE:
<223> OTHER INFORMATION: Sox7-R Primer

<400> SEQUENCE: 225
taatctagac tatgacacac tgtagctgtt gtag                               34

<210> SEQ ID NO 226
<211> LENGTH: 15
<212> TYPE: DNA
<213> ORGANISM: Artificial Sequence
<220> FEATURE:
<223> OTHER INFORMATION: Hepatitis B Virus ( 5' nt 1813-1827)

<400> SEQUENCE: 226
ccatgcaact ttttc                                                    15

<210> SEQ ID NO 227
<211> LENGTH: 15
<212> TYPE: DNA
<213> ORGANISM: Artificial Sequence
<220> FEATURE:
<223> OTHER INFORMATION: Hepatitis B Virus (complement to 5' nt 1813-
      1827)

<400> SEQUENCE: 227
ggtacgttga aaaag                                                    15

<210> SEQ ID NO 228
<211> LENGTH: 24
<212> TYPE: DNA
<213> ORGANISM: Artificial Sequence
<220> FEATURE:
<223> OTHER INFORMATION: WT Slug probe

<400> SEQUENCE: 228
```
agcaccatgc aactttttca cctc                                            24

<210> SEQ ID NO 229
<211> LENGTH: 18
<212> TYPE: DNA
<213> ORGANISM: Artificial Sequence
<220> FEATURE:
<223> OTHER INFORMATION: HBV BCP (5' nt 1755-1772)

<400> SEQUENCE: 229
aggttaaagg tctttgta                                                   18

<210> SEQ ID NO 230
<211> LENGTH: 18
<212> TYPE: DNA
<213> ORGANISM: Artificial Sequence
<220> FEATURE:
<223> OTHER INFORMATION: HBV BVP (complement to 5' nt 1755-1772)

<400> SEQUENCE: 230
tccaatttcc agaaacat                                                   18

<210> SEQ ID NO 231
<211> LENGTH: 26
<212> TYPE: DNA
<213> ORGANISM: Artificial Sequence
<220> FEATURE:
<223> OTHER INFORMATION: WT Sox7 probe

<400> SEQUENCE: 231
gattaggtta aaggtctttg tattag                                          26

<210> SEQ ID NO 232
<211> LENGTH: 29
<212> TYPE: DNA
<213> ORGANISM: Artificial Sequence
<220> FEATURE:
<223> OTHER INFORMATION: HNF4aN3Sox7 probe

<400> SEQUENCE: 232
gattaggtta aaggtcactt ttgtattag                                       29

<210> SEQ ID NO 233
<211> LENGTH: 13
<212> TYPE: DNA
<213> ORGANISM: Artificial Sequence
<220> FEATURE:
<223> OTHER INFORMATION: WT HBVCP

<400> SEQUENCE: 233
aggttaaagg tct                                                        13

<210> SEQ ID NO 234
<211> LENGTH: 13
<212> TYPE: DNA
<213> ORGANISM: Artificial Sequence
<220> FEATURE:
<223> OTHER INFORMATION: HNF4a motif mutant

<400> SEQUENCE: 234
cttttaaagg tct                                                        13

<210> SEQ ID NO 235
<211> LENGTH: 137
<212> TYPE: PRT
<213> ORGANISM: Homo sapiens

```
<400> SEQUENCE: 235

Phe Gln Cys Asn Leu Cys Asn Lys Thr Tyr Ser Thr Phe Ser Gly Leu
1               5                   10                  15

Ala Lys His Lys Gln Leu His Cys Asp Ala Gln Ser Arg Lys Ser Phe
            20                  25                  30

Ser Cys Lys Tyr Cys Asp Lys Glu Tyr Val Ser Leu Gly Ala Leu Lys
        35                  40                  45

Met His Ile Arg Thr His Thr Leu Pro Cys Val Cys Lys Ile Cys Gly
    50                  55                  60

Lys Ala Phe Ser Arg Pro Trp Leu Leu Gln Gly His Ile Arg Thr His
65                  70                  75                  80

Thr Gly Glu Lys Pro Phe Ser Cys Pro His Cys Asn Arg Ala Phe Ala
                85                  90                  95

Asp Arg Ser Asn Leu Arg Ala His Leu Gln Thr His Ser Asp Val Lys
                100                 105                 110

Lys Tyr Gln Cys Lys Asn Cys Ser Lys Thr Phe Ser Arg Met Ser Leu
            115                 120                 125

Leu His Lys His Glu Glu Ser Gly Cys
    130                 135

<210> SEQ ID NO 236
<211> LENGTH: 69
<212> TYPE: PRT
<213> ORGANISM: Homo sapiens

<400> SEQUENCE: 236

Ile Arg Arg Pro Met Asn Ala Phe Met Val Trp Ala Lys Asp Glu Arg
1               5                   10                  15

Lys Arg Leu Ala Val Gln Asn Pro Asp Leu His Asn Ala Glu Leu Ser
            20                  25                  30

Lys Met Leu Gly Lys Ser Trp Lys Ala Leu Thr Leu Ser Gln Lys Arg
        35                  40                  45

Pro Tyr Val Asp Glu Ala Glu Arg Leu Arg Leu Gln His Met Gln Asp
    50                  55                  60

Tyr Pro Asn Tyr Lys
65
```